US008741604B2

(12) United States Patent
Campbell et al.

(10) Patent No.: US 8,741,604 B2
(45) Date of Patent: Jun. 3, 2014

(54) NUCLEIC ACID MOLECULE ENCODING A SPECIFIC IL-1R1 ANTIBODY

(75) Inventors: Jamie Iain Campbell, Cambridgeshire (GB); Duncan James Cochrane, Cambridgeshire (GB); Donna Kirsty Finch, Cambridgeshire (GB); Maria Anastasia Teresa Groves, Cambridge (GB); David Christopher Lowe, Cambridge (GB); Simon Charles Cruwys, Leicestershire (GB)

(73) Assignee: Medimmune Limited, Cambridge (GB)

( * ) Notice: Subject to any disclaimer, the term of this patent is extended or adjusted under 35 U.S.C. 154(b) by 0 days.

(21) Appl. No.: 13/618,366

(22) Filed: Sep. 14, 2012

(65) Prior Publication Data

US 2013/0078717 A1    Mar. 28, 2013

Related U.S. Application Data

(63) Continuation of application No. 12/612,781, filed on Nov. 5, 2009, now Pat. No. 8,298,533.

(60) Provisional application No. 61/112,381, filed on Nov. 7, 2008.

(51) Int. Cl.
  *C12P 19/34*     (2006.01)
  *C12N 15/13*     (2006.01)
  *C12N 5/07*      (2010.01)
  *C12N 15/74*     (2006.01)
  *C12N 15/85*     (2006.01)

(52) U.S. Cl.
  USPC .......... 435/91.1; 435/326; 435/331; 435/455; 435/476; 424/139.1

(58) Field of Classification Search
  None
  See application file for complete search history.

(56) References Cited

U.S. PATENT DOCUMENTS

| | | |
|---|---|---|
| 5,296,592 A | 3/1994 | Dower et al. |
| 5,565,332 A | 10/1996 | Hoogenboom et al. |
| 5,585,089 A | 12/1996 | Queen et al. |
| 5,624,821 A | 4/1997 | Winter et al. |
| 5,648,260 A | 7/1997 | Winter et al. |
| 5,677,425 A | 10/1997 | Bodner et al. |
| 5,733,743 A | 3/1998 | Johnson et al. |
| 5,858,657 A | 1/1999 | Winter et al. |
| 5,869,046 A | 2/1999 | Presta et al. |
| 5,871,907 A | 2/1999 | Winter et al. |
| 5,872,215 A | 2/1999 | Osbourn et al. |
| 5,885,573 A | 3/1999 | Bluestone et al. |
| 5,885,793 A | 3/1999 | Griffiths et al. |
| 5,962,255 A | 10/1999 | Griffiths et al. |
| 5,969,108 A | 10/1999 | McCafferty et al. |
| 6,121,022 A | 9/2000 | Presta et al. |
| 6,140,471 A | 10/2000 | Johnson et al. |
| 6,165,745 A | 12/2000 | Ward et al. |
| 6,172,197 B1 | 1/2001 | McCafferty et al. |
| 6,194,551 B1 | 2/2001 | Idusogie et al. |
| 6,225,447 B1 | 5/2001 | Winter et al. |
| 6,277,375 B1 | 8/2001 | Ward et al. |
| 6,291,650 B1 | 9/2001 | Winter et al. |
| 6,492,160 B1 | 12/2002 | Griffiths et al. |
| 6,511,665 B1 | 1/2003 | Dower et al. |
| 6,521,404 B1 | 2/2003 | Griffiths et al. |
| 6,528,624 B1 | 3/2003 | Idusogie et al. |
| 6,682,736 B1 | 1/2004 | Hanson et al. |
| 6,737,056 B1 | 5/2004 | Presta |
| 6,821,505 B2 | 11/2004 | Ward |
| 7,087,224 B2 | 8/2006 | Kay et al. |
| 7,115,717 B2 | 10/2006 | Mori et al. |
| 7,132,281 B2 | 11/2006 | Hanson et al. |
| 7,202,343 B2 | 4/2007 | Gudas et al. |
| 7,217,796 B2 | 5/2007 | Wang et al. |
| 7,438,910 B2 | 10/2008 | Varnum et al. |
| 8,298,533 B2 | 10/2012 | Campbell et al. |
| 2004/0002587 A1 | 1/2004 | Watkins et al. |
| 2004/0071702 A1 | 4/2004 | van de Winkel et al. |
| 2007/0248597 A1 | 10/2007 | Henley, III et al. |

FOREIGN PATENT DOCUMENTS

| | | |
|---|---|---|
| EP | 0592106 A1 | 4/1994 |
| WO | WO 91/09967 | 7/1991 |
| WO | WO 92/01047 | 1/1992 |
| WO | WO 93/11161 | 6/1993 |
| WO | WO 93/17105 | 9/1993 |
| WO | WO 94/13804 | 6/1994 |
| WO | WO 94/29351 | 12/1994 |
| WO | WO 96/27011 | 9/1996 |
| WO | WO 97/43316 | 11/1997 |
| WO | WO 98/23289 | 6/1998 |
| WO | WO 98/50431 | 11/1998 |
| WO | WO 99/58572 | 11/1999 |
| WO | WO 00/42072 | 7/2000 |

(Continued)

OTHER PUBLICATIONS

Al-Lazikani, Bissan et al., 1997, "Standard Conformations for the Canonical Structures of Immunoglobulins", J. Mol. Biol., 273(4):927-948.

Amit, A. G. et al., 1986, "Three-Dimensional Structure of an Antigen-Antibody Complex at 2.8 Å Resolution", Science, 233:747-753.

Anderson, Dana C. et al., 2002, "Recombinant protein expression for therapeutic applications", Current Opinion in Biotechnology, 13:117-123.

Bagshawe, K.D., et al., 1991, "Antibody-Enzyme Conjugates Can Generate Cytotoxic Drugs from Inactive Precursors at Tumor Sites", Antibody, Immunoconjugates and Radiopharmaceuticals 4: 915-922.

(Continued)

*Primary Examiner* — Elly-Gerald Stoica

(57) ABSTRACT

This invention relates to binding members, especially antibody molecules, specific for interleukin 1 receptor 1 (IL-1R1). For example, isolated binding members specific for IL-1R1 which competes with IL-1 and IL-1Ra for binding to IL-1R1 and binds Il-1R1 with a $K_D$ of 10 pM or less when measured by Kinexa™. The binding members are useful for, inter alia, treatment of disorders mediated by IL-1R1 including rheumatoid arthritis, asthma and chronic obstructive pulmonary disease (COPD).

6 Claims, 14 Drawing Sheets

(56) References Cited

FOREIGN PATENT DOCUMENTS

| | | |
|---|---|---|
| WO | WO 02/060919 A2 | 8/2002 |
| WO | WO 2004/006955 A1 | 1/2004 |
| WO | WO 2004/022718 A2 | 3/2004 |
| WO | WO 2004/029207 A2 | 4/2004 |
| WO | WO 2004/063351 A2 | 7/2004 |
| WO | WO 2004/099249 A2 | 11/2004 |
| WO | WO 2005/023872 A1 | 3/2005 |
| WO | WO 2006/023403 A2 | 3/2006 |
| WO | WO 2006/028936 A2 | 3/2006 |
| WO | WO 2006/059108 A2 | 6/2006 |
| WO | WO 2007/063308 A2 | 6/2007 |
| WO | WO 2007/063311 A2 | 6/2007 |

OTHER PUBLICATIONS

Bannister, David et al., 2006, "Parallel, High-Throughput Purification of Recombinant Antibodies for in Vivo Cell Assays", Biotechnology and Bioengineering, 94(5):931-937.

Bird, Robert E. et al., 1988, "Single-Chain Antigen-Binding Proteins", Science, 242:423-426.

Caton, Andrew J. et al., 1990, "Identical D Region Sequences Expressed by Murine Monoclonal Antibodies Specific for a Human Tumor-Associated Antigen", The Journal of Immunology, 144:1965-1968.

Chadd, Helen E. et al., 2001, "Therapeutic antibody expression technology", Current Opinion in Biotechnology, 12:188-194.

Chothia, Cyrus et al., 1987, "Canonical Structures for the Hypervariable Regions of Immunoglobulins", J. Mol. Biol. 196:901-917.

Chothia, Cyrus et al., 1989, "Conformations of immunoglobulin hypervariable regions", Nature, 342:877-883.

Chothia, Cyrus et al., 1992, "Structural Repertoire of the Human $V_H$Segments", 227:799-817.

Dinarello, Charles A., 1996, "Biologic Basis for Interleukin-1 in Disease", Blood 87(6):2095-2147.

Dinarello, C.A., 2002, "The IL-1 family and inflammatory diseases", Clin. Exp. Rheumatol., 20(5): Suppl. 27:S1-S13.

Dunn, Eleanor et al., 2001, "Annotating genes with potential roles in the immune system: six new members of the IL-1 family", Trends in Immunology, 22(10):533-536.

Gram, Hermann et al., 1992, "In vitro selection and affinity maturation of antibodies from a naive combinatorial immunoglobulin library", Proc. Natl. Acad. Sci., USA, 89:3576-3580.

Greenfeder, Scott A., et al. 1995,"Molecular Cloning and Characterization of a Second Subunit of the Interleukin 1 Receptor Complex", The Journal of Biological Chemistry, 270(23):13757-13765.

Groves, Maria AT et al., 2005, "Applications of ribosome display to antibody drug discovery", Expert Opin. Biol. Ther. 5(1):125-135.

Groves, Maria et al., 2006, "Affinity maturation of phage display antibody populations using ribosome display", Journal of Immunological Methods, 313:129-139.

Holliger, Philipp et al., 1993, "Diabodies: Small bivalent and bispecific antibody fragments", Proc. Natl. Acad. Sci. USA, 6444-6448.

Holliger, Philipp et al., 1993, "Engineering bispecific antibodies", Current Opinion in Biotechnology, 4:446-449.

Holliger, Philipp et al., 1999, "Engineering antibodies for the clinic", Cancer and Metastasis Reviews, 18:411-419.

Holliger, Philipp et al., 2005, "Engineered antibody fragments and the rise of single domain", Nature Biotechnology, 23(9):1126-1136.

Holt, Lucy J. et al., 2003, "Domain antibodies: proteins for therapy", Trends in Biotechnology, 21:484-490.

Huston, James S. et al., 1988, "Protein engineering of antibody binding sites: Recovery of specific activity in an anti-digoxin single-chain Fv analogue produced in *Escherichia coli*", Proc. Natl. Acad. Sci. USA, 85:5879-5883.

Hu, Shi-zhen, et al., 1996, "Minibody: A Novel Engineered Anti-Carcinoembryonic Antigen Antibody Fragment (Single-Chain Fv-$C_H3$) Which Exhibits Rapid, High-Level Targeting of Xenografts", Cancer Research, 56: 3055-3061.

Ikonomidias, Ignatios, M.D., et al. 2008, "Inhibition of Interleukin-1 by Anakinra Improves Vascular and Left Ventricular Function in Patients With Rheumatoid Arthritis", Circulation 117:2662-2669.

International Search Report for PCT/GB2009/051495 mailed Apr. 20, 2010.

Kabat, Elvin A. et al., 1991, "Identical V Region Amino Acid Sequences and Segments of Sequences in Antibodies of Different Specificities", The Journal of Immunology, 147:1709-1719.

Knappik, Achim et al., 2000, "Fully Synthetic Human Combinatorial Antibody Libraries (HuCAL) Based on Modular Consensus Frameworks and CDS Randomized with Trinucleotides", J. Mol. Biol. 296:57-86.

Köhler, G. et al., 1975, "Continuous cultures of fused cells secreting antibody of predefined specificity", Nature, 256:495-497.

Krebs, Barbara et al., 2001, "High-throughput generation and engineering of recombinant human antibodies", Journal of Immunological Methods, 254:67-84.

Larsen, Claus M. Et al., 2007, "Interleukin-1-Receptor Antagonist in Type 2 Diabetes Mellitus", The New England Journal of Medicine, 356:1517-1526.

Larrick, James W. et al., 2001, "Producing proteins in transgenic plants and animals", Current Opinion in Biotechnology, 12:411-418.

Ledermann, J.A. et al., 1991, "A Phase-1 Study of Repeated Therapy With Radiolabelled Antibody to Carcinoembryonic Antigen Using Intermittent or Continuous Administration of Cyclosporin A to Suppress the Immune Response", Int. J. Cancer, 47:659-664.

Mach, Henryk et al., 1992, "Detection of Proteins and Phenol in DNA Samples with Second-Derivative Absorption Spectroscopy", Biochemistry, 200:20-26.

Marks, James D. et al., 1992, "By-Passing Immunization: Building High Affinity Human Antibodies by Chain Shuffling", Bio/Technology, 10:779-783.

McCafferty, John et al., 1990, "Phage antibodies: filamentous phage displaying antibody variable domains", Nature, 348:552-554.

Mizel, Steven B., et al., 1997, "The Interleukin 1 Receptor, Dynamics of Interleukin 1 Binding and Internationalization in T Cells and Fibroblasts", The Journal of Immunology, 138:2906-2912.

Osbourn, Jane K. et al, 1996, "Generation of a panel of related human scFv antibodies with high affinities for human CEA", Immunotechnology, 2:181-196.

Osbourn, O. et al., 2008, "Treatment with an Interleukin 1 beta antibody improves glycemic control in diet-induced obesity", Cytokine, 44:141-148.

Persic, Lidija et al., 1997, "An integrated vector system for the eukaryotic expression of antibodies or their fragments after selection from phage display libraries", Gene, 187:9-18.

Plückthun, Andreas, 1991, "Antibody Engineering: Advances From the Use of *Escherichia Coli* Expression Systems", Bio/Technology, 9:545-551.

Qwarnstrom, Eva E., et al., 1988, "Binding, Internalization, and Intracellular Localization of Interleukin-1β in Human Diploid Fibroblasts", 263:8261-8269.

Reiter, Yoram et al., 1996, "Engineering antibody Fv fragments for cancer detection and therapy: Disulfide-stabilized Fv fragments", Nature Biotechnology, 14:1239-1245.

Roskos, Lorin et al., 2007, "Molecular Engineering II: Antibody Affinity", Handbook of Therapeutic Antibodies, Chapter 7, pp. 145-169.

Rudikoff, Stuart, et al., 1982, "Single amino acid substitution altering antigen-binding specificity," Proc. Natl. Acad. Sci. USA, 79:1979-1983.

Sauter, Nadine S., et al., 2008, "The Antiinflammatory Cytokine Interleukin-1 Receptor Antagonist Protects from High-Fat Diet-Induced Hyperglycemia", Endocrinology, 149(5):2208-2218.

Schmitz et al., 2005, "IL-33, an Interleukin-1-like Cytokine that Signals via the IL-1 Receptor-Related Protein ST2 and Induces T Helper Type 2-Associated Cytokines", Immunity 23, 479-490.

Schreuder, Herman et al., 1997, "A new cytokine-receptor binding mode revealed by the crystal structure of the IL-1 receptor with an antagonist", Nature, 386:194-200.

(56) References Cited

OTHER PUBLICATIONS

Segal, David M. et al., 1974, "The Three-Dimensional Structure of a Phosphorylcholine-Binding Mouse Immungloubulin Fab and the Nature of the Antigen Binding Site", Proc. Natl. Acad. Sci. USA, 71:4298-4302.

Sharon, Jacqueline, 1990, "Structural correlates of high antibody affinity: Three engineered amino acid substitutions can increase the affinity of an anti-*p*-azophenylarsonate antibody 200-fold", Proc. Natl. Acad. Sci. USA, 87:4814-4817.

Sharon, Jacqueline, 1990, "Structural Characterization of Idiotopes by Using Antibody Variants Generated by Site-Directed Mutagenesis", The Journal of Immunology, 144:4863-4869.

Sims, John E., 2002, "IL-1 and IL-18 receptors, and their extended family", Current Opinion in Immunology, 14:117-122.

Sims, John E., 1994, "The Two Interleukin-1 Receptors Play Different Roles in IL-1 Actions", Clinical Immunology and Immunopathology, 72(1):9-14.

Thompson, Julia et al., 1996, "Affinity Maturation of a High-affinity Human Monoclonal Antibody Against the Third Hypervariable Loop of Human Immunodeficiency Virus: Use of Phage Display to Improve Affinity and Broaden Strain Reactivity", J. Mol. Biol., 256:77-88.

Vaughan, Tristan J. et al., 1996, "Human Antibodies with Sub-nanomolar Affinities Isolated from a Large Non-immunized Phage Display Library", Nature Biotechnology, 14:309-314.

Vigers, Guy P.A., et al., 1997, "Crystal structure of the type-1 Interleukin-1 receptor complexed with interleukin-1β", Nature, 386:190-194.

Wanderer, Alan A., et al., 2008, "Ischemic-reperfusin syndromes: Biochemical and immunologic rationale for IL-1 targeted therapy", Clinical Immunology, 128:127-132.

Ward, E. Sally, et al., 1989, "Binding activities of a repertoire of single immunoglobulin variable domains secreted from *Escherichia coli*", Nature, 341:544-546.

Figure 1
Cynomolgus Monkey IL-1R1 extracellular domain cDNA

ATGAAAGTGTTACTCCGACTTATTTGTTTCATTGCTCTACTGATTTCTTTTCTGGAGG
CTGATAAATGCAATGAACGTGAAGAAAAAATAATTTTAGTGTCATCTGCAAATGAA
ATTGATGTTCGTCCCTGTCCTCTTAACCCAAATGAATACAAAGGCACTATAACATGG
TATAAAAATGACAGCAAGACACCTATATCTACAGAACAAGCCTCCAGGATTCATCA
GCACAAAAAGAAACTTTGGTTTGTTCCTGCTAAGGTAGAAGATTCAGGACATTACTA
CTGTGTGGTAAGAAATTCATCTTACTGCCTCAGAATTAAAATAACTGCAAAATTTGT
GGAGAATGAGCCTAACTTGTGTTATAATGCAGAAGCCATATTTAAGCAGAGACTAC
CCGTTGCAGGAGATGGAGGACTTGTGTGCCCTTATATGGAGTTTTTTAAAGACGAAA
ATAATGAGTTACCTAAATTACTGTGGTATAAGGATTGCAAACCTCTACTTCTTGACA
ATATAAACTTTAGTGGAGTCAAAGATAGGCTCATCGTGATGAATGTGGCTGAAAAG
CATAGAGGGAACTATACTTGTCATGCATCCTACACATACTTGGGCAAGCAATATCCT
ATTACCCGGGTAATAGAATTTATTACTCTAGAGGAAAACAAACCCACAAGGCCTGT
GATTGTGAGCCCAGCTAATGAGACAATAGAAGTAGACTTGGGATCCCAGATACAAT
TGATCTGTAATGTCACTGGCCAGTTGAGTGATACTGCCTACTGGAAGTGGAATGGGT
CCTTCATTGATGAAGATGACCCAGTGCTAGGGGAAGACTATTACAGTGTGGAAAAT
CCTGCAAACAAAAGAAGGAGTACCCTCATCACAGTGCTTAATATATCAGAAACTGA
AAGTAGATTTTATAAACATCCATTTACCTGTTTAGCCAGGAATACACATGGTATGGA
TGCAGCATATGTCCAGTTAATATATCCAGTCACTAAATTCCAGAAG

Figure 2

Cynomolgus Monkey IL-1R1 extracellular domain amino acid sequence

MKVLLRLICFIALLISFLEADKCNEREEKIILVSSANEIDVRPCPLNPNEYKGTITWYKNDS
KTPISTEQASRIHQHKKKLWFVPAKVEDSGHYYCVVRNSSYCLRIKITAKFVENEPNLCY
NAEAIFKQRLPVAGDGGLVCPYMEFFKDENNELPKLLWYKDCKPLLLDNINFSGVKDR
LIVMNVAEKHRGNYTCHASYTYLGKQYPITRVIEFITLEENKPTRPVIVSPANETIEVDLG
SQIQLICNVTGQLSDTAYWKWNGSFIDEDDPVLGEDYYSVENPANKRRSTLITVLNISET
ESRFYKHPFTCLARNTHGMDAAYVQLIYPVTKFQK

Figure 3

Human IL1R1Fc cDNA nucleotide

ATGAAAGTGTTACTCAGACTTATTTGTTTCATAGCTCTACTGATTTCTTCTCTGGAGG
CTGATAAATGCAAGGAACGTGAAGAAAAAATAATTTTAGTGTCATCTGCAAATGAA
ATTGATGTTCGTCCCTGTCCTCTTAACCCAAATGAACACAAAGGCACTATAACTTGG
TATAAAGATGACAGCAAGACACCTGTATCTACAGAACAAGCCTCCAGGATTCATCA
ACACAAAGAGAAACTTTGGTTTGTTCCTGCTAAGGTGGAGGATTCAGGACATTACTA
TTGCGTGGTAAGAAATTCATCTTACTGCCTCAGAATTAAAATAAGTGCAAAATTTGT
GGAGAATGAGCCTAACTTATGTTATAATGCACAAGCCATATTTAAGCAGAAACTAC
CCGTTGCAGGAGACGGAGGACTTGTGTGCCCTTATATGGAGTTTTTTAAAAATGAAA
ATAATGAGTTACCTAAATTACAGTGGTATAAGGATTGCAAACCTCTACTTCTTGACA
ATATACACTTTAGTGGAGTCAAAGATAGGCTCATCGTGATGAATGTGGCTGAAAAG
CATAGAGGGAACTATACTTGTCATGCATCCTACACATACTTGGGCAAGCAATATCCT
ATTACCCGGGTAATAGAATTTATTACTCTAGAGGAAAACAAACCCACAAGGCCTGT
GATTGTGAGCCCAGCTAATGAGACAATGGAAGTAGACTTGGGATCCCAGATACAAT
TGATCTGTAATGTCACCGGCCAGTTGAGTGACATTGCTTACTGGAAGTGGAATGGGT
CAGTAATTGATGAAGATGACCCAGTGCTAGGGGAAGACTATTACAGTGTGGAAAAT
CCTGCAAACAAAAGAAGGAGTACCCTCATCACAGTGCTTAATATATCGGAAATTGA
AAGTAGATTTTATAAACATCCATTTACCTGTTTTGCCAAGAATACACATGGTATAGA
TGCAGCATATATCCAGTTAATATATCCAGTCACTAATTTCCAGAAGAAGGGTGGGCG
CGCCGACCCAGCTTTCTTGTACAAAGTGGTGGGGGCCGCCCCCAAATCTTGTGACAA
AACTCACACATGCCCACCGTGCCCAGCACCTGAACTCCTGGGGGGACCGTCAGTCTT
CCTCTTCCCCCCAAAACCCAAGGACACCCTCATGATCTCCCGGACCCCTGAGGTCAC
ATGCGTGGTGGTGGACGTGAGCCACGAAGACCCTGAGGTCAAGTTCAACTGGTACG
TGGACGGCGTGGAGGTGCATAATGCCAAGACAAAGCCGCGGGAGGAGCAGTACAA
CAGCACGTACCGTGTGGTCAGCGTCCTCACCGTCCTGCACCAGGACTGGCTGAATGG
CAAGGAGTACAAGTGCAAGGTCTCCAACAAAGCCCTCCCAGCCCCCATCGAGAAAA
CCATCTCCAAAGCCAAAGGGCAGCCCCGAGAACCACAGGTGTACACCCTGCCCCCA
TCCCGGGAGGAGATGACCAAGAACCAGGTCAGCCTGACCTGCCTGGTCAAAGGCTT
CTATCCCAGCGACATCGCCGTGGAGTGGGAGAGCAATGGGCAGCCGGAGAACAACT
ACAAGACCACGCCTCCCGTGCTGGACTCCGACGGCTCCTTCTTCCTCTATAGCAAGC
TCACCGTGGACAAGAGCAGGTGGCAGCAGGGGAACGTCTTCTCATGCTCCGTGATG
CATGAGGCTCTGCACAACCACTACACGCAGAAGAGCCTCTCCCTGTCTCCGGGTAAA
CATCATCATCACCACCATTAA

Figure 4
Human IL1R1Fc protein

```
  1 MKVLLRLICF IALLISSLEA DKCKEREEKI ILVSSANEID VRPCPLNPNE HKGTITWYKD
 61 DSKTPVSTEQ ASRIHQHKEK LWFVPAKVED SGHYYCVVRN SSYCLRIKIS AKFVENEPNL
121 CYNAQAIFKQ KLPVAGDGGL VCPYMEFFKN ENNELPKLQW YKDCKPLLLD
    NIHFSGVKDR
181 LIVMNVAEKH RGNYTCHASY TYLGKQYPIT RVIEFITLEE NKPTRPVIVS PANETMEVDL
241 GSQIQLICNV TGQLSDIAYW KWNGSVIDED DPVLGEDYYS VENPANKRRS TLITVLNISE
301 IESRFYKHPF TCFAKNTHGI DAAYIQLIYP VTNFQKKGGR ADPAFLYKVV GAAPKSCDKT
361 HTCPPCPAPE LLGGPSVFLF PPKPKDTLMI SRTPEVTCVV VDVSHEDPEV KFNWYVDGVE
421 VHNAKTKPRE EQYNSTYRVV SVLTVLHQDW LNGKEYKCKV SNKALPAPIE
    KTISKAKGQP
481 REPQVYTLPP SREEMTKNQV SLTCLVKGFY PSDIAVEWES NGQPENNYKT TPPVLDSDGS
541 FFLYSKLTVD KSRWQQGNVF SCSVMHEALH NHYTQKSLSL SPGKHHHHHH *
```

Figure 5

Cynomolgus Monkey IL1R1Fc cDNA nucleotide

ATGAAAGTGTTACTCCGACTTATTTGTTTCATTGCTCTACTGATTTCTTTTCTGGAGG
CTGATAAATGCAATGAACGTGAAGAAAAATAATTTTAGTGTCATCTGCAAATGAA
ATTGATGTTCGTCCCTGTCCTCTTAACCCAAATGAATACAAAGGCACTATAACATGG
TATAAAAATGACAGCAAGACACCTATATCTACAGAACAAGCCTCCAGGATTCATCA
GCACAAAAGAAACTTTGGTTTGTTCCTGCTAAGGTAGAAGATTCAGGACATTACTA
CTGTGTGGTAAGAAATTCATCTTACTGCCTCAGAATTAAAATAACTGCAAAATTTGT
GGAGAATGAGCCTAACTTGTGTTATAATGCAGAAGCCATATTTAAGCAGAGACTAC
CCGTTGCAGGAGATGGAGGACTTGTGTGCCCTTATATGGAGTTTTTTAAAGACGAAA
ATAATGAGTTACCTAAATTACTGTGGTATAAGGATTGCAAACCTCTACTTCTTGACA
ATATAAACTTTAGTGGAGTCAAAGATAGGCTCATCGTGATGAATGTGGCTGAAAAG
CATAGAGGGAACTATACTTGTCATGCATCCTACACATACTTGGGCAAGCAATATCCT
ATTACCCGGGTAATAGAATTTATTACTCTAGAGGAAAACAAACCCACAAGGCCTGT
GATTGTGAGCCCAGCTAATGAGACAATAGAAGTAGACTTGGGATCCCAGATACAAT
TGATCTGTAATGTCACTGGCCAGTTGAGTGATACTGCCTACTGGAAGTGGAATGGGT
CCTTCATTGATGAAGATGACCCAGTGCTAGGGGAAGACTATTACAGTGTGGAAAAT
CCTGCAAACAAAAGAAGGAGTACCCTCATCACAGTGCTTAATATATCAGAAACTGA
AAGTAGATTTTATAAACATCCATTTACCTGTTTAGCCAGGAATACACATGGTATGGA
TGCAGCATATGTCCAGTTAATATATCCAGTCACTAAATTCCAGAAGAAGGGTGGGC
GCGCCGACCCAGCTTTCTTGTACAAAGTGGTGGGGGCCGCCCCCAAATCTTGTGACA
AAACTCACACATGCCCACCGTGCCCAGCACCTGAACTCCTGGGGGGACCGTCAGTCT
TCCTCTTCCCCCCAAAACCCAAGGACACCCTCATGATCTCCCGGACCCCTGAGGTCA
CATGCGTGGTGGTGGACGTGAGCCACGAAGACCCTGAGGTCAAGTTCAACTGGTAC
GTGGACGGCGTGGAGGTGCATAATGCCAAGACAAAGCCGCGGGAGGAGCAGTACA
ACAGCACGTACCGTGTGGTCAGCGTCCTCACCGTCCTGCACCAGGACTGGCTGAATG
GCAAGGAGTACAAGTGCAAGGTCTCCAACAAAGCCCTCCCAGCCCCCATCGAGAAA
ACCATCTCCAAAGCCAAAGGGCAGCCCCGAGAACCACAGGTGTACACCCTGCCCCC
ATCCCGGGAGGAGATGACCAAGAACCAGGTCAGCCTGACCTGCCTGGTCAAAGGCT
TCTATCCCAGCGACATCGCCGTGGAGTGGGAGAGCAATGGGCAGCCGGAGAACAAC
TACAAGACCACGCCTCCCGTGCTGGACTCCGACGGCTCCTTCTTCCTCTATAGCAAG
CTCACCGTGGACAAGAGCAGGTGGCAGCAGGGGAACGTCTTCTCATGCTCCGTGAT
GCATGAGGCTCTGCACAACCACTACACGCAGAAGAGCCTCTCCCTGTCTCCGGGTAA
ACATCATCATCACCACCATTAA

Figure 6

Cynomolgus Monkey IL1R1Fc protein

```
  1 MKVLLRLICF IALLISFLEA DKCNEREEKI ILVSSANEID VRPCPLNPNE YKGTITWYKN
 61 DSKTPISTEQ ASRIHQHKKK LWFVPAKVED SGHYYCVVRN SSYCLRIKIT AKFVENEPNL
121 CYNAEAIFKQ RLPVAGDGGL VCPYMEFFKD ENNELPKLLW YKDCKPLLLD
NINFSGVKDR
181 LIVMNVAEKH RGNYTCHASY TYLGKQYPIT RVIEFITLEE NKPTRPVIVS PANETIEVDL
241 GSQIQLICNV TGQLSDTAYW KWNGSFIDED DPVLGEDYYS VENPANKRRS TLITVLNISE
301 TESRFYKHPF TCLARNTHGM DAAYVQLIYP VTKFQKKGGR ADPAFLYKVV
GAAPKSCDKT
361 HTCPPCPAPE LLGGPSVFLF PPKPKDTLMI SRTPEVTCVV VDVSHEDPEV KFNWYVDGVE
421 VHNAKTKPRE EQYNSTYRVV SVLTVLHQDW LNGKEYKCKV SNKALPAPIE
KTISKAKGQP
481 REPQVYTLPP SREEMTKNQV SLTCLVKGFY PSDIAVEWES NGQPENNYKT TPPVLDSDGS
541 FFLYSKLTVD KSRWQQGNVF SCSVMHEALH NHYTQKSLSL SPGKHHHHHH *
```

Figure 7

Human IL-1R1 extracellular sequence

MKVLLRLICFIALLISSLEADKCKEREEKIILVSSANEIDVRPCPLNPNEHKGTITWYKDDS
KTPVSTEQASRIHQHKEK
LWFVPAKVEDSGHYYCVVRNSSYCLRIKISAKFVENEPNLCYNAQAIFKQKLPVAGDGG
LVCPYMEFFKNENNELPKLQW
YKDCKPLLLDNIHFSGVKDRLIVMNVAEKHRGNYTCHASYTYLGKQYPITRVIEFITLEE
NKPTRPVIVSPANETMEVDL
GSQIQLICNVTGQLSDIAYWKWNGSVIDEDDPVLGEDYYSVENPANKRRSTLITVLNISEI
ESRFYKHPFTCFAKNTHGI
DAAYIQLIYPVTNFQK

Figure 8

Human IL-1R1 cDNA sequence

CACCATGAAAGTGTTACTCAGACTTATTTGTTTCATAGCTCTACTGATTTCTTCTCTG
GAGGCTGATAAATGCAAGGAAC
GTGAAGAAAAAATAATTTTAGTGTCATCTGCAAATGAAATTGATGTTCGTCCCTGTC
CTCTTAACCCAAATGAACACAAA
GGCACTATAACTTGGTATAAAGATGACAGCAAGACACCTGTATCTACAGAACAAGC
CTCCAGGATTCATCAACACAAAGA
GAAACTTTGGTTTGTTCCTGCTAAGGTGGAGGATTCAGGACATTACTATTGCGTGGT
AAGAAATTCATCTTACTGCCTCA
GAATTAAAATAAGTGCAAAATTTGTGGAGAATGAGCCTAACTTATGTTATAATGCAC
AAGCCATATTTAAGCAGAAACTA
CCCGTTGCAGGAGACGGAGGACTTGTGTGCCCTTATATGGAGTTTTTTAAAAATGAA
AATAATGAGTTACCTAAATTACA
GTGGTATAAGGATTGCAAACCTCTACTTCTTGACAATATACACTTTAGTGGAGTCAA
AGATAGGCTCATCGTGATGAATG
TGGCTGAAAAGCATAGAGGGAACTATACTTGTCATGCATCCTACACATACTTGGGCA
AGCAATATCCTATTACCCGGGTA
ATAGAATTTATTACTCTAGAGGAAAACAAACCCACAAGGCCTGTGATTGTGAGCCC
AGCTAATGAGACAATGGAAGTAGA
CTTGGGATCCCAGATACAATTGATCTGTAATGTCACCGGCCAGTTGAGTGACATTGC
TTACTGGAAGTGGAATGGGTCAG
TAATTGATGAAGATGACCCAGTGCTAGGGGAAGACTATTACAGTGTGGAAAATCCT
GCAAACAAAAGAAGGAGTACCCTC
ATCACAGTGCTTAATATATCGGAAATTGAAAGTAGATTTTATAAACATCCATTTACC
TGTTTTGCCAAGAATACACATGG
TATAGATGCAGCATATATCCAGTTAATATATCCAGTCACTAATTTCCAGAAG

Figure 9

Cyno IL-1R1 Extracellular sequence (residues 1 to 337)

MKVLLRLICFIALLISFLEADKCNEREEKIILVSSANEIDVRPCPLNPNEYKGTITWYKNDS
KTPISTEQASRIHQHKKK
LWFVPAKVEDSGHYYCVVRNSSYCLRIKITAKFVENEPNLCYNAEAIFKQRLPVAGDGG
LVCPYMEFFKDENNELPKLLW
YKDCKPLLLDNINFSGVKDRLIVMNVAEKHRGNYTCHASYTYLGKQYPITRVIEFITLEE
NKPTRPVIVSPANETIEVDL
GSQIQLICNVTGQLSDTAYWKWNGSFIDEDDPVLGEDYYSVENPANKRRSTLITVLNISE
TESRFYKHPFTCLARNTHGM
DAAYVQLIYPVTKFQK

Figure 10

Cyno cDNA extracellular IL-1R1 sequence

CACCATGAAAGTGTTACTCCGACTTATTTGTTTCATTGCTCTACTGATTTCTTTTCTG
GAGGCTGATAAATGCAATGAAC
GTGAAGAAAAATAATTTTAGTGTCATCTGCAAATGAAATTGATGTTCGTCCCTGTC
CTCTTAACCCAAATGAATACAAA
GGCACTATAACATGGTATAAAAATGACAGCAAGACACCTATATCTACAGAACAAGC
CTCCAGGATTCATCAGCACAAAA
GAAACTTTGGTTTGTTCCTGCTAAGGTAGAAGATTCAGGACATTACTACTGTGTGGT
AAGAAATTCATCTTACTGCCTCA
GAATTAAAATAACTGCAAAATTTGTGGAGAATGAGCCTAACTTGTGTTATAATGCAG
AAGCCATATTTAAGCAGAGACTA
CCCGTTGCAGGAGATGGAGGACTTGTGTGCCCTTATATGGAGTTTTTTAAAGACGAA
AATAATGAGTTACCTAAATTACT
GTGGTATAAGGATTGCAAACCTCTACTTCTTGACAATATAAACTTTAGTGGAGTCAA
AGATAGGCTCATCGTGATGAATG
TGGCTGAAAAGCATAGAGGGAACTATACTTGTCATGCATCCTACACATACTTGGGCA
AGCAATATCCTATTACCCGGGTA
ATAGAATTTATTACTCTAGAGGAAAACAAACCCACAAGGCCTGTGATTGTGAGCCC
AGCTAATGAGACAATAGAAGTAGA
CTTGGGATCCCAGATACAATTGATCTGTAATGTCACTGGCCAGTTGAGTGATACTGC
CTACTGGAAGTGGAATGGGTCCT
TCATTGATGAAGATGACCCAGTGCTAGGGGAAGACTATTACAGTGTGGAAAATCCT
GCAAACAAAAGAAGGAGTACCCTC
ATCACAGTGCTTAATATATCAGAAACTGAAAGTAGATTTTATAAACATCCATTTACC
TGTTTAGCCAGGAATACACATGG
TATGGATGCAGCATATGTCCAGTTAATATATCCAGTCACTAAATTCCAGAAG

Figure 11

Sequence of mature human HIS-FLAG IL-1ra

MGSSHHHHHHDYKDDDDKHMENLYFQSRPSGRKSSKMQAFRIWDVNQKTFYLRNNQ
LVAGYLQGPNVNLEEKIDVVPIEPHALFLGIHGGKMCLSCVKSGDETRLQLEAVNITDLS
ENRKQDKRFAFIRSDSGPTTSFESAACPGWFLCTAMEADQPVSLTNMPDEGVMVTKFYF
QEDE

Figure 12

Sequence of mature human HIS-FLAG IL-1beta

MGSSHHHHHHDYKDDDDKHMENLYFQSAPVRSLNCTLRDSQQKSLVMSGPYELKALH
LQGQDMEQQVVFSMSFVQGEESNDKIPVALGLKEKNLYLSCVLKDDKPTLQLESVDPK
NYPKKKMEKRFVFNKIEINNKLEFESAQFPNWYISTSQAENMPVFLGGTKGGQDITDFT
MQFVSS

Figure 14

The SDCAT-CG primer which converts Glu to Gln in the Ribosome Display Construction and Retrieval of the Vh3_DP-47_(3-23) family

SDCAT-CG PRIMER
5' AGACCACAACGGTTTCCCTCTAGAAATAATTTTGTTTAACTTTAAGA
                        VH  1   2   3
AGGAGATATATCCATGGCCCAGGTGCAGC3'
                            Gln Val Gln
                            Q   V   Q

Vh3_DP-47_(3-23)  VH  1   2   3
                      GAGGTGCAGC
                      Glu Val Gln
                      E   V   Q

SEQUENCE LISTING

<160> NUMBER OF SEQ ID NOS: 152

<210> SEQ ID NO 1
<211> LENGTH: 378
<212> TYPE: DNA
<213> ORGANISM: Homo sapiens

<400> SEQUENCE: 1

```
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggccgtgt attactgtgc aagagatggc    300
gcgagtagta ccaattgggg atacaccgtg gacgctgcag ttgattgggg cgggggacc    360
acggtcaccg tctcctca                                                 378
```

<210> SEQ ID NO 2
<211> LENGTH: 126
<212> TYPE: PRT
<213> ORGANISM: Homo sapiens

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ala Ser Ser Thr Asn Trp Gly Tyr Thr Val Asp Ala
            100                 105                 110

Ala Val Asp Trp Gly Arg Gly Thr Thr Val Thr Val Ser Ser
        115                 120                 125

<210> SEQ ID NO 3
<211> LENGTH: 5
<212> TYPE: PRT
<213> ORGANISM: Homo sapiens

<400> SEQUENCE: 3

Ser Tyr Ala Met Ser
1               5

<210> SEQ ID NO 4
<211> LENGTH: 17
<212> TYPE: PRT
<213> ORGANISM: Homo sapiens

<400> SEQUENCE: 4

Ala Ile Ser Gly Ser Gly Gly Ser Thr Tyr Tyr Ala Asp Ser Val Lys
1               5                   10                  15

Gly

<210> SEQ ID NO 5
<211> LENGTH: 17
<212> TYPE: PRT
<213> ORGANISM: Homo sapiens

<400> SEQUENCE: 5

Asp Gly Ala Ser Ser Thr Asn Trp Gly Tyr Thr Val Asp Ala Ala Val
                5                   10                  15

Asp

<210> SEQ ID NO 6
<211> LENGTH: 330
<212> TYPE: DNA
<213> ORGANISM: Homo sapiens

<400> SEQUENCE: 6
caggctgtgc tgactcagcc gtcctcagcg tctgggaccc ccgggcagag ggtcaccatc      60
tcttgttctg gcagcagctc aacatcgga agtaattatg tattctggta ccagcagttc     120
ccaggtacgg ccccccaact cctcgtcaaa tggaataatc agcggccctc aggggtccct     180
gaccgattct ctggctccaa gtctggcacc tcagcctccc tggccatcag tggactccgg     240
tccgaggatg aggctgatta ttactgtgca gcatgggatg accacctgga acagctccac     300
ttcggcggag ggaccaagct gaccgtccta                                       330

<210> SEQ ID NO 7
<211> LENGTH: 110
<212> TYPE: PRT
<213> ORGANISM: Homo sapiens

<400> SEQUENCE: 7

Gln Ala Val Leu Thr Gln Pro Ser Ser Ala Ser Gly Thr Pro Gly Gln
                5                   10                  15

Arg Val Thr Ile Ser Cys Ser Gly Ser Ser Ser Asn Ile Gly Ser Asn
            20                  25                  30

Tyr Val Phe Trp Tyr Gln Gln Phe Pro Gly Thr Ala Pro Gln Leu Leu
        35                  40                  45

Val Lys Trp Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp His Leu
                85                  90                  95

Glu Gln Leu His Phe Gly Gly Gly Thr Lys Leu Thr Val Leu
            100                 105                 110

<210> SEQ ID NO 8
<211> LENGTH: 13
<212> TYPE: PRT
<213> ORGANISM: Homo sapiens

<400> SEQUENCE: 8

Ser Gly Ser Ser Ser Asn Ile Gly Ser Asn Tyr Val Phe
                5                   10

<210> SEQ ID NO 9
<211> LENGTH: 7
<212> TYPE: PRT
<213> ORGANISM: Homo sapiens

<400> SEQUENCE: 9

Trp Asn Asn Gln Arg Pro Ser
                5

<210> SEQ ID NO 10
<211> LENGTH: 11
<212> TYPE: PRT

<213> ORGANISM: Homo sapiens

<400> SEQUENCE: 10

Ala Ala Trp Asp Asp His Leu Glu Gln Leu His
              5                  10

<210> SEQ ID NO 11
<211> LENGTH: 381
<212> TYPE: DNA
<213> ORGANISM: Homo sapiens

<400> SEQUENCE: 11
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gaaacccttg     300
tactactatg atgctccccc cccactcgga tatgatggtt ttgatatctg gggccggggg     360
acaatggtca ccgtctcctc a                                               381

<210> SEQ ID NO 12
<211> LENGTH: 127
<212> TYPE: PRT
<213> ORGANISM: Homo sapiens

<400> SEQUENCE: 12

Glu Val Gln Leu Leu Glu Ser Gly Gly Gly Leu Val Gln Pro Gly Gly
              5                  10                  15

Ser Leu Arg Leu Ser Cys Ala Ala Ser Gly Phe Thr Phe Ser Ser Tyr
         20                  25                  30

Ala Met Ser Trp Val Arg Gln Ala Pro Gly Lys Gly Leu Glu Trp Val
     35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Lys Pro Leu Tyr Tyr Tyr Asp Ala Pro Pro Leu Gly Tyr Asp
            100                 105                 110

Gly Phe Asp Ile Trp Gly Arg Gly Thr Met Val Thr Val Ser Ser
        115                 120                 125

<210> SEQ ID NO 13
<211> LENGTH: 5
<212> TYPE: PRT
<213> ORGANISM: Homo sapiens

<400> SEQUENCE: 13

Ser Tyr Ala Met Ser
              5

<210> SEQ ID NO 14
<211> LENGTH: 17
<212> TYPE: PRT
<213> ORGANISM: Homo sapiens

<400> SEQUENCE: 14

Ala Ile Ser Gly Ser Gly Gly Ser Thr Tyr Tyr Ala Asp Ser Val Lys
 1               5                  10                  15

Gly

<210> SEQ ID NO 15
<211> LENGTH: 18
<212> TYPE: PRT
<213> ORGANISM: Homo sapiens

<400> SEQUENCE: 15

Pro Leu Tyr Tyr Tyr Asp Ala Pro Pro Leu Gly Tyr Asp Gly Phe
 1               5                  10                  15

Asp Ile

<210> SEQ ID NO 16
<211> LENGTH: 333
<212> TYPE: DNA
<213> ORGANISM: Homo sapiens

<400> SEQUENCE: 16
cagtctgtgc tgacgcagcc gccctcagtg tctggggccc cagggcagag ggtcaccatc      60
tcctgcactg ggagcagctc aacatcgggg gcaggttatg atgtacactg gtaccagcag     120
cttccaggga cagcccccaa gctcctcatc tatggtgaca cccatcggcc ctcaggggtc     180
cctgaccgat tctctggctc caagtctggc acctcagcct ccctggtcat cgctgggctc     240
caggctgagg atgaggctga ttattactgc cagtcctatg acaccgcagg cggcggccac     300
catttcggcg gagggaccaa gctgaccgtc cta                                  333

<210> SEQ ID NO 17
<211> LENGTH: 111
<212> TYPE: PRT
<213> ORGANISM: Homo sapiens

<400> SEQUENCE: 17

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asp Thr His Arg Pro Ser Gly Val Pro Asp Arg Phe
        50                  55                  60

Ser Gly Ser Lys Ser Gly Thr Ser Ala Ser Leu Val Ile Ala Gly Leu
 65                 70                  75                  80

Gln Ala Glu Asp Glu Ala Asp Tyr Tyr Cys Gln Ser Tyr Asp Thr Ala
                85                  90                  95

Gly Gly Gly His His Phe Gly Gly Gly Thr Lys Leu Thr Val Leu
           100                 105                 110

<210> SEQ ID NO 18
<211> LENGTH: 14
<212> TYPE: PRT
<213> ORGANISM: Homo sapiens

<400> SEQUENCE: 18

Thr Gly Ser Ser Ser Asn Ile Gly Ala Gly Tyr Asp Val His
 1               5                  10

<210> SEQ ID NO 19

```
<211> LENGTH: 7
<212> TYPE: PRT
<213> ORGANISM: Homo sapiens

<400> SEQUENCE: 19

Gly Asp Thr His Arg Pro Ser
                5

<210> SEQ ID NO 20
<211> LENGTH: 11
<212> TYPE: PRT
<213> ORGANISM: Homo sapiens

<400> SEQUENCE: 20

Gln Ser Tyr Asp Thr Ala Gly Gly Gly His His
                5                   10

<210> SEQ ID NO 21
<211> LENGTH: 378
<212> TYPE: DNA
<213> ORGANISM: Homo sapiens

<400> SEQUENCE: 21
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gaaacccttg     300
tactactatg atgaacaata tggcgtagta tatgatgctt ttgtctgggg ccggggggaca    360 ctggtcaccg tctcctca                                                   378

<210> SEQ ID NO 22
<211> LENGTH: 126
<212> TYPE: PRT
<213> ORGANISM: Homo sapiens

<400> SEQUENCE: 22

Glu Val Gln Leu Leu Glu Ser Gly Gly Gly Leu Val Gln Pro Gly Gly
                5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Leu Tyr Tyr Tyr Asp Glu Gln Tyr Gly Val Val Tyr Asp
            100                 105                 110

Ala Phe Val Trp Gly Arg Gly Thr Leu Val Thr Val Ser Ser
        115                 120                 125

<210> SEQ ID NO 23
<211> LENGTH: 5
<212> TYPE: PRT
<213> ORGANISM: Homo sapiens
```

```
<400> SEQUENCE: 23

Ser Tyr Ala Met Ser
                5

<210> SEQ ID NO 24
<211> LENGTH: 17
<212> TYPE: PRT
<213> ORGANISM: Homo sapiens

<400> SEQUENCE: 24

Ala Ile Ser Gly Ser Gly Gly Ser Thr Tyr Tyr Ala Asp Ser Val Lys
                5                   10                  15

Gly

<210> SEQ ID NO 25
<211> LENGTH: 17
<212> TYPE: PRT
<213> ORGANISM: Homo sapiens

<400> SEQUENCE: 25

Pro Leu Tyr Tyr Tyr Asp Glu Gln Tyr Gly Val Val Tyr Asp Ala Phe
                5                   10                  15

Val

<210> SEQ ID NO 26
<211> LENGTH: 333
<212> TYPE: DNA
<213> ORGANISM: Homo sapiens

<400> SEQUENCE: 26
cagtctgtgc tgacgcagcc gccctcagtg tctggggccc cagggcagag ggtcaccatc      60
tcctgcactg ggagcagctc caacatcggg gcaggttatg atgtacactg gtaccagcag     120
cttccaggga cagcccccaa gctcctcatc tatggtgaca cccatcggcc ctcaggggtc     180
cctgaccgat tctctggctc caagtctggc acctcagcct ccctggccat cactgggctc     240
caggctgagg atgaggctga ttattactgc cagtcctatg acaccgtacg tctccaccat     300
gtgttcggcg gagggaccaa gctgaccgtc cta                                  333

<210> SEQ ID NO 27
<211> LENGTH: 111
<212> TYPE: PRT
<213> ORGANISM: Homo sapiens

<400> SEQUENCE: 27

Gln Ser Val Leu Thr Gln Pro Pro Ser Val Ser Gly Ala Pro Gly Gln
                5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asp Thr His Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Val
                85                  90                  95

Arg Leu His His Val Phe Gly Gly Gly Thr Lys Leu Thr Val Leu
            100                 105                 110
```

-continued

<210> SEQ ID NO 28
<211> LENGTH: 14
<212> TYPE: PRT
<213> ORGANISM: Homo sapiens

<400> SEQUENCE: 28

Thr Gly Ser Ser Ser Asn Ile Gly Ala Gly Tyr Asp Val His
                  5                   10

<210> SEQ ID NO 29
<211> LENGTH: 7
<212> TYPE: PRT
<213> ORGANISM: Homo sapiens

<400> SEQUENCE: 29

Gly Asp Thr His Arg Pro Ser
                  5

<210> SEQ ID NO 30
<211> LENGTH: 11
<212> TYPE: PRT
<213> ORGANISM: Homo sapiens

<400> SEQUENCE: 30

Gln Ser Tyr Asp Thr Val Arg Leu His His Val
                  5                   10

<210> SEQ ID NO 31
<211> LENGTH: 381
<212> TYPE: DNA
<213> ORGANISM: Homo sapiens

<400> SEQUENCE: 31
caggtgcagc tgttggagtc tgggggaggc ttggtacagc ctggggggtc cctgagactc     60
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggctgtgt attactgtgc gaaacccttg    300
tactactatg atgccgcacc gcccctgggc tatgatggtt ttgatatctg gggccggggg    360
acaatggtca ccgtctcctc a                                              381

<210> SEQ ID NO 32
<211> LENGTH: 127
<212> TYPE: PRT
<213> ORGANISM: Homo sapiens

<400> SEQUENCE: 32

Gln Val Gln Leu Leu Glu Ser Gly Gly Gly Leu Val Gln Pro Gly Gly
                  5                   10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

-continued

Ala Lys Pro Leu Tyr Tyr Tyr Asp Ala Ala Pro Pro Leu Gly Tyr Asp
            100                 105                 110

Gly Phe Asp Ile Trp Gly Arg Gly Thr Met Val Thr Val Ser Ser
            115                 120                 125

<210> SEQ ID NO 33
<211> LENGTH: 5
<212> TYPE: PRT
<213> ORGANISM: Homo sapiens

<400> SEQUENCE: 33

Ser Tyr Ala Met Ser
                5

<210> SEQ ID NO 34
<211> LENGTH: 17
<212> TYPE: PRT
<213> ORGANISM: Homo sapiens

<400> SEQUENCE: 34

Ala Ile Ser Gly Ser Gly Gly Ser Thr Tyr Tyr Ala Asp Ser Val Lys
                5                   10                  15

Gly

<210> SEQ ID NO 35
<211> LENGTH: 18
<212> TYPE: PRT
<213> ORGANISM: Homo sapiens

<400> SEQUENCE: 35

Pro Leu Tyr Tyr Tyr Asp Ala Ala Pro Pro Leu Gly Tyr Asp Gly Phe
                5                   10                  15

Asp Ile

<210> SEQ ID NO 36
<211> LENGTH: 333
<212> TYPE: DNA
<213> ORGANISM: Homo sapiens

<400> SEQUENCE: 36
cagtctgtgc tgacgcagcc gccctcagtg tctggggccc cagggcagag ggtcaccatc    60
tcctgcactg ggagcagctc aacatcgggg gcaggttatg atgtacactg gtaccagcag    120
cttccaggga cagccccaa gctcctcatc tatggtgaca cccatcggcc ctcaggggtt    180
cctgaccgat tctctggctc caagtctggc acctcagcct ccctggtcat cgctgggctc    240
caggctgagg atgaggctga ttattactgc cagtcctatg acaccgatgc cgcacgccac    300
cagttcggtg gagggaccaa gctgaccgtc cta                                 333

<210> SEQ ID NO 37
<211> LENGTH: 111
<212> TYPE: PRT
<213> ORGANISM: Homo sapiens

<400> SEQUENCE: 37

Gln Ser Val Leu Thr Gln Pro Pro Ser Val Ser Gly Ala Pro Gly Gln
                5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

```
Leu Ile Tyr Gly Asp Thr His Arg Pro Ser Gly Val Pro Asp Arg Phe
         50                  55                  60

Ser Gly Ser Lys Ser Gly Thr Ser Ala Ser Leu Val Ile Ala Gly Leu
 65                  70                  75                  80

Gln Ala Glu Asp Glu Ala Asp Tyr Tyr Cys Gln Ser Tyr Asp Thr Asp
                 85                  90                  95

Ala Ala Arg His Gln Phe Gly Gly Gly Thr Lys Leu Thr Val Leu
            100                 105                 110

<210> SEQ ID NO 38
<211> LENGTH: 14
<212> TYPE: PRT
<213> ORGANISM: Homo sapiens

<400> SEQUENCE: 38

Thr Gly Ser Ser Ser Asn Ile Gly Ala Gly Tyr Asp Val His
                  5                  10

<210> SEQ ID NO 39
<211> LENGTH: 7
<212> TYPE: PRT
<213> ORGANISM: Homo sapiens

<400> SEQUENCE: 39

Gly Asp Thr His Arg Pro Ser
                  5

<210> SEQ ID NO 40
<211> LENGTH: 11
<212> TYPE: PRT
<213> ORGANISM: Homo sapiens

<400> SEQUENCE: 40

Gln Ser Tyr Asp Thr Asp Ala Ala Arg His Gln
                  5                  10

<210> SEQ ID NO 41
<211> LENGTH: 381
<212> TYPE: DNA
<213> ORGANISM: Homo sapiens

<400> SEQUENCE: 41
gaggtgcagc tgttggagtc tgggggaggc ttggtacagc ctggggggtc cctgagactc      60
tcctgtgcag cctctggatt caccttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gaaacccttg     300
tactactatg atgcaccttc cccctaggg tatgatggtt ttgatatctg gggccggggg     360
acactggtca ccgtctcctc a                                              381

<210> SEQ ID NO 42
<211> LENGTH: 127
<212> TYPE: PRT
<213> ORGANISM: Homo sapiens

<400> SEQUENCE: 42

Glu Val Gln Leu Leu Glu Ser Gly Gly Gly Leu Val Gln Pro Gly Gly
                  5                  10                  15

Ser Leu Arg Leu Ser Cys Ala Ala Ser Gly Phe Thr Phe Ser Ser Tyr
```

```
                    20                  25                  30
Ala Met Ser Trp Val Arg Gln Ala Pro Gly Lys Gly Leu Glu Trp Val
                35                  40                  45
Ser Ala Ile Ser Gly Ser Gly Gly Ser Thr Tyr Tyr Ala Asp Ser Val
            50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Pro Leu Tyr Tyr Tyr Asp Ala Pro Ser Pro Leu Gly Tyr Asp
            100                 105                 110
Gly Phe Asp Ile Trp Gly Arg Gly Thr Leu Val Thr Val Ser Ser
            115                 120                 125

<210> SEQ ID NO 43
<211> LENGTH: 5
<212> TYPE: PRT
<213> ORGANISM: Homo sapiens

<400> SEQUENCE: 43

Ser Tyr Ala Met Ser
                5

<210> SEQ ID NO 44
<211> LENGTH: 17
<212> TYPE: PRT
<213> ORGANISM: Homo sapiens

<400> SEQUENCE: 44

Ala Ile Ser Gly Ser Gly Gly Ser Thr Tyr Tyr Ala Asp Ser Val Lys
                5                   10                  15
Gly

<210> SEQ ID NO 45
<211> LENGTH: 18
<212> TYPE: PRT
<213> ORGANISM: Homo sapiens

<400> SEQUENCE: 45

Pro Leu Tyr Tyr Tyr Asp Ala Pro Ser Pro Leu Gly Tyr Asp Gly Phe
                5                   10                  15
Asp Ile

<210> SEQ ID NO 46
<211> LENGTH: 333
<212> TYPE: DNA
<213> ORGANISM: Homo sapiens

<400> SEQUENCE: 46
cagtctgtgc tgacgcagcc gccctcagtg tctggggccc cagggcagag ggtcaccatc      60
tcctgcactg ggagcagctc caacatcggg gcaggttatg atgtacactg gtaccagcag     120
cttccaggga cagcccccaa gctcctcatc tatggtgaca cccatcggcc ctcagggatc     180
cctgaccgat tctctggctc caagtctggc acctcagcct ccctggccat cactgggctc     240
caggctgagg atgaggctga ttattactgc cagtcctatg acacccacct tgtcgcacac     300
gtgttcggcg agggaccaa gctgaccgtc cta                                    333

<210> SEQ ID NO 47
<211> LENGTH: 111
```

<212> TYPE: PRT
<213> ORGANISM: Homo sapiens

<400> SEQUENCE: 47

Gln Ser Val Leu Thr Gln Pro Pro Ser Val Gly Ala Pro Gly Gln
1               5                   10                  15
Arg Val Thr Ile Ser Cys Thr Gly Ser Ser Asn Ile Gly Ala Gly
                20                  25                  30
Tyr Asp Val His Trp Tyr Gln Gln Leu Pro Gly Thr Ala Pro Lys Leu
            35                  40                  45
Leu Ile Tyr Gly Asp Thr His Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Gln Ser Tyr Asp Thr His
                85                  90                  95
Leu Val Ala His Val Phe Gly Gly Gly Thr Lys Leu Thr Val Leu
            100                 105                 110

<210> SEQ ID NO 48
<211> LENGTH: 14
<212> TYPE: PRT
<213> ORGANISM: Homo sapiens

<400> SEQUENCE: 48

Thr Gly Ser Ser Ser Asn Ile Gly Ala Gly Tyr Asp Val His
1               5                   10

<210> SEQ ID NO 49
<211> LENGTH: 7
<212> TYPE: PRT
<213> ORGANISM: Homo sapiens

<400> SEQUENCE: 49

Gly Asp Thr His Arg Pro Ser
1               5

<210> SEQ ID NO 50
<211> LENGTH: 11
<212> TYPE: PRT
<213> ORGANISM: Homo sapiens

<400> SEQUENCE: 50

Gln Ser Tyr Asp Thr His Leu Val Ala His Val
1               5                   10

<210> SEQ ID NO 51
<211> LENGTH: 381
<212> TYPE: DNA
<213> ORGANISM: Homo sapiens

<400> SEQUENCE: 51
gaggtgcagc tgttggagtc tgggggaggc ttggtacagc ctgggggtc cctgagactc      60
tcctgtgcag cctctggatt cacctttagc agctatgcca tgagctgggt ccgccaggct    120
ccagggaagg gctggagtg gtctcagct attagtggta gtggtggtag cacatactac     180
gcagactccg tgaagggccg gttcaccatc tccagagaca attccaagaa cacgctgtat    240
ctgcaaatga acagcctgag agccgaggac acggccgtgt attactgtgc gaaacccttg    300
tactactatg atgagcagta tggactagta tatgatgctt ttgatatcgg gggccggggg    360
acactggtca ccgtctcctc a                                              381

<210> SEQ ID NO 52
<211> LENGTH: 127
<212> TYPE: PRT
<213> ORGANISM: Homo sapiens

<400> SEQUENCE: 52

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Leu Tyr Tyr Tyr Asp Glu Gln Tyr Gly Leu Val Tyr Asp
            100                 105                 110

Ala Phe Asp Ile Gly Gly Arg Gly Thr Leu Val Thr Val Ser Ser
        115                 120                 125

<210> SEQ ID NO 53
<211> LENGTH: 5
<212> TYPE: PRT
<213> ORGANISM: Homo sapiens

<400> SEQUENCE: 53

Ser Tyr Ala Met Ser
 1               5

<210> SEQ ID NO 54
<211> LENGTH: 17
<212> TYPE: PRT
<213> ORGANISM: Homo sapiens

<400> SEQUENCE: 54

Ala Ile Ser Gly Ser Gly Gly Ser Thr Tyr Tyr Ala Asp Ser Val Lys
 1               5                  10                  15

Gly

<210> SEQ ID NO 55
<211> LENGTH: 18
<212> TYPE: PRT
<213> ORGANISM: Homo sapiens

<400> SEQUENCE: 55

Pro Leu Tyr Tyr Tyr Asp Glu Gln Tyr Gly Leu Val Tyr Asp Ala Phe
 1               5                  10                  15

Asp Ile

<210> SEQ ID NO 56
<211> LENGTH: 333
<212> TYPE: DNA
<213> ORGANISM: Homo sapiens

<400> SEQUENCE: 56
cagtctgtgc tgacgcagcc gccctcagtg tctggggccc cagggcagag ggtcaccatc    60

```
tcctgcactg ggagcagctc caacatcggg gcaggttatg atgtacactg gtaccagcag    120
cttccaggga cagcccccaa gctcctcatc tatggtgaca cccatcggcc ctcaggggtc    180
cctgaccgat tctctggctc caagtctggc acctcagcct ccctggccat cactgggctc    240
caggctgagg atgaggctga ttattactgc cagtcctatg acaccctact tctcgcacca    300
caattcggcg gagggaccaa gctgaccgtc cta                                 333
```

<210> SEQ ID NO 57
<211> LENGTH: 111
<212> TYPE: PRT
<213> ORGANISM: Homo sapiens

<400> SEQUENCE: 57

Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asp Thr His Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Leu
                85                  90                  95

Leu Leu Ala Pro Gln Phe Gly Gly Thr Lys Leu Thr Val Leu
            100                 105                 110

<210> SEQ ID NO 58
<211> LENGTH: 14
<212> TYPE: PRT
<213> ORGANISM: Homo sapiens

<400> SEQUENCE: 58

Thr Gly Ser Ser Ser Asn Ile Gly Ala Gly Tyr Asp Val His
1               5                   10

<210> SEQ ID NO 59
<211> LENGTH: 7
<212> TYPE: PRT
<213> ORGANISM: Homo sapiens

<400> SEQUENCE: 59

Gly Asp Thr His Arg Pro Ser
1               5

<210> SEQ ID NO 60
<211> LENGTH: 11
<212> TYPE: PRT
<213> ORGANISM: Homo sapiens

<400> SEQUENCE: 60

Gln Ser Tyr Asp Thr Leu Leu Leu Ala Pro Gln
1               5                   10

<210> SEQ ID NO 61
<211> LENGTH: 378
<212> TYPE: DNA
<213> ORGANISM: Homo sapiens

<400> SEQUENCE: 61

```
gaggtgcagc tgttggagtc tggggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gaaacccttg     300
tactactatg atgaacaata tggcgtagta tatgatgctt ttgtctgggg ccggggggaca     360 atggtcaccg tctcctca                                                   378
```

<210> SEQ ID NO 62
<211> LENGTH: 126
<212> TYPE: PRT
<213> ORGANISM: Homo sapiens

<400> SEQUENCE: 62

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Leu Tyr Tyr Tyr Asp Glu Gln Tyr Gly Val Val Tyr Asp
            100                 105                 110

Ala Phe Val Trp Gly Arg Gly Thr Met Val Thr Val Ser Ser
        115                 120                 125

<210> SEQ ID NO 63
<211> LENGTH: 5
<212> TYPE: PRT
<213> ORGANISM: Homo sapiens

<400> SEQUENCE: 63

Ser Tyr Ala Met Ser
                 5

<210> SEQ ID NO 64
<211> LENGTH: 17
<212> TYPE: PRT
<213> ORGANISM: Homo sapiens

<400> SEQUENCE: 64

Ala Ile Ser Gly Ser Gly Gly Ser Thr Tyr Tyr Ala Asp Ser Val Lys
                 5                  10                  15

Gly

<210> SEQ ID NO 65
<211> LENGTH: 17
<212> TYPE: PRT
<213> ORGANISM: Homo sapiens

<400> SEQUENCE: 65

Pro Leu Tyr Tyr Tyr Asp Glu Gln Tyr Gly Val Val Tyr Asp Ala Phe
                 5                  10                  15

Val

<210> SEQ ID NO 66
<211> LENGTH: 333
<212> TYPE: DNA
<213> ORGANISM: Homo sapiens

<400> SEQUENCE: 66

```
cagtctgtgc tgacgcagcc gccctcagtg tctggggccc cagggcagag ggtcaccatc      60
tcctgcactg ggagcagctc caacatcggg gcaggttatg atgtacactg gtaccagcag     120
cttccaggga cagcccccaa gctcctcatc tatggtgaca cccatcggcc ctcagggatc     180
cctgaccgat tctctggctc caagtccggc acctcagcct ccctggtcat cgctgggctc     240
caggctgagg atgaggctga ttattactgc cagtcctatg acaccgtacg tctccaccat     300
gtgttcggcg gagggaccaa gctgaccgtc cta                                  333
```

<210> SEQ ID NO 67
<211> LENGTH: 111
<212> TYPE: PRT
<213> ORGANISM: Homo sapiens

<400> SEQUENCE: 67

Gln Ser Val Leu Thr Gln Pro Pro Ser Val Ser Gly Ala Pro Gly Gln
             5               10             15

Arg Val Thr Ile Ser Cys Thr Gly Ser Ser Asn Ile Gly Ala Gly
         20              25             30

Tyr Asp Val His Trp Tyr Gln Gln Leu Pro Gly Thr Ala Pro Lys Leu
             35             40             45

Leu Ile Tyr Gly Asp Thr His Arg Pro Ser Gly Val Pro Asp Arg Phe
 50              55             60

Ser Gly Ser Lys Ser Gly Thr Ser Ala Ser Leu Val Ile Ala Gly Leu
65              70             75             80

Gln Ala Glu Asp Glu Ala Asp Tyr Tyr Cys Gln Ser Tyr Asp Thr Val
             85             90             95

Arg Leu His His Val Phe Gly Gly Gly Thr Lys Leu Thr Val Leu
        100            105           110

<210> SEQ ID NO 68
<211> LENGTH: 14
<212> TYPE: PRT
<213> ORGANISM: Homo sapiens

<400> SEQUENCE: 68

Thr Gly Ser Ser Ser Asn Ile Gly Ala Gly Tyr Asp Val His
             5               10

<210> SEQ ID NO 69
<211> LENGTH: 7
<212> TYPE: PRT
<213> ORGANISM: Homo sapiens

<400> SEQUENCE: 69

Gly Asp Thr His Arg Pro Ser
             5

<210> SEQ ID NO 70
<211> LENGTH: 11
<212> TYPE: PRT
<213> ORGANISM: Homo sapiens

<400> SEQUENCE: 70

Gln Ser Tyr Asp Thr Val Arg Leu His His Val
                5                  10

<210> SEQ ID NO 71
<211> LENGTH: 381
<212> TYPE: DNA
<213> ORGANISM: Homo sapiens

<400> SEQUENCE: 71
caggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggccgtgt attactgtgc gaaacccttg    300
tactactatg atgccccttc cccctaggc tatgatggtt ttgatatctg gggccgggg     360 acaatggtca ccgtctcgag t                                               381

<210> SEQ ID NO 72
<211> LENGTH: 127
<212> TYPE: PRT
<213> ORGANISM: Homo sapiens

<400> SEQUENCE: 72

Gln Val Gln Leu Leu Glu Ser Gly Gly Gly Leu Val Gln Pro Gly Gly
                5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Leu Tyr Tyr Tyr Asp Ala Pro Ser Pro Leu Gly Tyr Asp
            100                 105                 110

Gly Phe Asp Ile Trp Gly Arg Gly Thr Met Val Thr Val Ser Ser
        115                 120                 125

<210> SEQ ID NO 73
<211> LENGTH: 5
<212> TYPE: PRT
<213> ORGANISM: Homo sapiens

<400> SEQUENCE: 73

Ser Tyr Ala Met Ser
                5

<210> SEQ ID NO 74
<211> LENGTH: 17
<212> TYPE: PRT
<213> ORGANISM: Homo sapiens

<400> SEQUENCE: 74

Ala Ile Ser Gly Ser Gly Gly Ser Thr Tyr Tyr Ala Asp Ser Val Lys
                5                  10                  15

Gly

<210> SEQ ID NO 75
<211> LENGTH: 18
<212> TYPE: PRT
<213> ORGANISM: Homo sapiens

<400> SEQUENCE: 75

Pro Leu Tyr Tyr Tyr Asp Ala Pro Ser Pro Leu Gly Tyr Asp Gly Phe
1               5                   10                  15

Asp Ile

<210> SEQ ID NO 76
<211> LENGTH: 333
<212> TYPE: DNA
<213> ORGANISM: Homo sapiens

<400> SEQUENCE: 76
cagtctgtgc tgacgcagcc gccctcagtg tctggggccc cagggcagag agtcaccatc      60
tcctgcactg ggagcagctc caacatcggg gcaggttatg atgtacactg gtaccagcag     120
cttccaggga cagcccccaa gctcctcatc tatggtgaca cccatcggcc ctcaggggtc     180
cctgaccgat tctctggctc caagtctggc acctcagcct ccctggtcat cgctgggctc     240
caggctgagg atgaggctga ttattactgc cagtcctatg acacccacct tgtcgcacac     300
gtgttcggcg gagggaccaa gctgaccgtc cta                                  333

<210> SEQ ID NO 77
<211> LENGTH: 111
<212> TYPE: PRT
<213> ORGANISM: Homo sapiens

<400> SEQUENCE: 77

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asp Thr His Arg Pro Ser Gly Val Pro Asp Arg Phe
    50                  55                  60

Ser Gly Ser Lys Ser Gly Thr Ser Ala Ser Leu Val Ile Ala Gly Leu
65                  70                  75                  80

Gln Ala Glu Asp Glu Ala Asp Tyr Tyr Cys Gln Ser Tyr Asp Thr His
                85                  90                  95

Leu Val Ala His Val Phe Gly Gly Gly Thr Lys Leu Thr Val Leu
            100                 105                 110

<210> SEQ ID NO 78
<211> LENGTH: 14
<212> TYPE: PRT
<213> ORGANISM: Homo sapiens

<400> SEQUENCE: 78

Thr Gly Ser Ser Ser Asn Ile Gly Ala Gly Tyr Asp Val His
1               5                   10

<210> SEQ ID NO 79
<211> LENGTH: 7
<212> TYPE: PRT

<213> ORGANISM: Homo sapiens

<400> SEQUENCE: 79

Gly Asp Thr His Arg Pro Ser
                5

<210> SEQ ID NO 80
<211> LENGTH: 11
<212> TYPE: PRT
<213> ORGANISM: Homo sapiens

<400> SEQUENCE: 80

Gln Ser Tyr Asp Thr His Leu Val Ala His Val
                5                   10

<210> SEQ ID NO 81
<211> LENGTH: 381
<212> TYPE: DNA
<213> ORGANISM: Homo sapiens

<400> SEQUENCE: 81
gaggtgcagc tgttggagtc tgggggaggc ttggtacagc ctgggggtc cctgagactc      60 tcctgtgcag cctctggatt caccttagc agctatgcca tgagctgggt ccgccaggct     120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gaaacccttg    300
tactactatg atgaatcact agctctacct gtgtatgatg ctgatatctg gggccggggg    360
acactggtca ccgtctcctc a                                              381

<210> SEQ ID NO 82
<211> LENGTH: 127
<212> TYPE: PRT
<213> ORGANISM: Homo sapiens

<400> SEQUENCE: 82

Glu Val Gln Leu Leu Glu Ser Gly Gly Gly Leu Val Gln Pro Gly Gly
                5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Leu Tyr Tyr Tyr Asp Glu Ser Leu Ala Leu Pro Val Tyr
            100                 105                 110

Asp Ala Asp Ile Trp Gly Arg Gly Thr Leu Val Thr Val Ser Ser
        115                 120                 125

<210> SEQ ID NO 83
<211> LENGTH: 5
<212> TYPE: PRT
<213> ORGANISM: Homo sapiens

<400> SEQUENCE: 83

```
<210> SEQ ID NO 84
<211> LENGTH: 17
<212> TYPE: PRT
<213> ORGANISM: Homo sapiens

<400> SEQUENCE: 84

Ala Ile Ser Gly Ser Gly Gly Ser Thr Tyr Tyr Ala Asp Ser Val Lys
                5                   10                  15
Gly

<210> SEQ ID NO 85
<211> LENGTH: 18
<212> TYPE: PRT
<213> ORGANISM: Homo sapiens

<400> SEQUENCE: 85

Pro Leu Tyr Tyr Tyr Asp Glu Ser Leu Ala Leu Pro Val Tyr Asp Ala
                5                   10                  15
Asp Ile

<210> SEQ ID NO 86
<211> LENGTH: 333
<212> TYPE: DNA
<213> ORGANISM: Homo sapiens

<400> SEQUENCE: 86
cagtctgtgc tgacgcagcc gccctcagtg tctggggccc cagggcagag ggtcaccatc    60
tcctgcactg ggagcagctc caacatcggg gcaggttatg atgtacactg gtaccagcag   120
cttccaggga cagcccccaa gctcctcatc tatggtgaca cccatcggcc ctcaggggtc   180
cctgaccgat tctctggctc caagtctggc acctcagcct ccctggccat cactgggctc   240
caggctgagg atgaggctga ttattactgc cagtcctatg acacccgagc cgacgatgct   300
cacttcggcg gaggaaccaa gctgaccgtc cta                                333

<210> SEQ ID NO 87
<211> LENGTH: 111
<212> TYPE: PRT
<213> ORGANISM: Homo sapiens

<400> SEQUENCE: 87

Gln Ser Val Leu Thr Gln Pro Pro Ser Val Ser Gly Ala Pro Gly Gln
                5                   10                  15
Arg Val Thr Ile Ser Cys Thr Gly Ser Ser Ser Asn Ile Gly Ala Gly
            20                  25                  30
Tyr Asp Val His Trp Tyr Gln Gln Leu Pro Gly Thr Ala Pro Lys Leu
        35                  40                  45
Leu Ile Tyr Gly Asp Thr His Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Gln Ser Tyr Asp Thr Arg
                85                  90                  95
Ala Asp Asp Ala His Phe Gly Gly Gly Thr Lys Leu Thr Val Leu
            100                 105                 110

<210> SEQ ID NO 88
```

```
<211> LENGTH: 14
<212> TYPE: PRT
<213> ORGANISM: Homo sapiens

<400> SEQUENCE: 88

Thr Gly Ser Ser Ser Asn Ile Gly Ala Gly Tyr Asp Val His
                 5                  10

<210> SEQ ID NO 89
<211> LENGTH: 7
<212> TYPE: PRT
<213> ORGANISM: Homo sapiens

<400> SEQUENCE: 89

Gly Asp Thr His Arg Pro Ser
                 5

<210> SEQ ID NO 90
<211> LENGTH: 11
<212> TYPE: PRT
<213> ORGANISM: Homo sapiens

<400> SEQUENCE: 90

Gln Ser Tyr Asp Thr Arg Ala Asp Asp Ala His
                 5                  10

<210> SEQ ID NO 91
<211> LENGTH: 378
<212> TYPE: DNA
<213> ORGANISM: Homo sapiens

<400> SEQUENCE: 91
gaggtgcagc tgttggagtc tgggggaggc ttggtacagc ctgggggttc cctgagactc       60
tcctgtgcag cctctggatt cacctttagc agctatgcca tgagctgggt ccgccaggct      120
ccagggaagg gctggagtg gtctcagct attagtggta gtggtggtag cacatactac        180
gcagactccg tgaagggccg gttcaccatc tccagagaca attccaagaa cacgctgtat      240
ctgcaaatga acagcctgag agccgaggac acggccgtgt attactgtgc aagagatggc      300
gcgagtagta ccaattgggg atacaactac tacggtatgg acgtctgggg cgggggacc      360 acggtcaccg tctcctca                                                    378

<210> SEQ ID NO 92
<211> LENGTH: 126
<212> TYPE: PRT
<213> ORGANISM: Homo sapiens

<400> SEQUENCE: 92

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ala Ser Ser Thr Asn Trp Gly Tyr Asn Tyr Tyr Gly
```

```
                100                 105                 110
Met Asp Val Trp Gly Arg Gly Thr Val Thr Val Ser Ser
            115                 120                 125

<210> SEQ ID NO 93
<211> LENGTH: 5
<212> TYPE: PRT
<213> ORGANISM: Homo sapiens

<400> SEQUENCE: 93

Ser Tyr Ala Met Ser
                5

<210> SEQ ID NO 94
<211> LENGTH: 17
<212> TYPE: PRT
<213> ORGANISM: Homo sapiens

<400> SEQUENCE: 94

Ala Ile Ser Gly Ser Gly Gly Ser Thr Tyr Tyr Ala Asp Ser Val Lys
                5                  10                  15

Gly

<210> SEQ ID NO 95
<211> LENGTH: 17
<212> TYPE: PRT
<213> ORGANISM: Homo sapiens

<400> SEQUENCE: 95

Asp Gly Ala Ser Ser Thr Asn Trp Gly Tyr Asn Tyr Gly Met Asp
                5                  10                  15

Val

<210> SEQ ID NO 96
<211> LENGTH: 330
<212> TYPE: DNA
<213> ORGANISM: Homo sapiens

<400> SEQUENCE: 96
caggctgtgc tgactcagcc gtcctcagcg tctgggaccc ccgggcagag ggtcaccatc      60
tcttgttctg gcagcagctc aacatcgga agtaattatg tattctggta ccagcagttc     120
ccaggtacgg cccccccaact cctcgtcaaa tggaataatc agcggccctc aggggtccct    180
gaccgattct ctggctccaa gtctggcacc tcagcctccc tggccatcag tggactccgg    240
tccgaggatg aggctgatta ttactgtgca gcatgggatg acagcctgag tggtctggta    300
ttcggcggag ggaccaagct gaccgtccta                                      330

<210> SEQ ID NO 97
<211> LENGTH: 110
<212> TYPE: PRT
<213> ORGANISM: Homo sapiens

<400> SEQUENCE: 97

Gln Ala Val Leu Thr Gln Pro Ser Ser Ala Ser Gly Thr Pro Gly Gln
                5                  10                  15

Arg Val Thr Ile Ser Cys Ser Gly Ser Ser Ser Asn Ile Gly Ser Asn
            20                  25                  30

Tyr Val Phe Trp Tyr Gln Gln Phe Pro Gly Thr Ala Pro Gln Leu Leu
        35                  40                  45

Val Lys Trp Asn Asn Gln Arg Pro Ser Gly Val Pro Asp Arg Phe Ser
```

```
                50                  55                  60
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Leu Val Phe Gly Gly Gly Thr Lys Leu Thr Val Leu
            100                 105                 110

<210> SEQ ID NO 98
<211> LENGTH: 13
<212> TYPE: PRT
<213> ORGANISM: Homo sapiens

<400> SEQUENCE: 98

Ser Gly Ser Ser Ser Asn Ile Gly Ser Asn Tyr Val Phe
                  5                  10

<210> SEQ ID NO 99
<211> LENGTH: 7
<212> TYPE: PRT
<213> ORGANISM: Homo sapiens

<400> SEQUENCE: 99

Trp Asn Asn Gln Arg Pro Ser
                  5

<210> SEQ ID NO 100
<211> LENGTH: 11
<212> TYPE: PRT
<213> ORGANISM: Homo sapiens

<400> SEQUENCE: 100

Ala Ala Trp Asp Asp Ser Leu Ser Gly Leu Val
                  5                  10

<210> SEQ ID NO 101
<211> LENGTH: 381
<212> TYPE: DNA
<213> ORGANISM: Homo sapiens

<400> SEQUENCE: 101
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg gctggagtg gtctcagct attagtggta gtggtggtag cacatactac      180
gcagactccg tgaagggccg gttcaccatc tccagagaca attccaagaa cacgctgtat     240
ctgcaaatga acagcctgag agccgaggac acggccgtgt attactgtgc gaaacccttg     300
tactactatg atggtagtga ttatacgact tatgatgctt ttgatatctg gggccggggg     360
acaatggtca ccgtctcctc a                                               381

<210> SEQ ID NO 102
<211> LENGTH: 127
<212> TYPE: PRT
<213> ORGANISM: Homo sapiens

<400> SEQUENCE: 102

Glu Val Gln Leu Leu Glu Ser Gly Gly Gly Leu Val Gln Pro Gly Gly
                  5                  10                  15

Ser Leu Arg Leu Ser Cys Ala Ala Ser Gly Phe Thr Phe Ser Ser Tyr
             20                  25                  30
```

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Leu Tyr Tyr Tyr Asp Gly Ser Asp Tyr Thr Thr Tyr Asp
             100                 105                 110

Ala Phe Asp Ile Trp Gly Arg Gly Thr Met Val Thr Val Ser Ser
         115                 120                 125

<210> SEQ ID NO 103
<211> LENGTH: 5
<212> TYPE: PRT
<213> ORGANISM: Homo sapiens

<400> SEQUENCE: 103

Ser Tyr Ala Met Ser
             5

<210> SEQ ID NO 104
<211> LENGTH: 17
<212> TYPE: PRT
<213> ORGANISM: Homo sapiens

<400> SEQUENCE: 104

Ala Ile Ser Gly Ser Gly Gly Ser Thr Tyr Tyr Ala Asp Ser Val Lys
             5                   10                  15

Gly

<210> SEQ ID NO 105
<211> LENGTH: 18
<212> TYPE: PRT
<213> ORGANISM: Homo sapiens

<400> SEQUENCE: 105

Pro Leu Tyr Tyr Tyr Asp Gly Ser Asp Tyr Thr Thr Tyr Asp Ala Phe
             5                   10                  15

Asp Ile

<210> SEQ ID NO 106
<211> LENGTH: 333
<212> TYPE: DNA
<213> ORGANISM: Homo sapiens

<400> SEQUENCE: 106
cagtctgtgc tgacgcagcc gccctcagtg tctggggccc cagggcagag ggtcaccatc    60
tcctgcactg ggagcagctc caacatcggg gcaggttatg atgtacactg gtaccagcag   120
cttccaggga cagcccccaa gctcctcatc tatggtgaca cccatcggcc ctcaggggtc   180
cctgaccgat tctctggctc caagtctggc acctcagcct ccctggtcat cgctgggctc   240
caggctgagg atgaggctga ttattactgc cagtcctatg acaccagcct gagtggttcg   300
ctgttcggcg gagggaccaa gctgaccgtc cta                                333

<210> SEQ ID NO 107
<211> LENGTH: 111
<212> TYPE: PRT
<213> ORGANISM: Homo sapiens

<400> SEQUENCE: 107

Gln Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ala Gly
            20                  25                  30
Tyr Asp Val His Trp Tyr Gln Gln Leu Pro Gly Thr Ala Pro Lys Leu
        35                  40                  45
Leu Ile Tyr Gly Asp Thr His Arg Pro Ser Gly Val Pro Asp Arg Phe
    50                  55                  60
Ser Gly Ser Lys Ser Gly Thr Ser Ala Ser Leu Val Ile Ala Gly Leu
65                  70                  75                  80
Gln Ala Glu Asp Glu Ala Asp Tyr Tyr Cys Gln Ser Tyr Asp Thr Ser
                85                  90                  95
Leu Ser Gly Ser Leu Phe Gly Gly Gly Thr Lys Leu Thr Val Leu
            100                 105                 110

<210> SEQ ID NO 108
<211> LENGTH: 14
<212> TYPE: PRT
<213> ORGANISM: Homo sapiens

<400> SEQUENCE: 108

Thr Gly Ser Ser Ser Asn Ile Gly Ala Gly Tyr Asp Val His
1               5                   10

<210> SEQ ID NO 109
<211> LENGTH: 7
<212> TYPE: PRT
<213> ORGANISM: Homo sapiens

<400> SEQUENCE: 109

Gly Asp Thr His Arg Pro Ser
1               5

<210> SEQ ID NO 110
<211> LENGTH: 11
<212> TYPE: PRT
<213> ORGANISM: Homo sapiens

<400> SEQUENCE: 110

Gln Ser Tyr Asp Thr Ser Leu Ser Gly Ser Leu
1               5                   10

<210> SEQ ID NO 111
<211> LENGTH: 381
<212> TYPE: DNA
<213> ORGANISM: Homo sapiens

<400> SEQUENCE: 111
caggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gaaacccttg     300
tactactatg atgagcagta tggactagta tatgatgctt ttgatatcgg gggccggggg     360
acaatggtca ccgtctcgag t                                                381

```
<210> SEQ ID NO 112
<211> LENGTH: 127
<212> TYPE: PRT
<213> ORGANISM: Homo sapiens

<400> SEQUENCE: 112

Gln Val Gln Leu Leu Glu Ser Gly Gly Gly Leu Val Gln Pro Gly Gly
                 5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Leu Tyr Tyr Tyr Asp Glu Gln Tyr Gly Leu Val Tyr Asp
            100                 105                 110

Ala Phe Asp Ile Gly Gly Arg Gly Thr Met Val Thr Val Ser Ser
        115                 120                 125

<210> SEQ ID NO 113
<211> LENGTH: 5
<212> TYPE: PRT
<213> ORGANISM: Homo sapiens

<400> SEQUENCE: 113

Ser Tyr Ala Met Ser
                 5

<210> SEQ ID NO 114
<211> LENGTH: 17
<212> TYPE: PRT
<213> ORGANISM: Homo sapiens

<400> SEQUENCE: 114

Ala Ile Ser Gly Ser Gly Gly Ser Thr Tyr Tyr Ala Asp Ser Val Lys
                 5                  10                  15

Gly

<210> SEQ ID NO 115
<211> LENGTH: 18
<212> TYPE: PRT
<213> ORGANISM: Homo sapiens

<400> SEQUENCE: 115

Pro Leu Tyr Tyr Tyr Asp Glu Gln Tyr Gly Leu Val Tyr Asp Ala Phe
                 5                  10                  15

Asp Ile

<210> SEQ ID NO 116
<211> LENGTH: 333
<212> TYPE: DNA
<213> ORGANISM: Homo sapiens

<400> SEQUENCE: 116
cagtctgtgc tgacgcagcc gccctcagtg tctggggccc cagggcagag agtcaccatc      60
tcctgcactg ggagcagctc caacatcggg gcaggttatg atgtacactg gtaccagcag     120
```

```
cttccaggga cagcccccaa gctcctcatc tatggtgaca cccatcggcc ctcaggggtc      180
cctgaccgat tctctggctc caagtctggc acctcagcct ccctggtcat cgctgggctc      240
caggctgagg atgaggctga ttattactgc cagtcctatg acaccctact tctcgcacca      300
caattcggcg agggaccaa gctgaccgtc cta                                    333
```

<210> SEQ ID NO 117
<211> LENGTH: 111
<212> TYPE: PRT
<213> ORGANISM: Homo sapiens
<400> SEQUENCE: 117

```
Gln Ser Val Leu Thr Gln Pro Pro Ser Val Ser Gly Ala Pro Gly Gln
              5                  10                  15
Arg Val Thr Ile Ser Cys Thr Gly Ser Ser Ser Asn Ile Gly Ala Gly
         20                  25                  30
Tyr Asp Val His Trp Tyr Gln Gln Leu Pro Gly Thr Ala Pro Lys Leu
     35                  40                  45
Leu Ile Tyr Gly Asp Thr His Arg Pro Ser Gly Val Pro Asp Arg Phe
 50                  55                  60
Ser Gly Ser Lys Ser Gly Thr Ser Ala Ser Leu Val Ile Ala Gly Leu
65                  70                  75                  80
Gln Ala Glu Asp Glu Ala Asp Tyr Tyr Cys Gln Ser Tyr Asp Thr Leu
                 85                  90                  95
Leu Leu Ala Pro Gln Phe Gly Gly Gly Thr Lys Leu Thr Val Leu
            100                 105                 110
```

<210> SEQ ID NO 118
<211> LENGTH: 14
<212> TYPE: PRT
<213> ORGANISM: Homo sapiens
<400> SEQUENCE: 118

```
Thr Gly Ser Ser Ser Asn Ile Gly Ala Gly Tyr Asp Val His
              5                  10
```

<210> SEQ ID NO 119
<211> LENGTH: 7
<212> TYPE: PRT
<213> ORGANISM: Homo sapiens
<400> SEQUENCE: 119

```
Gly Asp Thr His Arg Pro Ser
              5
```

<210> SEQ ID NO 120
<211> LENGTH: 11
<212> TYPE: PRT
<213> ORGANISM: Homo sapiens
<400> SEQUENCE: 120

```
Gln Ser Tyr Asp Thr Leu Leu Leu Ala Pro Gln
              5                  10
```

<210> SEQ ID NO 121
<211> LENGTH: 378
<212> TYPE: DNA
<213> ORGANISM: Homo sapiens
<400> SEQUENCE: 121

```
gaggtgcagc tgttggagtc tgggggaggc ttggtacagc ctggggggtc cctgagactc      60
```

```
tcctgtgcag cctctggatt cacctttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc aagagatggc    300
gcgagtagta ccaattgggg atacaccctg gacccgcctg gcgtgtgggg cgggggacc     360 acggtcaccg tctcctca                                                  378
```

<210> SEQ ID NO 122
<211> LENGTH: 126
<212> TYPE: PRT
<213> ORGANISM: Homo sapiens

<400> SEQUENCE: 122

Glu Val Gln Leu Leu Glu Ser Gly Gly Gly Leu Val Gln Pro Gly Gly
                 5                  10                  15
Ser Leu Arg Leu Ser Cys Ala Ala Ser Gly Phe Thr Phe Ser Ser Tyr
             20                  25                  30
Ala Met Ser Trp Val Arg Gln Ala Pro Gly Lys Gly Leu Glu Trp Val
         35                  40                  45
Ser Ala Ile Ser Gly Ser Gly Gly Ser Thr Tyr Tyr Ala Asp Ser Val
     50                  55                  60
Lys Gly Arg Phe Thr Ile Ser Arg Asp Asn Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Asp Gly Ala Ser Ser Thr Asn Trp Gly Tyr Thr Leu Asp Pro
            100                 105                 110
Pro Gly Val Trp Gly Arg Gly Thr Thr Val Thr Val Ser Ser
        115                 120                 125

<210> SEQ ID NO 123
<211> LENGTH: 5
<212> TYPE: PRT
<213> ORGANISM: Homo sapiens

<400> SEQUENCE: 123

Ser Tyr Ala Met Ser
                 5

<210> SEQ ID NO 124
<211> LENGTH: 17
<212> TYPE: PRT
<213> ORGANISM: Homo sapiens

<400> SEQUENCE: 124

Ala Ile Ser Gly Ser Gly Gly Ser Thr Tyr Tyr Ala Asp Ser Val Lys
                 5                  10                  15
Gly

<210> SEQ ID NO 125
<211> LENGTH: 17
<212> TYPE: PRT
<213> ORGANISM: Homo sapiens

<400> SEQUENCE: 125

Asp Gly Ala Ser Ser Thr Asn Trp Gly Tyr Thr Leu Asp Pro Pro Gly
                 5                  10                  15
Val

<210> SEQ ID NO 126
<211> LENGTH: 330
<212> TYPE: DNA
<213> ORGANISM: Homo sapiens

<400> SEQUENCE: 126

```
caggctgtgc tgactcagcc gtcctcagcg tctgggaccc ccgggcagag ggtcaccatc      60
tcttgttctg gcagcagctc caacatcgga agtaattatg tattctggta ccagcagttc     120
ccaggtacgg cccccaact cctcgtcaaa tggaataatc agcggccctc agggtccct       180
gaccgattct ctggctccaa gtctggcacc tcagcctccc tggccatcag tggactccgg     240
tccgaggatg aggctgatta ttactgtgca gcatgggatg acgccgctcg cgtactgctg     300
ttcggcggag ggaccaagct gaccgtccta                                      330
```

<210> SEQ ID NO 127
<211> LENGTH: 110
<212> TYPE: PRT
<213> ORGANISM: Homo sapiens

<400> SEQUENCE: 127

Gln Ala Val Leu Thr Gln Pro Ser Ser Ala Ser Gly Thr Pro Gly Gln
                5                   10                  15
Arg Val Thr Ile Ser Cys Ser Gly Ser Ser Asn Ile Gly Ser Asn
            20                  25                  30
Tyr Val Phe Trp Tyr Gln Gln Phe Pro Gly Thr Ala Pro Gln Leu Leu
        35                  40                  45
Val Lys Trp Asn Asn Gln Arg Pro Ser Gly Val Pro Asp Arg Phe Ser
    50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Ala Ala Trp Asp Asp Ala Ala
                85                  90                  95
Arg Val Leu Leu Phe Gly Gly Gly Thr Lys Leu Thr Val Leu
            100                 105                 110

<210> SEQ ID NO 128
<211> LENGTH: 13
<212> TYPE: PRT
<213> ORGANISM: Homo sapiens

<400> SEQUENCE: 128

Ser Gly Ser Ser Ser Asn Ile Gly Ser Asn Tyr Val Phe
                5                   10

<210> SEQ ID NO 129
<211> LENGTH: 7
<212> TYPE: PRT
<213> ORGANISM: Homo sapiens

<400> SEQUENCE: 129

Trp Asn Asn Gln Arg Pro Ser
                5

<210> SEQ ID NO 130
<211> LENGTH: 11
<212> TYPE: PRT
<213> ORGANISM: Homo sapiens

<400> SEQUENCE: 130

Ala Ala Trp Asp Asp Ala Ala Arg Val Leu Leu
        5                   10

<210> SEQ ID NO 131
<211> LENGTH: 1008
<212> TYPE: DNA
<213> ORGANISM: Macaca fascicularis

<400> SEQUENCE: 131

| | | |
|---|---|---|
| atgaaagtgt tactccgact tatttgtttc attgctctac tgatttcttt tctggaggct | 60 |
| gataaatgca atgaacgtga agaaaaaata attttagtgt catctgcaaa tgaaattgat | 120 |
| gttcgtccct gtcctcttaa cccaaatgaa tacaaaggca ctataacatg gtataaaaat | 180 |
| gacagcaaga cacctatatc tacagaacaa gcctccagga ttcatcagca caaaaagaaa | 240 |
| ctttggtttg ttcctgctaa ggtagaagat tcaggacatt actactgtgt ggtaagaaat | 300 |
| tcatcttact gctcagaat taaaataact gcaaaatttg tggagaatga gcctaacttg | 360 |
| tgttataatg cagaagccat atttaagcag agactacccg ttgcaggaga tggaggactt | 420 |
| gtgtgccctt atatggagtt ttttaaagac gaaaataatg agttacctaa attactgtgg | 480 |
| tataaggatt gcaaacctct acttcttgac aatataaact ttagtggagt caaagatagg | 540 |
| ctcatcgtga tgaatgtggc tgaaaagcat agagggaact atacttgtca tgcatcctac | 600 |
| acatacttgg gcaagcaata tcctattacc cgggtaatag aatttattac tctagaggaa | 660 |
| aacaaaccca aaggcctgt gattgtgagc ccagctaatg agacaataga agtagacttg | 720 |
| ggatcccaga tacaattgat ctgtaatgtc actggccagt tgagtgatac tgcctactgg | 780 |
| aagtggaatg ggtccttcat tgatgaagat gacccagtgc taggggaaga ctattacagt | 840 |
| gtggaaaatc ctgcaaacaa agaaggagt accctcatca cagtgcttaa tatatcagaa | 900 |
| actgaaagta gattttataa acatccattt acctgtttag ccaggaatac acatggtatg | 960 |
| gatgcagcat atgtccagtt aatatatcca gtcactaaat tccagaag | 1008 |

<210> SEQ ID NO 132
<211> LENGTH: 336
<212> TYPE: PRT
<213> ORGANISM: Macaca fascicularis

<400> SEQUENCE: 132

Met Lys Val Leu Leu Arg Leu Ile Cys Phe Ile Ala Leu Leu Ile Ser
1               5                   10                  15

Phe Leu Glu Ala Asp Lys Cys Asn Glu Arg Glu Glu Lys Ile Ile Leu
            20                  25                  30

Val Ser Ser Ala Asn Glu Ile Asp Val Arg Pro Cys Pro Leu Asn Pro
        35                  40                  45

Asn Glu Tyr Lys Gly Thr Ile Thr Trp Tyr Lys Asn Asp Ser Lys Thr
    50                  55                  60

Pro Ile Ser Thr Glu Gln Ala Ser Arg Ile His Gln His Lys Lys Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Thr Ala Lys
            100                 105                 110

Phe Val Glu Asn Glu Pro Asn Leu Cys Tyr Asn Ala Glu Ala Ile Phe
        115                 120                 125

Lys Gln Arg Leu Pro Val Ala Gly Asp Gly Gly Leu Val Cys Pro Tyr
    130                 135                 140

```
Met Glu Phe Phe Lys Asp Glu Asn Asn Glu Leu Pro Lys Leu Leu Trp
145                 150                 155                 160

Tyr Lys Asp Cys Lys Pro Leu Leu Leu Asp Asn Ile Asn Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
    210                 215                 220

Arg Pro Val Ile Val Ser Pro Ala Asn Glu Thr Ile Glu Val Asp Leu
225                 230                 235                 240

Gly Ser Gln Ile Gln Leu Ile Cys Asn Val Thr Gly Gln Leu Ser Asp
                245                 250                 255

Thr Ala Tyr Trp Lys Trp Asn Gly Ser Phe Ile Asp Glu Asp Asp Pro
                260                 265                 270

Val Leu Gly Glu Asp Tyr Tyr Ser Val Glu Asn Pro Ala Asn Lys Arg
            275                 280                 285

Arg Ser Thr Leu Ile Thr Val Leu Asn Ile Ser Glu Thr Glu Ser Arg
        290                 295                 300

Phe Tyr Lys His Pro Phe Thr Cys Leu Ala Arg Asn Thr His Gly Met
305                 310                 315                 320

Asp Ala Ala Tyr Val Gln Leu Ile Tyr Pro Val Thr Lys Phe Gln Lys
                325                 330                 335

<210> SEQ ID NO 133
<211> LENGTH: 1773
<212> TYPE: DNA
<213> ORGANISM: Homo sapiens

<400> SEQUENCE: 133
atgaaagtgt tactcagact tatttgtttc atagctctac tgatttcttc tctggaggct    60
gataaatgca aggaacgtga agaaaaaata attttagtgt catctgcaaa tgaaattgat   120
gttcgtccct gtcctcttaa cccaaatgaa cacaaaggca ctataacttg gtataaagat   180
gacagcaaga cacctgtatc tacagaacaa gcctccagga ttcatcaaca aagagaaa    240 ctttggtttg ttcctgctaa ggtggaggat tcaggacatt actattgcgt ggtaagaat    300 tcatcttact gcctcagaat taaaataagt gcaaatttg tggagaatga gcctaactta    360
tgttataatg cacaagccat atttaagcag aaactacccg ttgcaggaga cggaggactt   420
gtgtgccctt atatggagtt ttttaaaaat gaaaataatg agttacctaa attacagtgg   480
tataaggatt gcaaacctct acttcttgac aatatacact tagtggagt caaagatagg    540 ctcatcgtga tgaatgtggc tgaaaagcat agagggaact atacttgtca tgcatcctac   600
acatacttgg gcaagcaata tcctattacc cgggtaatag aatttattac tctagaggaa   660
aacaaaccca aaggcctgt gattgtgagc ccagctaatg agacaatgga agtagacttg   720
ggatcccaga tacaattgat ctgtaatgtc accggccagt tgagtgacat tgcttactgg   780
aagtggaatg ggtcagtaat tgatgaagat gacccagtgc taggggaaga ctattacagt   840
gtggaaaatc ctgcaaacaa agaaggagt accctcatca gtgtgcttaa tatatcggaa   900
attgaaagta gatttataa acatccattt acctgtttg ccaagaatac acatggtata    960
gatgcagcat atatccagtt aatatatcca gtcactaatt tccagaagaa gggtgggcgc  1020
gccgacccag ctttcttgta caagtggtg ggggccgccc ccaatcttg tgacaaaact  1080
```

-continued

```
cacacatgcc caccgtgccc agcacctgaa ctcctggggg gaccgtcagt cttcctcttc    1140 ccccccaaaac ccaaggacac cctcatgatc tcccggaccc ctgaggtcac atgcgtggtg   1200
gtggacgtga gccacgaaga ccctgaggtc aagttcaact ggtacgtgga cggcgtggag   1260
gtgcataatg ccaagacaaa gccgcgggag gagcagtaca acagcacgta ccgtgtggtc   1320
agcgtcctca ccgtcctgca ccaggactgg ctgaatggca aggagtacaa gtgcaaggtc   1380
tccaacaaag ccctcccagc ccccatcgag aaaaccatct ccaaagccaa agggcagccc   1440
cgagaaccac aggtgtacac cctgccccca tcccgggagg agatgaccaa gaaccaggtc   1500
agcctgacct gcctggtcaa aggcttctat cccagcgaca tcgccgtgga gtgggagagc   1560
aatgggcagc cggagaacaa ctacaagacc acgcctcccg tgctggactc cgacggctcc   1620
ttcttcctct atagcaagct caccgtggac aagagcaggt ggcagcaggg gaacgtcttc   1680
tcatgctccg tgatgcatga ggctctgcac aaccactaca cgcagaagag cctctccctg   1740
tctccgggta aacatcatca tcaccaccat taa                                1773
```

<210> SEQ ID NO 134
<211> LENGTH: 589
<212> TYPE: PRT
<213> ORGANISM: Homo sapiens

<400> SEQUENCE: 134

```
Lys Val Leu Leu Arg Leu Ile Cys Phe Ile Ala Leu Leu Ile Ser Ser
 1               5                  10                  15

Leu Glu Ala Asp Lys Cys Lys Glu Arg Glu Glu Lys Ile Ile Leu Val
            20                  25                  30

Ser Ser Ala Asn Glu Ile Asp Val Arg Pro Cys Pro Leu Asn Pro Asn
        35                  40                  45

Glu His Lys Gly Thr Ile Thr Trp Tyr Lys Asp Asp Ser Lys Thr Pro
    50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
           100                 105                 110

Val Glu Asn Glu Pro Asn Leu Cys Tyr Asn Ala Gln Ala Ile Phe Lys
       115                 120                 125

Gln Lys Leu Pro Val Ala Gly Asp Gly Gly Leu Val Cys Pro Tyr Met
   130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
        195                 200                 205

Thr Arg Val Ile Glu Phe Ile Thr Leu Glu Glu Asn Lys Pro Thr Arg
    210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255
```

```
Ala Tyr Trp Lys Trp Asn Gly Ser Val Ile Asp Glu Asp Pro Val
            260                 265                 270

Leu Gly Glu Asp Tyr Tyr Ser Val Glu Asn Pro Ala Asn Lys Arg Arg
        275                 280                 285

Ser Thr Leu Ile Thr Val Leu Asn Ile Ser Glu Ile Glu Ser Arg Phe
290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Phe Gln Lys Lys
                325                 330                 335

Gly Gly Arg Ala Asp Pro Ala Phe Leu Tyr Lys Val Val Gly Ala Ala
            340                 345                 350

Pro Lys Ser Cys Asp Lys Thr His Thr Cys Pro Pro Cys Pro Ala Pro
        355                 360                 365

Glu Leu Leu Gly Gly Pro Ser Val Phe Leu Phe Pro Pro Lys Pro Lys
    370                 375                 380

Asp Thr Leu Met Ile Ser Arg Thr Pro Glu Val Thr Cys Val Val Val
385                 390                 395                 400

Asp Val Ser His Glu Asp Pro Glu Val Lys Phe Asn Trp Tyr Val Asp
                405                 410                 415

Gly Val Glu Val His Asn Ala Lys Thr Lys Pro Arg Glu Glu Gln Tyr
            420                 425                 430

Asn Ser Thr Tyr Arg Val Val Ser Val Leu Thr Val Leu His Gln Asp
        435                 440                 445

Trp Leu Asn Gly Lys Glu Tyr Lys Cys Lys Val Ser Asn Lys Ala Leu
    450                 455                 460

Pro Ala Pro Ile Glu Lys Thr Ile Ser Lys Ala Lys Gly Gln Pro Arg
465                 470                 475                 480

Glu Pro Gln Val Tyr Thr Leu Pro Pro Ser Arg Glu Glu Met Thr Lys
                485                 490                 495

Asn Gln Val Ser Leu Thr Cys Leu Val Lys Gly Phe Tyr Pro Ser Asp
            500                 505                 510

Ile Ala Val Glu Trp Glu Ser Asn Gly Gln Pro Glu Asn Asn Tyr Lys
        515                 520                 525

Thr Thr Pro Pro Val Leu Asp Ser Asp Gly Ser Phe Phe Leu Tyr Ser
    530                 535                 540

Lys Leu Thr Val Asp Lys Ser Arg Trp Gln Gln Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Pro Gly Lys His His His His His His
            580                 585

<210> SEQ ID NO 135
<211> LENGTH: 1773
<212> TYPE: DNA
<213> ORGANISM: Macaca fascicularis

<400> SEQUENCE: 135
atgaaagtgt tactccgact tatttgtttc attgctctac tgatttcttt tctggaggct      60
gataaatgca atgaacgtga agaaaaaata atttagtgt catctgcaaa tgaaattgat     120
gttcgtccct gtcctcttaa cccaaatgaa tacaaaggca ctataacatg gtataaaaat     180
gacagcaaga cacctatatc tacagaacaa gcctccagga ttcatcagca caaaagaaa      240 ctttggtttg ttcctgctaa ggtagaagat tcaggacatt actactgtgt ggtaagaaat     300
```

```
tcatcttact gcctcagaat taaaataact gcaaaatttg tggagaatga gcctaacttg      360
tgttataatg cagaagccat atttaagcag agactacccg ttgcaggaga tggaggactt      420
gtgtgcccct atatggagtt ttttaaagac gaaaataatg agttacctaa attactgtgg      480
tataaggatt gcaaacctct acttcttgac aatataaact ttagtggagt caaagatagg      540
ctcatcgtga tgaatgtggc tgaaaagcat agagggaact atacttgtca tgcatcctac      600
acatacttgg gcaagcaata tcctattacc cgggtaatag aatttattac tctagaggaa      660
aacaaaccca caaggcctgt gattgtgagc ccagctaatg agacaataga agtagacttg      720
ggatcccaga tacaattgat ctgtaatgtc actggccagt tgagtgatac tgcctactgg      780
aagtggaatg ggtccttcat tgatgaagat gacccagtgc taggggaaga ctattacagt      840
gtggaaaatc ctgcaaacaa agaaggagt accctcatca cagtgcttaa tatatcagaa      900
actgaaagta gattttataa acatccattt acctgtttag ccaggaatac acatggtatg      960
gatgcagcat atgtccagtt aatatatcca gtcactaaat tccagaagaa gggtgggcgc     1020
gccgacccag ctttcttgta caaagtggtg ggggccgccc ccaaatcttg tgacaaaact     1080
cacacatgcc caccgtgccc agcacctgaa ctcctggggg gaccgtcagt cttcctcttc     1140
cccccaaaac ccaaggacac cctcatgatc tcccggaccc ctgaggtcac atgcgtggtg     1200
gtggacgtga gccacgaaga ccctgaggtc aagttcaact ggtacgtgga cggcgtggag     1260
gtgcataatg ccaagacaaa gccgcgggag gagcagtaca acagcacgta ccgtgtggtc     1320
agcgtcctca ccgtcctgca ccaggactgg ctgaatggca aggagtacaa gtgcaaggtc     1380
tccaacaaag ccctcccagc ccccatcgag aaaaccatct ccaaagccaa agggcagccc     1440
cgagaaccac aggtgtacac cctgccccca tcccgggagg agatgaccaa gaaccaggtc     1500
agcctgacct gcctggtcaa aggcttctat cccagcgaca tcgccgtgga gtgggagagc     1560
aatgggcagc cggagaacaa ctacaagacc acgcctcccg tgctggactc cgacggctcc     1620
ttcttcctct atagcaagct caccgtggac aagagcaggt ggcagcaggg gaacgtcttc     1680
tcatgctccg tgatgcatga ggctctgcac aaccactaca cgcagaagag cctctccctg     1740
tctccgggta aacatcatca tcaccaccat taa                                   1773
```

<210> SEQ ID NO 136
<211> LENGTH: 589
<212> TYPE: PRT
<213> ORGANISM: Macaca fascicularis

<400> SEQUENCE: 136

```
Lys Val Leu Leu Arg Leu Ile Cys Phe Ile Ala Leu Leu Ile Ser Phe
1               5                   10                  15

Leu Glu Ala Asp Lys Cys Asn Glu Arg Glu Glu Lys Ile Ile Leu Val
                20                  25                  30

Ser Ser Ala Asn Glu Ile Asp Val Arg Pro Cys Pro Leu Asn Pro Asn
            35                  40                  45

Glu Tyr Lys Gly Thr Ile Thr Trp Tyr Lys Asn Asp Ser Lys Thr Pro
        50                  55                  60

Ile Ser Thr Glu Gln Ala Ser Arg Ile His Gln His Lys Lys Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Thr Ala Lys Phe
                100                 105                 110
```

```
Val Glu Asn Glu Pro Asn Leu Cys Tyr Asn Ala Glu Ala Ile Phe Lys
    115                 120                 125

Gln Arg Leu Pro Val Ala Gly Asp Gly Leu Val Cys Pro Tyr Met
130                 135                 140

Glu Phe Phe Lys Asp Glu Asn Asn Glu Leu Pro Lys Leu Leu Trp Tyr
145                 150                 155                 160

Lys Asp Cys Lys Pro Leu Leu Leu Asp Asn Ile Asn Phe Ser Gly Val
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
        195                 200                 205

Thr Arg Val Ile Glu Phe Ile Thr Leu Glu Glu Asn Lys Pro Thr Arg
    210                 215                 220

Pro Val Ile Val Ser Pro Ala Asn Glu Thr Ile Glu Val Asp Leu Gly
225                 230                 235                 240

Ser Gln Ile Gln Leu Ile Cys Asn Val Thr Gly Gln Leu Ser Asp Thr
                245                 250                 255

Ala Tyr Trp Lys Trp Asn Gly Ser Phe Ile Asp Glu Asp Asp Pro Val
            260                 265                 270

Leu Gly Glu Asp Tyr Tyr Ser Val Glu Asn Pro Ala Asn Lys Arg Arg
        275                 280                 285

Ser Thr Leu Ile Thr Val Leu Asn Ile Ser Glu Thr Glu Ser Arg Phe
    290                 295                 300

Tyr Lys His Pro Phe Thr Cys Leu Ala Arg Asn Thr His Gly Met Asp
305                 310                 315                 320

Ala Ala Tyr Val Gln Leu Ile Tyr Pro Val Thr Lys Phe Gln Lys Lys
                325                 330                 335

Gly Gly Arg Ala Asp Pro Ala Phe Leu Tyr Lys Val Val Gly Ala Ala
            340                 345                 350

Pro Lys Ser Cys Asp Lys Thr His Thr Cys Pro Pro Cys Pro Ala Pro
        355                 360                 365

Glu Leu Leu Gly Gly Pro Ser Val Phe Leu Phe Pro Pro Lys Pro Lys
    370                 375                 380

Asp Thr Leu Met Ile Ser Arg Thr Pro Glu Val Thr Cys Val Val Val
385                 390                 395                 400

Asp Val Ser His Glu Asp Pro Glu Val Lys Phe Asn Trp Tyr Val Asp
                405                 410                 415

Gly Val Glu Val His Asn Ala Lys Thr Lys Pro Arg Glu Glu Gln Tyr
            420                 425                 430

Asn Ser Thr Tyr Arg Val Val Ser Val Leu Thr Val Leu His Gln Asp
        435                 440                 445

Trp Leu Asn Gly Lys Glu Tyr Lys Cys Lys Val Ser Asn Lys Ala Leu
    450                 455                 460

Pro Ala Pro Ile Glu Lys Thr Ile Ser Lys Ala Lys Gly Gln Pro Arg
465                 470                 475                 480

Glu Pro Gln Val Tyr Thr Leu Pro Pro Ser Arg Glu Glu Met Thr Lys
                485                 490                 495

Asn Gln Val Ser Leu Thr Cys Leu Val Lys Gly Phe Tyr Pro Ser Asp
            500                 505                 510

Ile Ala Val Glu Trp Glu Ser Asn Gly Gln Pro Glu Asn Asn Tyr Lys
        515                 520                 525

Thr Thr Pro Pro Val Leu Asp Ser Asp Gly Ser Phe Phe Leu Tyr Ser
    530                 535                 540
```

```
Lys Leu Thr Val Asp Lys Ser Arg Trp Gln Gln Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Pro Gly Lys His His His His His
            580                 585
```

<210> SEQ ID NO 137
<211> LENGTH: 336
<212> TYPE: PRT
<213> ORGANISM: Homo sapiens

<400> SEQUENCE: 137

```
Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Lys Ile Ile Leu
            20                  25                  30

Val Ser Ser Ala Asn Glu Ile Asp Val Arg Pro Cys Pro Leu Asn Pro
        35                  40                  45

Asn Glu His Lys Gly Thr Ile Thr Trp Tyr Lys Asp Asp Ser Lys Thr
    50                  55                  60

Pro Val Ser Thr Glu Gln Ala Ser Arg Ile His Gln His Lys Glu Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
        115                 120                 125

Lys Gln Lys Leu Pro Val Ala Gly Asp Gly Gly Leu Val Cys Pro Tyr
130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
        195                 200                 205

Ile Thr Arg Val Ile Glu Phe Ile Thr Leu Glu Glu Asn Lys Pro Thr
210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
        275                 280                 285

Arg Ser Thr Leu Ile Thr Val Leu Asn Ile Ser Glu Ile Glu Ser Arg
290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
                325                 330                 335
```

<210> SEQ ID NO 138
<211> LENGTH: 1012
<212> TYPE: DNA
<213> ORGANISM: Homo sapiens

<400> SEQUENCE: 138

```
caccatgaaa gtgttactca gacttatttg tttcatagct ctactgattt cttctctgga      60
ggctgataaa tgcaaggaac gtgaagaaaa aataatttta gtgtcatctg caaatgaaat     120
tgatgttcgt ccctgtcctc ttaacccaaa tgaacacaaa ggcactataa cttggtataa     180
agatgacagc aagacacctg tatctacaga acaagcctcc aggattcatc aacacaaaga     240
gaaactttgg tttgttcctg ctaaggtgga ggattcagga cattactatt gcgtggtaag     300
aaattcatct tactgcctca gaattaaaat aagtgcaaaa tttgtggaga atgagcctaa     360
cttatgttat aatgcacaag ccatatttaa gcagaaacta cccgttgcag gagacggagg     420
acttgtgtgc ccttatatgg agttttttaa aaatgaaaat aatgagttac ctaaattaca     480
gtggtataag gattgcaaac ctctacttct tgacaatata cactttagtg gagtcaaaga     540
taggctcatc gtgatgaatg tggctgaaaa gcatagaggg aactatactt gtcatgcatc     600
ctacacatac ttgggcaagc aatatcctat tacccgggta atagaattta ttactctaga     660
ggaaaacaaa cccacaaggc ctgtgattgt gagcccagct aatgagacaa tggaagtaga     720
cttgggatcc cagatacaat tgatctgtaa tgtcaccggc cagttgagtg acattgctta     780
ctggaagtgg aatgggtcag taattgatga agatgaccca gtgctagggg aagactatta     840
cagtgtggaa aatcctgcaa acaaaagaag gagtaccctc atcacagtgc ttaatatatc     900
ggaaattgaa agtagatttt ataaacatcc atttacctgt tttgccaaga atacacatgg     960
tatagatgca gcatatatcc agttaatata tccagtcact aatttccaga ag           1012
```

<210> SEQ ID NO 139
<211> LENGTH: 336
<212> TYPE: PRT
<213> ORGANISM: Macaca fascicularis

<400> SEQUENCE: 139

```
Met Lys Val Leu Leu Arg Leu Ile Cys Phe Ile Ala Leu Leu Ile Ser
1               5                   10                  15

Phe Leu Glu Ala Asp Lys Cys Asn Glu Arg Glu Lys Ile Ile Leu
                20                  25                  30

Val Ser Ser Ala Asn Glu Ile Asp Val Arg Pro Cys Pro Leu Asn Pro
            35                  40                  45

Asn Glu Tyr Lys Gly Thr Ile Thr Trp Tyr Lys Asn Asp Ser Lys Thr
        50                  55                  60

Pro Ile Ser Thr Glu Gln Ala Ser Arg Ile His Gln His Lys Lys Lys
65                  70                  75                  80

Leu Trp Phe Val Pro Ala Lys Val Glu Asp Ser Gly His Tyr Tyr Cys
                85                  90                  95

Val Val Arg Asn Ser Ser Tyr Cys Leu Arg Ile Lys Ile Thr Ala Lys
            100                 105                 110

Phe Val Glu Asn Glu Pro Asn Leu Cys Tyr Asn Ala Glu Ala Ile Phe
        115                 120                 125

Lys Gln Arg Leu Pro Val Ala Gly Asp Gly Gly Leu Val Cys Pro Tyr
    130                 135                 140

Met Glu Phe Phe Lys Asp Glu Asn Asn Glu Leu Pro Lys Leu Leu Trp
145                 150                 155                 160
```

Tyr Lys Asp Cys Lys Pro Leu Leu Leu Asp Asn Ile Asn Phe Ser Gly
            165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
            195                 200                 205

Ile Thr Arg Val Ile Glu Phe Ile Thr Leu Glu Glu Asn Lys Pro Thr
            210                 215                 220

Arg Pro Val Ile Val Ser Pro Ala Asn Glu Thr Ile Glu Val Asp Leu
225                 230                 235                 240

Gly Ser Gln Ile Gln Leu Ile Cys Asn Val Thr Gly Gln Leu Ser Asp
            245                 250                 255

Thr Ala Tyr Trp Lys Trp Asn Gly Ser Phe Ile Asp Glu Asp Asp Pro
            260                 265                 270

Val Leu Gly Glu Asp Tyr Tyr Ser Val Glu Asn Pro Ala Asn Lys Arg
            275                 280                 285

Arg Ser Thr Leu Ile Thr Val Leu Asn Ile Ser Glu Thr Glu Ser Arg
            290                 295                 300

Phe Tyr Lys His Pro Phe Thr Cys Leu Ala Arg Asn Thr His Gly Met
305                 310                 315                 320

Asp Ala Ala Tyr Val Gln Leu Ile Tyr Pro Val Thr Lys Phe Gln Lys
            325                 330                 335

<210> SEQ ID NO 140
<211> LENGTH: 1012
<212> TYPE: DNA
<213> ORGANISM: Macaca fascicularis

<400> SEQUENCE: 140
caccatgaaa gtgttactcc gacttatttg tttcattgct ctactgattt cttttctgga      60
ggctgataaa tgcaatgaac gtgaagaaaa ataattttta gtgtcatctg caaatgaaat     120
tgatgttcgt ccctgtcctc ttaacccaaa tgaatacaaa ggcactataa catggtataa     180
aaatgacagc aagacaccta tatctacaga acaagcctcc aggattcatc agcacaaaaa     240
gaaactttgg tttgttcctg ctaaggtaga agattcagga cattactact gtgtggtaag     300
aaattcatct tactgcctca gaattaaaat aactgcaaaa tttgtggaga atgagcctaa     360
cttgtgttat aatgcagaag ccatatttaa gcagagacta cccgttgcag agatggaggg     420
acttgtgtgc ccttatatgg agttttttaa agacgaaaat aatgagttac ctaaattact     480
gtggtataag gattgcaaac ctctacttct tgacaatata aactttagtg gagtcaaaga     540
taggctcatc gtgatgaatg tggctgaaaa gcatagaggg aactatactt gtcatgcatc     600
ctacacatac ttgggcaagc aatatcctat tacccgggta atagaattta ttactctaga     660
ggaaaacaaa cccacaaggc ctgtgattgt gagcccagct aatgagacaa tagaagtaga     720
cttgggatcc cagatacaat tgatctgtaa tgtcactggc cagttgagtg atactgccta     780
ctggaagtgg aatgggtcct tcattgatga agatgaccca gtgctagggg aagactatta     840
cagtgtggaa atcctgcaaa acaaaagaag gagtaccctc atcacagtgc ttaatatatc     900
agaaactgaa agtagatttt ataaacatcc atttacctgt ttagccagga atacacatgg     960
tatggatgca gcatatgtcc agttaatata tccagtcact aaattccaga ag            1012

<210> SEQ ID NO 141
<211> LENGTH: 179
<212> TYPE: PRT

<213> ORGANISM: Homo sapiens

<400> SEQUENCE: 141

Met Gly Ser Ser His His His His His His Asp Tyr Lys Asp Asp
1               5                   10                  15

Asp Lys His Met Glu Asn Leu Tyr Phe Gln Ser Arg Pro Ser Gly Arg
                20                  25                  30

Lys Ser Ser Lys Met Gln Ala Phe Arg Ile Trp Asp Val Asn Gln Lys
            35                  40                  45

Thr Phe Tyr Leu Arg Asn Asn Gln Leu Val Ala Gly Tyr Leu Gln Gly
        50                  55                  60

Pro Asn Val Asn Leu Glu Glu Lys Ile Asp Val Val Pro Ile Glu Pro
65                  70                  75                  80

His Ala Leu Phe Leu Gly Ile His Gly Gly Lys Met Cys Leu Ser Cys
                85                  90                  95

Val Lys Ser Gly Asp Glu Thr Arg Leu Gln Leu Glu Ala Val Asn Ile
            100                 105                 110

Thr Asp Leu Ser Glu Asn Arg Lys Gln Asp Lys Arg Phe Ala Phe Ile
        115                 120                 125

Arg Ser Asp Ser Gly Pro Thr Thr Ser Phe Glu Ser Ala Ala Cys Pro
    130                 135                 140

Gly Trp Phe Leu Cys Thr Ala Met Glu Ala Asp Gln Pro Val Ser Leu
145                 150                 155                 160

Thr Asn Met Pro Asp Glu Gly Val Met Val Thr Lys Phe Tyr Phe Gln
                165                 170                 175

Glu Asp Glu

<210> SEQ ID NO 142
<211> LENGTH: 180
<212> TYPE: PRT
<213> ORGANISM: Homo sapiens

<400> SEQUENCE: 142

Met Gly Ser Ser His His His His His His Asp Tyr Lys Asp Asp
1               5                   10                  15

Asp Lys His Met Glu Asn Leu Tyr Phe Gln Ser Ala Pro Val Arg Ser
                20                  25                  30

Leu Asn Cys Thr Leu Arg Asp Ser Gln Gln Lys Ser Leu Val Met Ser
            35                  40                  45

Gly Pro Tyr Glu Leu Lys Ala Leu His Leu Gln Gly Gln Asp Met Glu
        50                  55                  60

Gln Gln Val Val Phe Ser Met Ser Phe Val Gln Gly Glu Glu Ser Asn
65                  70                  75                  80

Asp Lys Ile Pro Val Ala Leu Gly Leu Lys Glu Lys Asn Leu Tyr Leu
                85                  90                  95

Ser Cys Val Leu Lys Asp Asp Lys Pro Thr Leu Gln Leu Glu Ser Val
            100                 105                 110

Asp Pro Lys Asn Tyr Pro Lys Lys Lys Met Glu Lys Arg Phe Val Phe
        115                 120                 125

Asn Lys Ile Glu Ile Asn Asn Lys Leu Glu Phe Glu Ser Ala Gln Phe
    130                 135                 140

Pro Asn Trp Tyr Ile Ser Thr Ser Gln Ala Glu Asn Met Pro Val Phe
145                 150                 155                 160

Leu Gly Gly Thr Lys Gly Gly Gln Asp Ile Thr Asp Phe Thr Met Gln
                165                 170                 175

Phe Val Ser Ser
        180

<210> SEQ ID NO 143
<211> LENGTH: 76
<212> TYPE: DNA
<213> ORGANISM: Artificial
<220> FEATURE:
<223> OTHER INFORMATION: Primer

<400> SEQUENCE: 143
agaccacaac ggtttccctc tagaaataat tttgtttaac tttaagaagg agatatatcc     60
atggcccagg tgcagc                                                     76

<210> SEQ ID NO 144
<211> LENGTH: 23
<212> TYPE: DNA
<213> ORGANISM: Artificial
<220> FEATURE:
<223> OTHER INFORMATION: Primer

<400> SEQUENCE: 144
caccatgaaa gtgttactca gac                                             23

<210> SEQ ID NO 145
<211> LENGTH: 21
<212> TYPE: DNA
<213> ORGANISM: Artificial
<220> FEATURE:
<223> OTHER INFORMATION: Primer

<400> SEQUENCE: 145
cttctggaaa ttagtgactg g                                               21

<210> SEQ ID NO 146
<211> LENGTH: 21
<212> TYPE: DNA
<213> ORGANISM: Artificial
<220> FEATURE:
<223> OTHER INFORMATION: Primer

<400> SEQUENCE: 146
cttctggaat ttagtgactg g                                               21

<210> SEQ ID NO 147
<211> LENGTH: 20
<212> TYPE: DNA
<213> ORGANISM: Artificial
<220> FEATURE:
<223> OTHER INFORMATION: Primer

<400> SEQUENCE: 147
caccatgctg ccgaggcttg                                                 20

<210> SEQ ID NO 148
<211> LENGTH: 23
<212> TYPE: DNA
<213> ORGANISM: Artificial
<220> FEATURE:
<223> OTHER INFORMATION: Primer

<400> SEQUENCE: 148
attcttgaag tcaggaactg ggt                                             23

<210> SEQ ID NO 149
<211> LENGTH: 47

-continued

```
<212> TYPE: DNA
<213> ORGANISM: Artificial
<220> FEATURE:
<223> OTHER INFORMATION: Primer

<400> SEQUENCE: 149
cctcatatgg aaaacctgta cttccagtct cgaccctctg ggagaaa           47

<210> SEQ ID NO 150
<211> LENGTH: 29
<212> TYPE: DNA
<213> ORGANISM: Artificial
<220> FEATURE:
<223> OTHER INFORMATION: Primer

<400> SEQUENCE: 150
atatctcgag ctactcgtcc tcctggaag                              29

<210> SEQ ID NO 151
<211> LENGTH: 48
<212> TYPE: DNA
<213> ORGANISM: Artificial
<220> FEATURE:
<223> OTHER INFORMATION: Primer

<400> SEQUENCE: 151
cctcatatgg aaaacctgta cttccagtct gcacctgtac gatcactg         48

<210> SEQ ID NO 152
<211> LENGTH: 33
<212> TYPE: DNA
<213> ORGANISM: Artificial
<220> FEATURE:
<223> OTHER INFORMATION: Primer

<400> SEQUENCE: 152
atatctcgag ttaggaagac acaaattgca tgg                         33
```

NUCLEIC ACID MOLECULE ENCODING A SPECIFIC IL-1R1 ANTIBODY

CROSS-REFERENCE TO RELATED APPLICATIONS

This application is a Continuation of U.S. application Ser. No. 12/612,781, filed on Nov. 5, 2009 now U.S. Pat. No. 8,298,533, said application Ser. No. 12/612,781 claims the benefit under 35 U.S.C. §119(e) of U.S. Provisional Application No. 61/112,381 filed on Nov. 7, 2008. Each of the above listed applications is incorporated by reference herein in its entirety for all purposes.

This application claims the benefit under 35 U.S.C. §119 (e) of Application No. 61/112,381 (US) filed on 7 Nov. 2008.

REFERENCE TO THE SEQUENCE LISTING

This application incorporates by reference a Sequence Listing submitted with this application as text file entitled 2012-09-14_Seq created on Nov. 2, 2009, and having a size of 86.5 kilobytes.

This invention relates to binding members, especially antibody molecules, for the interleukin 1 receptor-1 (IL-1R1). The binding members are useful for the treatment of disorders mediated by IL-1R1 including rheumatoid arthritis, asthma and chronic obstructive pulmonary disease (COPD). The invention also relates to processes for the preparation of such binding members, methods of treatment of disorders mediated by IL-1R1 using binding members of the invention and the use of binding members of the invention in the preparation of a medicament for the treatment of disorders mediated by IL-1R1.

interleukin (IL-1) is a multifunctional cytokine, which plays a major role in inflammatory responses during immune-mediated diseases and infections. IL-1 is produced from a variety of cell types following stimulation with bacterial products, cytokines or immune complexes. IL-1 displays autocrine and paracrine activities on a variety of cell types promoting the production of inflammatory mediators such as prostaglandins, nitric oxide, cytokines, chemokines, metalloproteinases and adhesion molecules. Blocking IL-1 biological activity should be beneficial to prevent tissue damage caused by excessive production or disregulated IL-1 activity or to normalise aberrant responses to pathogens for example during an exacerbation of COPD.

The IL-1 family of cytokines currently consists of eleven individual members, IL-1alpha (IL-1α), IL-1beta (IL-1β), interleukin-18 (IL-18), Interleukin 1 antagonist (IL-1Ra), IL1F5-10 and Interleukin-33 (IL-33). Four of these, namely IL-1α, IL-1β, IL-18 & IL-1Ra (IL-1 receptor antagonist), have been characterised most fully and linked to pathological processes in a variety of diseases, and IL-1α, IL-1β, and IL-1Ra alone have clearly been shown to interact with membrane IL-1R1 (1, 2, 3). IL-1α and IL-1β are the products of separate genes. These proteins are related at the amino acid level, IL-1α and IL-1β share 22% homology, with IL-1α and IL-1Ra sharing 18% homology. IL-1β shares 26% homology with IL-1Ra. The genes for IL-1α, IL-1β & IL-1Ra members are located on a similar region in human chromosome 2q14 (4, 5).

Both IL-1α and IL-1β are synthesized as 31-kDa precursor peptides that are cleaved to generate 17-kDa mature IL-1α and IL-1β. IL-1β is produced by a variety of cell types including epithelial cells and macrophages. It is released from cells after cleavage by the cysteine protease caspase-1 (IL-1β converting enzyme (ICE) (6)). IL-1α is cleaved by calpain proteases and can remain on the plasma membrane from where it appears to activate cells, via direct cell to cell contact (7). Pro-IL-1α contains a nuclear localization sequence in its amino terminal, which can lead to activation of a variety of cellular pathways (8).

IL-1Ra is a naturally occurring inhibitor of the IL-1 system. It is produced as four different isoforms derived from alternative mRNA splicing and alternative translation initiation. A 17 kDa secreted isoform of IL-1Ra is expressed as variably glycosylated species, of 22-25 Kda (9,10) now termed sIL-1Ra. An 18 kDa intracellular isoform is termed icIL-1Ra1 (11). The isoform icIL-1Ra2 is produced by an alternative transcriptional splice from exon located between icIL-1Ra1 and sIL-1Ra first exons (12) A third 16 kDa intracellular isoform icIL-1Ra3 has also been identified (13). Kineret® (anakinra) is a recombinant, nonglycosylated form of the soluble human interleukin-1 receptor antagonist (IL-1Ra). Kineret® differs from native human IL-1Ra in that it has the addition of a single methionine residue at its amino terminus. Kineret® consists of 153 amino acids and has a molecular weight of 17.3 kilodaltons. Kineret® is approved for the treatment of moderate to severe active rheumatoid arthritis.

IL-1α and IL-1β exert their biological effects by binding to a transmembrane receptor, IL-1R1 (RefSeq NM_00877), which belongs to the IL-1 receptor family. There are currently ten members of the IL-1 receptor family (14); IL-1Receptor I (IL-1R1 (80 kDa), IL-1RII (68 kDa) and IL-1 receptor accessory protein (IL-1RacP) being relevant to the signalling of IL-1α and β. IL-1R1 and IL1RacP complex in the cell membrane to form a high affinity receptor capable of signalling on binding of IL-1α or Il-1β. IL-1Ra binds IL-1R1 but does not interact with IL-1RAcP. IL-1α, Il-1β and IL-1Ra also bind IL-RII which does not have an intracellular signalling domain.

All three of these receptors can be expressed as membrane bound or soluble proteins. IL-1R type I (IL-1R1), IL-1RII & IL-1R accessory protein (IL-1RAcP) belong to the immunoglobulin (Ig) gene superfamily with their extracellular region containing three Ig-like domains. IL-1R1 and IL-1RacP have cytoplasmic domains (Toll-like IL-1R (TIR)) domains, which are related to the Toll-Like receptor (TLR) superfamily. IL-1R1 is termed the signalling receptor as upon ligand binding and complexing with IL-1RAcP the signal transduction is initiated via its cytoplasmic tail of 213 amino acid residues (15). Current literature suggests that IL-1RII acts only as a 'decoy receptor' either at the cell surface or extracellularly as a soluble form (16).

The crystal structure of the extracellular region of the IL-1R1 bound to IL-1β has been resolved to 2.5 A resolution (17). The two N-terminal Ig domains appear rigid due to a disulfide linker, with the third domain showing more flexibility. The IL-1R1 appears wrapped around IL-1β, with two significant areas of contact. One of these is in a groove between domains 1 & 2, while the second area of contact is a smaller area located on the third domain. Interestingly the IL-1Ra also appears to bind to the groove region between domains 1&2 of the IL-1R1, however there does not appear to be any contact between the IL-1Ra and the third Ig domain of the IL-1R1 (18).

Once IL-1 has bound to the IL-1R1 chain the IL-1RAcP is recruited to the ligand-receptor pair and forms a high affinity receptor complex, which results in initiation of signal transduction.

A model of IL-1RAcP interaction with IL-1-IL-1R1 has been proposed based on mutagenesis and antibody studies (19, 20 & 21). It shows that the IL-1RAcP interacts with the interface between IL-1 and IL-1R1. These studies also demonstrated that the AcP could not interact with the IL-1Ra-IL-1R1 pair, which forms a more relaxed structure. Greenfeder et al. (22) have shown that the IL-1R1 bound with IL-1Ra fails to recruit the IL-1RAcP and therefore fails to signal. The ILRa acts by occupying the binding site on IL-1R1 for IL-1β or IL-1α and in addition failing to form the signalling complex with IL-1RAcP.

A further member of the IL-1R family is the type II IL-1R (IL-1RII). This receptor is highly homologous to the IL-1R1 in the extracellular region and can bind IL-1α & IL-1β. Current evidence suggests that however IL-1RII, does not initiate signalling due to the lack of an intracytoplasmic domain. This receptor can be cleaved from the cell surface and along with the membrane form act as inhibitors of IL-1 activity by acting as decoy receptors (16). IL-1RII has a higher affinity for IL-1β and a lower affinity for the IL-1Ra, which means that IL-1RII does not block the inhibitory activity of the IL-1Ra (23). Ligand binding to the IL-1RII causes recruitment of the IL-1RAcP, however this complex remains non-signalling (24). Because the IL-1RAcP is removed in this way by the IL-1RII and prevents IL-1RAcP binding to IL-1R1, it can also block IL-1 actions by this mechanism, and this is termed "co-receptor competition" (24). However, it has not been definitively disproved at this time that IL-1RII could recruit another signalling chain, although cells that express high levels of IL-1RII have been shown to become unresponsive to IL-1β (25).

The high affinity complex formed when IL-1 binds to IL-1R1 leads to the recruitment of the IL-1RAcP and initiates receptor signalling. IL-1R1 and IL-1RacP have cytoplasmic domains (Toll-like IL-1R (TIR)) domains, which are related to the Toll-Like receptor (TLR) superfamily.

During signal transduction the TIR domain of the adaptor molecule MyD88 interacts with the TIR domain of the IL-1RAcP and causes recruitment of a receptor complex containing IRAK-4 and IRAK-1. It has been proposed that the phosphorylated IRAK in turn recruits TRAF6 to the receptor complex. IRAK then brings TRAF6 to TAK1, TAB1, and TAB2, which are preassociated on the membrane before stimulation to form a membrane-associated complex II. The formation of complex II leads to the phosphorylation of TAK1 and TAB2 on the membrane by an unknown kinase, followed by the dissociation of TRAF6-TAK1-TAB1-TAB2 (complex III) from IRAK and consequent translocation of complex III to the cytosol. The formation of complex III and its interaction with additional cytosolic factors leads to the activation of TAK1. Phosphorylated IRAK remains on the membrane and eventually is ubiquitinated and degraded. Activation of TAK-1 leads to the activation of IKK, degradation of IkB proteins resulting in NF-kB activation that activates transcription in the nucleus. TAK-1 has also been shown to play a role in activation of the mitogen activated protein kinase pathway (MAPK) that, via activation of p38, JNK and ERK1/2, regulates activity of transcription factors including AP1 (26). Since signalling transduction is amplified down these multiple pathways, the percentage receptor occupancy per cell by ligand only needs to be low to initiate a physiological response in the IL-1R expressing cell (perhaps as low as 10 receptors occupied per cell).

IL-1 is a major inflammatory cytokine, which has an important role in many chronic inflammatory diseases. The expression of IL-1 at the gene and protein level has been examined in a variety of diseases. Increased levels of IL-1 have been reported in type 2 diabetes (27,28, 29), HIV-1 solid tumours, leukaemias, Alzheimers disease, ischaemic disease (30) and atherosclerosis (31), asthma, COPD and OA (32). IL-1 has been shown to exert multiple biological effects by a variety of in vitro and in vivo studies. Its pleiotropic actions are related to its major role on the gene expression of a variety of inflammatory mediators, including prostanoids, nitric oxide, cytokines, chemokines, proteases & adhesion molecules and cytokine receptor expression (32). Excessive production or expression of these inflammatory mediators is associated with disease pathology and tissue remodelling and destruction. Therefore, IL-1 represents a pivotal therapeutic target for many common inflammatory disorders such as rheumatoid arthritis, osteoarthritis (OA), asthma and chronic obstructive pulmonary disease (COPD), type 2 diabetes, ischaemic disease and atherosclerosis.

The present invention provides binding members which bind to IL-1R1 and inhibit the biological activity of IL-1α and/or IL-1β, including fully human antibodies, or antigen-binding portions thereof.

Binding members directed to IL-1R1 have been disclosed in the following International Patent Applications: WO2004/022718, WO 2005/023872, WO 2007/063311, WO 2007/063308 and WO 2006/059108.

In another embodiment the invention provides an isolated binding member, for example, an antibody, specific for IL-1R1 which competes with IL-1Ra for binding to IL-1R1.

In another embodiment the invention provides an isolated binding member specific for IL-1R1 which competes with IL-1 and IL-1Ra for binding to IL-1R1 and binds Il-1R1 with a KD of 10 pM or less when measured by Kinexa™. In one embodiment IL-1 relates to IL-1α, in another embodiment Il-1 relates to IL-1β. In another embodiment Il-1 relates to both IL-1α and IL-1β.

Antibodies which block both IL-1 and IL1Ra binding are believed to be particularity efficacious. In the absence of IL-1, the IL-1R1 internalizes with a $t_{1/2}$ of approximately 11 hours, however in the presence of IL-1 the receptor undergoes more rapid internalisation so that $t_{1/2}$ is approximately 1.5 hours [33, 34]. In contrast, IL-1Ra binds IL-1R1 but does not induce increased internalisation of the receptor [35]. When the IL-1R1 is internalised it is not readily recycled back to the membrane surface [33] and so it is possible that antibodies binding to an epitope similar to that of IL-1 alone may be internalised readily, may be channeled into endosomal pathways as a result, and may undergo a greater rate of clearance via this receptor-mediated clearance mechanism. Antibodies to epitopes more similar to IL-1ra may be less susceptible to increase the rate of receptor internalisation and may not undergo increased clearance via a receptor mediated mechanism, and are therefore perhaps more likely to have a circulatory clearance and half-life typical of a human IgG. International patent application WO 2004/022718 disclosed a class of antibodies which blocked both IL-1 and IL-1Ra binding to IL-1R1, however, this class was much less potent than the preferred class of antibodies disclosed which bound to the third domain of Il-1R and prevented Il-1β binding. In contrast, antibodies of the present invention are able to block Il-1 and Il-1Ra binding to Il-1R1 and bind Il-1R1 with high affinity.

In another embodiment of the invention there is provided an isolated binding member specific for IL-1R1 which has a mean $IC_{50}$, averaged from at least 6 different donors, of less than 1 nM for the inhibition of IL-1β induced IL-6 production in whole human blood in the presence of 30 pM IL-1β. In further embodiments the mean $IC_{50}$, averaged from at least 10, 15 or 20 different donors. In further embodiments the mean $IC_{50}$ is less than 800 pM, less than 700 pM, less than 600 pM, less than 500 pM, less than 400 pM, less than 300 pM, less than 300 pM, less than 200 pM, less than 100 pM or less than 50 pM.

Binding members of the invention bind to IL-1R1 and neutralize IL-1R1 with high potency. Neutralisation means inhibition of a biological activity of IL-1R1. Binding members of the invention may neutralize one or more biological activities of IL-1R1, typically binding members of the invention inhibit IL1α and IL1β binding to IL-1R1.

The binding members of the invention may also bind to and neutralize non-human IL-1R1, meaning IL-1R1 orthologs that occur naturally in species other than human.

Binding members of the invention are normally specific for IL-1R1 over other proteins, and thus bind IL-1R1 selectively. Such selectivity may be determined or demonstrated, for example, in a standard competition assay.

Suitable assays for measuring neutralisation of IL-1R1 by binding members of the invention include, for example, ligand receptor biochemical assays and surface plasmon resonance (SPR) (e.g., BIACORE™).

Binding kinetics and affinity (expressed as the equilibrium dissociation constant $K_D$) of IL-1R1-binding members for human IL-1R1 may be determined, e.g. using surface plasmon resonance (BIACORE™). Binding members of the invention normally have an affinity for human IL-1R1 ($K_D$) of less than about 1 nM, and in some embodiments have a KD of less than about 100 pM, in other embodiments have a $K_D$ of less than 50 pM, in other embodiments have a $K_D$ of less than 25 pM, in other embodiments have a $K_D$ of less than 10 pM, in other embodiments have a $K_D$ of less than 5 pM, in other embodiments have a $K_D$ of less than 3 pM, in other embodiments have a $K_D$ of less than 1 pM.

A number of methodologies are available for the measurement of binding affinity of an antibody to its antigens, one such methodology is KinExA™. The Kinetic Exclusion Assay (KinExA™.) is a general purpose immunoassay platform (basically a flow spectrofluorimeter) that is capable of measuring equilibrium dissociation constants, and association and dissociation rate constants for antigen/antibody interactions. Since KinExA™. is performed after equilibrium has been obtained, it is an advantageous technique to use for measuring the $K_D$ of high affinity interactions where the off-rate of the interaction may be very slow. The use of KinExA™. is particularly appropriate in this case where the affinity of antibody and antigen are higher than can be accurately predicted by surface plasmon resonance analysis. The KinExA™. methodology can be conducted as described in Drake et al (2004) Analytical Biochemistry 328, 35-43.

In one embodiment of the invention the binding members of the invention are specific for IL-1R with a $K_D$ of 300 pM or lower as measured using the KinExA™. methodology. Alternatively a $K_D$ of 200 pM or lower, 100 pM or lower, 50 pM or lower, 20 pM or lower or 10 pM or lower, 5 pM or lower, 3 pM or lower, 1 pM or lower.

Inhibition of biological activity may be partial or total. Binding members may inhibit an IL-1R1 biological activity, such as IL-1β induced IL-8 release in CYNOM-K1 cells or IL-1α and IL-1β induced IL-8 release in HeLa cells, by 100%, or alternatively by: at least 95%, at least 90%, at least 85%, at least 80%, at least 75%, at least 70%, at least 60%, or at least 50% of the activity of a concentration of IL-1α or β that induces 50% or 80% of the maximum possible activity in absence of the binding member.

The neutralizing potency of a binding member is normally expressed as an $IC_{50}$ value, in nM unless otherwise stated. In functional assays, $IC_{50}$ is the concentration of a binding member that reduces a biological response by 50% of its maximum. In ligand-binding studies, $IC_{50}$ is the concentration that reduces receptor binding by 50% of maximal specific binding level. $IC_{50}$ may be calculated by plotting % of maximal biological response as a function of the log of the binding member concentration, and using a software program, such as Prism (GraphPad Software Inc., La Jolla, Calif., USA) to fit a sigmoidal function to the data to generate $IC_{50}$ values. Potency may be determined or measured using one or more assays known to the skilled person and/or as described or referred to herein. The neutralizing potency of a binding member can be expressed as a Geomean.

Neutralisation of IL-1R1 activity by a binding member in an assay described herein, indicates that the binding member binds to and neutralizes IL-1R1. Other methods that may be used for determining binding of a binding member to IL-1R1 include ELISA, Western blotting, immunoprecipitation, affinity chromatography and biochemical assays.

A binding member of the invention may have a similar or stronger affinity for human IL-1R1 than for IL-1R1 of other species. Affinity of a binding member for human IL-1R1 may be, similar to or for example, within 5 or 10-fold that for cynomolgus monkey IL-1R1. Alternatively, a binding member may have a similar binding affinity for human and cynomolgus monkey IL-1R1.

A binding member of the invention comprises an IL-1R1 binding motif comprising one or more CDRs, e.g. a 'set of CDRs' within a framework. A set of CDRs comprises one or more CDRs selected from: HCDR1, HCDR2, HCDR3, LCDR1, LCDR2 and LCDR3. In one embodiment a set of CDRs comprises a HCDR3 in Table 2 optionally combined with one or more CDRs selected from: HCDR1, HCDR2, LCDR1, LCDR2 and LCDR3, for example one or more CDRs selected from: HCDR1, HCDR2, LCDR1, LCDR2 and LCDR3 in Table 2. In another embodiment of the invention a set of CDRs comprises a HCDR3 and a LCDR3 in Table 2 optionally combined with one or more CDRs selected from: HCDR1, HCDR2, LCDR1 and LCDR2, for example one or more CDRs selected from: HCDR1, HCDR2, LCDR1 and LCDR2 in Table 2. In another embodiment of the invention a set of CDRs comprises a HCDR1, HCDR2, HCDR3, LCDR1, LCDR2 and LCDR3 in Table 2. Whilst it is preferred to select the one or more CDRs from the same antibody in Table 2, CDRs may be selected from one or more antibodies listed in Table 2.

In another embodiment, a binding member of the invention, for example an antibody, comprises an IL-1R1 binding motif comprising one or more CDRs selected from: HCDR1, HCDR2, HCDR3, LCDR1, LCDR2 and LCDR3, for example as disclosed in Tables 1a and 1b, wherein said binding member specifically binds Il-1R1.

In another embodiment, a binding member of the invention, for example an antibody, comprises an IL-1R1 binding motif comprising one or more CDRs selected from: HCDR1, HCDR2, HCDR3, LCDR1, LCDR2 and LCDR3, for example as disclosed in Tables 1a and 1b, wherein said binding member specifically binds Il-1R1 and competes with IL-1β and IL-1Ra for binding to IL-1R1 and binds Il-1R1 with a $K_D$ of 10 pM or less when measured by Kinexa™.

As described herein, a parent antibody molecule was isolated having the set of CDR sequences as shown in Table 1a (see Antibody 1). Through a process of optimisation we generated a panel of antibody clones numbered 2-3, with CDR sequences derived from the parent CDR sequences and having modifications at the positions indicated, in Table 1. Thus, for example, it can be seen from Table 1a that Antibody 2 has the parent HCDR1, HCDR2, LCDR1 and LCDR2, and has a parent HCDR3 sequence in which: Kabat residue 100E is replaced with T, Kabul residue 100F is replaced with V, Kabat residue 100G is replaced with D, Kabat residue 100H is replaced with A, Kabat residue 100I is replaced with A, Kabat residue 101 is replaced with V and Kabat residue 102 is replaced with D.

As described herein, a second parent antibody molecule was isolated having the set of CDR sequences as shown in Table 1b (see Antibody 4). Through a process of optimisation we generated a panel of antibody clones numbered 5-10 with CDR sequences derived from the parent CDR sequences and having modifications at the positions indicated in Table 1b. Thus, for example, it can be seen from Table 1b that Antibody 5 has the parent HCDR1, HCDR2, LCDR1 and LCDR2, and has a parent HCDR3 sequence in which: Kabat residue 100A is replaced with A, Kabat residue 100B is replaced with P, Kabat residue 100C is replaced with P, Kabat residue 100D is replaced with P, Kabat residue 100E is replaced with L, Kabat residue 100F is replaced with G and Kabat residue 100I is replaced with G. It can also be seen from Table 1b that Antibody 6 has the parent HCDR1, HCDR2, LCDR1 and LCDR2, and has a parent HCDR3 sequence in which: Kabat residue 100A is replaced with E, Kabat residue 100B is replaced with Q, Kabat residue 100C is replaced with Y, Kabat residue 100D is replaced with G, Kabat residue 100E is replaced with V, Kabat residue 100F is replaced with V, Kabat residue 100J has been deleted, Kabat residue 101 is replaced with F and Kabat residue 102 is replaced with V.

Described herein is a binding member comprising the parent set of CDRs as shown in Table 1a (Antibody 1), in which HCDR1 is SEQ ID NO: 93 (Kabat residues 31-35), HCDR2 is SEQ ID NO: 94 (Kabat residues 50-65), HCDR3 is SEQ ID NO: 95 (Kabat residues 95-102), LCDR1 is SEQ ID NO: 98 (Kabat residues 24-34), LCDR2 is SEQ ID NO: 99 (Kabat residues 50-56) and LCDR3 is SEQ ID NO: 100 (Kabat residues 89-97). The binding member according to the invention may also be the parent binding member (Antibody 1) as shown in Table 1a, wherein one or more of the CDRs have one or more amino acid additions, substitutions, deletions, and/or insertions. In some embodiments, the binding member comprises a set of CDRs having from one to twelve additions, substitutions, deletions and/or insertions relative to the parent sequences of Antibody 1. In another embodiment from one to ten additions, substitutions, deletions and/or insertions relative to Antibody 1. In another embodiment from one to five additions, substitutions, deletions and/or insertions relative to the parent sequences of Antibody 1. In another embodiment one to three additions, substitutions, deletions and/or insertions relative to Antibody 1.

In certain embodiments the binding member of the invention comprises HCDR1, HCDR2, HCDR3, LCDR1, LCDR2, and LCDR3; wherein the HCDR3 has the amino acid sequence of SEQ ID NO: 95 optionally having from 1 to 7 amino acid additions, substitutions, deletions and/or insertions; and the LCDR3 has the amino acid sequence of SEQ ID NO: 100 optionally having from 1 to 5 amino acid additions, substitutions, deletions and/or insertions. In such embodiments, the HCDR1 may have the amino acid sequence SEQ ID NO: 93; the HCDR2 may have the amino acid sequence SEQ ID NO: 94; the LCDR1 may have the amino acid sequence SEQ ID NO: 98; and the LCDR2 may have the amino acid sequence SEQ ID NO: 99. Alternatively, the HCDR1, the HCDR2, the LCDR1, and the LCDR2 may also collectively have one or more amino acid additions, substitutions, deletions, and/or insertions relative to the parent sequences (Antibody 1), such as from one to ten substitutions.

Described herein is a binding member comprising the parent set of CDRs as shown in Table 1b (Antibody 4), in which HCDR1 is SEQ ID NO: 103 (Kabat residues 31-35), HCDR2 is SEQ ID NO: 104 (Kabat residues 50-65), HCDR3 is SEQ ID NO: 105 (Kabat residues 95-102), LCDR1 is SEQ ID NO: 108 (Kabat residues 24-34), LCDR2 is SEQ ID NO: 109 (Kabat residues 50-56) and LCDR3 is SEQ ID NO: 110 (Kabat residues 89-97). The binding member according to the invention may also be the parent binding member as shown in Table 1b, wherein one or more of the CDRs have one or more amino acid additions, substitutions, deletions, and/or insertions. In some embodiments, the binding member comprises a set of CDRs having from one to fifteen additions, substitutions, deletions and/or insertions relative to the parent sequences of Antibody 4. In another embodiment one to ten additions, substitutions, deletions and/or insertions relative to Antibody 4. In another embodiment form one to five additions, substitutions, deletions and/or insertions relative to the parent sequences of Antibody 4. In another embodiment one to three additions, substitutions, deletions and/or insertions relative to Antibody 4.

In certain embodiments the binding member of the invention comprises HCDR1, HCDR2, HCDR3, LCDR1, LCDR2, and LCDR3; wherein the HCDR3 has the amino acid sequence of SEQ ID NO: 105 optionally having from 1 to 9 amino acid additions, substitutions, deletions and/or insertions; and the LCDR3 has the amino acid sequence of SEQ ID NO: 110 optionally having from 1 to 6 amino acid additions, substitutions, deletions and/or insertions. In such embodiments, the HCDR1 may have the amino acid sequence SEQ ID NO: 103; the HCDR2 may have the amino acid sequence SEQ ID NO: 104; the LCDR1 may have the amino acid sequence SEQ ID NO: 108; and the LCDR2 may have the amino acid sequence SEQ ID NO: 109. Alternatively, the HCDR1, the HCDR2, the LCDR1, and the LCDR2 may also collectively have one or more amino acid additions, substitutions, deletions, and/or insertions relative to the parent sequences (Antibody 4), such as from one to ten substitutions.

Described herein is a binding member comprising the Antibody 6 set of CDRs as shown in Table 1b, in which HCDR1 is SEQ ID NO: 63 (Kabat residues 31-35), HCDR2 is SEQ ID NO: 64 (Kabat residues 50-65), HCDR3 is SEQ ID NO: 65 (Kabat residues 95-102), LCDR1 is SEQ ID NO: 68 (Kabat residues 24-34), LCDR2 is SEQ ID NO: 69 (Kabat residues 50-56) and LCDR3 is SEQ ID NO: 70 (Kabat residues 89-97). The binding member according to the invention may also be the Antibody 6 binding member as shown in Table 1b, wherein one or more of the CDRs have one or more amino acid additions, substitutions, deletions, and/or insertions. In some embodiments, the binding member comprises a set of CDRs having from one to seventeen additions, substitutions, deletions and/or insertions relative to the sequences of Antibody 6. In another embodiment one to ten additions, substitutions, deletions and/or insertions relative to Antibody 6. In another embodiment form one to five additions, substitutions, deletions and/or insertions relative to the sequences of Antibody 6. In another embodiment one to three additions, substitutions, deletions and/or insertions relative to Antibody 6. In another embodiment one to two additions, substitutions, deletions and/or insertions relative to Antibody 6. In another embodiment one additions, substitution, deletion or insertion relative to Antibody 6.

In certain embodiments the binding member of the invention comprises HCDR1, HCDR3, LCDR1, LCDR2, and LCDR3; wherein the HCDR3 has the amino acid sequence of SEQ ID NO: 65 optionally having from 1 to 11 amino acid additions, substitutions, deletions and/or insertions; and the LCDR3 has the amino acid sequence of SEQ ID NO: 70 optionally having from 1 to 6 amino acid additions, substitutions, deletions and/or insertions. In such embodiments, the HCDR1 may have the amino acid sequence SEQ ID NO: 63; the HCDR2 may have the amino acid sequence SEQ ID NO: 64; the LCDR1 may have the amino acid sequence SEQ ID NO: 68; and the LCDR2 may have the amino acid sequence SEQ ID NO: 69. Alternatively, the HCDR1, the HCDR2, the LCDR1, and the LCDR2 may also collectively have one or more amino acid additions, substitutions, deletions, and/or insertions relative to the sequences of Antibody 6, such as from one to ten substitutions.

A binding member of the invention may comprise one or a combination of CDRs as described herein. For example, the binding member of the invention may comprise an HCDR1 having the amino acid sequence of SEQ ID NO: 93; an HCDR2 having the amino acid sequence of SEQ ID NO: 94; an HCDR3 having an amino acid sequence selected from the group consisting of SEQ ID NOS: 95, 5 or 125; an LCDR1 having the amino acid sequence of SEQ ID NO: 98; an LCDR2 having the amino acid sequence SEQ ID NO: 99; and an LCDR3 having an amino acid sequence selected from the group consisting of SEQ ID NOS: 100, 10 or 130.

A binding member of the invention may comprise one or a combination of CDRs as described herein. For example, the binding member of the invention may comprise an HCDR1 having the amino acid sequence of SEQ ID NO: 103; an HCDR2 having the amino acid sequence of SEQ ID NO: 104; an HCDR3 having an amino acid sequence selected from the group consisting of SEQ ID NOS: 105, 15, 65, 25, 35, 75, 45, 115, 55 or 85; an LCDR1 having the amino acid sequence of SEQ ID NO: 108; an LCDR2 having the amino acid sequence SEQ ID NO: 109; and an LCDR3 having an amino acid sequence selected from the group consisting of SEQ ID NOS: 110, 20, 70, 30, 40, 80, 50, 120, 60 or 90.

A binding member of the invention may comprise one or a combination of CDRs as described herein. For example, the binding member of the invention may comprise an HCDR1 having the amino acid sequence of SEQ ID NO: 93; an HCDR2 having the amino acid sequence of SEQ ID NO: 94; an HCDR3 having an amino acid sequence selected from the group consisting of SEQ ID NOS:95, 5, 125; 105, 15, 65, 25, 35, 75, 45, 115, 55 or 85 an LCDR1 having the amino acid sequence of SEQ ID NO: 98 or 108; an LCDR2 having the amino acid sequence SEQ ID NO: 99 or 109; and an LCDR3 having an amino acid sequence selected from the group consisting of SEQ ID NOS: 100, 10, 130, 110, 20, 70, 30, 40, 80, 50, 120, 60 or 90.

In certain embodiments, the binding member or VH domain of the invention comprises an Antibody 1 HCDR3 (SEQ ID NO:95) with one or more of the following substitutions or deletions:
Kabat residue 100E replaced by T;
Kabat residue 100F replaced V or L;
Kabat residue 100G replaced by D;
Kabat residue 100H replaced by A or P;
Kabat residue 100I replaced by A or P;
Kabat residue 101 replaced by V or G;
Kabat residue 102 replaced by D or V;

In certain embodiments, the binding member or VH domain of the invention comprises an Antibody 4 HCDR3 (SEQ ID NO:105) with one or more of the following substitutions or deletions:
Kabat residue 100A replaced by A or E;
Kabat residue 100B replaced P, Q, or A;
Kabat residue 100C replaced by P, Y, S or L;
Kabat residue 100D replaced by P, G or A;
Kabat residue 100E replaced by L or V;
Kabat residue 100F replaced by G, V or P;
Kabat residue 100G replaced by V;
Kabat residue 100H replaced by Y;
Kabat residue 100I replaced by G or D;
Kabat residue 100J replaced by A or deleted;
Kabat residue 101 replaced by F;
Kabat residue 102 replaced by V.

In some embodiments, a binding member, or a VL domain thereof may comprise the Antibody 1 LCDR3 (SEQ ID NO 100) with one or more of the following substitutions:
Kabat residue 94 replaced by H or A;
Kabat residue 95 replaced by A;
Kabat residue 95A replaced by E or R;
Kabat residue 95B replaced by Q or V;
Kabat residue 97 replaced by H or L.

In some embodiments, a binding member, or a VL domain thereof may comprise the Antibody 4 LCDR3 (SEQ ID NO 110) with one or more of the following substitutions:
Kabat residue 94 replaced by A, V, D, H, L or R;
Kabat residue 95 replaced by G, R or A;
Kabat residue 95A replaced by G, L, A, V or D;
Kabat residue 95B replaced by H, R, A or D;
Kabat residue 96 replaced by H, P or A.
Kabat residue 97 replaced by H, V or Q.

In certain embodiments, the binding member or VH domain of the invention comprises an Antibody 6 HCDR3 (SEQ ID NO:65) with one or more of the following substitutions or additions:
Kabat residue 100A replaced by G or A;
Kabat residue 100B replaced S, P or A;
Kabat residue 100C replaced by D, P, S L;
Kabat residue 100D replaced by Y, P or A;
Kabat residue 100E replaced by T or L;
Kabat residue 100F replaced by T, G or P;
Kabat residue 100G replaced by V;
Kabat residue 100H replaced by Y;
Kabat residue 100I replaced by G or D;
Kabat residue 100J deleted in Antibody 6 is reinstated as a A or F;
Kabat residue 101 replaced by D;
Kabat residue 102 replaced by I.

In some embodiments, a binding member, or VL domain thereof may comprise the Antibody 6 LCDR3 (SEQ ID NO 70) with one or more of the following substitutions:
Kabat residue 94 replaced by S, A, D, H, L or R;
Kabat residue 95 replaced by L, G or A;
Kabat residue 95A replaced by S, G, A, V or D;
Kabat residue 95B replaced by R, A or D;
Kabat residue 96 replaced by S, P or A.
Kabat residue 97 replaced by L, H or Q.

In one embodiment, the invention is a binding member comprising a set of CDRs in which: HCDR1 has amino acid sequence SEQ ID NO: 3, HCDR2 has amino acid sequence SEQ ID NO: 4, HCDR3 has amino acid sequence SEQ ID NO: 5, LCDR1 has amino acid sequence SEQ ID NO: 8, LCDR2 has amino acid sequence SEQ ID NO: 9, and LCDR3 has amino acid sequence SEQ ID NO: 10.

In one embodiment, the invention is a binding member comprising a set of CDRs in which: HCDR1 has amino acid sequence SEQ ID NO: 63, HCDR2 has amino acid sequence SEQ ID NO: 64, HCDR3 has amino acid sequence SEQ ID NO: 65, LCDR1 has amino acid sequence SEQ ID NO: 68, LCDR2 has amino acid sequence SEQ ID NO: 69, and LCDR3 has amino acid sequence SEQ ID NO: 70.

In one embodiment, the invention is a binding member comprising a set of CDRs in which: HCDR1 has amino acid sequence SEQ ID NO: 23, HCDR2 has amino acid sequence SEQ ID NO: 24, HCDR3 has amino acid sequence SEQ ID NO: 25, LCDR1 has amino acid sequence SEQ ID NO: 28, LCDR2 has amino acid sequence SEQ ID NO: 29, and LCDR3 has amino acid sequence SEQ ID NO: 20.

In one embodiment, the invention is a binding member comprising a set of CDRs in which: HCDR1 has amino acid sequence SEQ ID NO: 113, HCDR2 has amino acid sequence SEQ ID NO: 114, HCDR3 has amino acid sequence SEQ ID NO: 115, LCDR1 has amino acid sequence SEQ ID NO: 118, LCDR2 has amino acid sequence SEQ ID NO: 119, and LCDR3 has amino acid sequence SEQ ID NO: 120.

In one embodiment, the invention is a binding member comprising a set of CDRs in which: HCDR1 has amino acid sequence SEQ ID NO: 53, HCDR2 has amino acid sequence SEQ ID NO: 54, HCDR3 has amino acid sequence SEQ ID NO: 55, LCDR1 has amino acid sequence SEQ ID NO: 58, LCDR2 has amino acid sequence SEQ ID NO: 59, and LCDR3 has amino acid sequence SEQ ID NO: 60.

A binding member of the invention may be one which competes or cross-competes for binding to IL-1R1 with any binding member disclosed herein which both binds IL-1R1 and comprises a binding member such as VH and/or VL domain, CDR e.g. HCDR3, and/or set of CDRs disclosed herein, for example the antibodies disclosed in Table 2. Competition between binding members may be assayed easily in vitro, for example using ELISA and/or by tagging a specific reporter molecule to one binding member which can be detected in the presence of one or more other untagged binding members, to enable identification of binding members which bind the same epitope or an overlapping epitope. Such methods are readily known to one of ordinary skill in the art, and are described in more detail herein. Thus, a further aspect of the present invention provides a binding member specific for IL-1R1 that competes or cross-competes for binding to human IL-1R1 with an antibody molecule comprising a VH and/or VL domain or a CDR e.g. HCDR3 or set of CDRs of any of antibodies 1 to 10. In one embodiment, the binding member of the invention competes or cross-competes with Antibody 1 and/or Antibody 3 of Table 2.

Another embodiment of the invention provides binding members which bind to a specific region of IL-1R1, for example an epitope. Specifically the same epitope or part thereof as is bound by any one of the antibodies listed in Table 2.

Another embodiment of the invention provides an isolated binding member which binds an epitope comprised within one or more of the following sequences of Il-1R1:
(i) N123-V134;
(ii) L140-K157; and/or
(iii) K178-R180.

Another embodiment of the invention provides an isolated binding member specific for IL-1R1 according to Claim 16 which binds a discontinuous epitope comprised within the following sequences of IL-1R1:
   (i) N123-V134;
   (ii) L140-K157; and
   (iii) K178-R180.

In further aspects the present invention provides a binding member comprising a human antibody antigen-binding site which competes or cross-competes with an antibody antigen-binding site for binding to human IL-1R1, wherein the antibody antigen-binding site is composed of a VH domain and a VL domain, and wherein the VH and VL domains comprise a set of CDRs of the parent (Antibody 1 or Antibody 4), or of any of antibodies 2 to 3 or 5 to 10 list in Table 2.

Any suitable method may be used to determine the sequence of residues bound by a binding member. For example, a peptide-binding scan may be used, such as a PEPSCAN-based enzyme linked immuno assay (ELISA). In a peptide-binding scan, such as the kind provided by PEP-SCAN Systems, short overlapping peptides derived from the antigen are systematically screened for binding to a binding member. The peptides may be covalently coupled to a support surface to form an array of peptides. Peptides may be in a linear or constrained conformation. A constrained conformation may be produced using peptides having a terminal Cys residue at each end of the peptide sequence. The Cys residues can be covalently coupled directly or indirectly to a support surface such that the peptide is held in a looped conformation. Thus, peptides used in the method may have Cys residues added to each end of a peptide sequence corresponding to a fragment of the antigen. Double looped peptides may also be used, in which a Cys residue is additionally located at or near the middle of the peptide sequence. The Cys residues can be covalently coupled directly or indirectly to a support surface such that the peptides form a double-looped conformation, with one loop on each side of the central Cys residue. Peptides can be synthetically generated, and Cys residues can therefore be engineered at desired locations, despite not occurring naturally in the IL-1R1 sequence. Optionally, linear and constrained peptides may both be screened in a peptide-binding assay. A peptide-binding scan may involve identifying (e.g. using ELISA) a set of peptides to which the binding member binds, wherein the peptides have amino acid sequences corresponding to fragments of IL-1R (e.g. peptides of about 5, 10 or 15 contiguous residues of IL-1R1), and aligning the peptides in order to determine a footprint of residues bound by the binding member, where the footprint comprises residues common to overlapping peptides.

Alternatively or additionally the peptide-binding scan method may involve identifying peptides to which the binding member binds with at least a given signal:noise ratio. Details of a suitable peptide-binding scan method for determining binding are known in the art. Other methods that are well known in the art and that could be used to determine the residues bound by an antibody, and/or to confirm peptide-binding scan results, include site directed mutagenesis, hydrogen deuterium exchange, mass spectrometry, NMR, and X-ray crystallography.

A binding member of the invention may be an antibody molecule or binding fragment thereof, preferably a human antibody molecule or a humanized antibody molecule or binding fragment thereof. The antibodies may be monoclonal antibodies, especially of human, murine, chimeric or humanized origin, which can be obtained according to the standard methods well known to the person skilled in the art.

Although, as noted below, CDRs can be carried by non-antibody scaffolds, the structure for carrying a CDR or a set of CDRs of the invention will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat, et al., 1987 [36], and updates thereof findable under "Kabat" using any internet search engine.

An antibody of the invention normally comprises an antibody VH and/or VL domain. A VH domain of the invention comprises a set of HCDRs, and a VL domain comprises a set of LCDRs. An antibody molecule may comprise an antibody VH domain comprising a VH CDR1, CDR2 and CDR3 and a framework. It may alternatively or also comprise an antibody VL domain comprising a VL CDR1, CDR2 and CDR3 and a framework. AB example of an antibody VH domain of the invention is SEQ ID NO. 22, and an example of an antibody VL domain of the invention is SEQ ID NO. 27.

The invention provides binding members comprising a HCDR1 and/or HCDR2 and/or HCDR3 of any of antibodies in Table 2 and/or an LCDR1 and/or LCDR2 and/or LCDR3 of any of antibodies in Table 2. The binding member may comprise a set of VH CDRs, optionally it may also comprise a set of VL CDRs, and the VL CDRs may be from the same or a different antibody as the VH CDRs.

Typically, a VH domain is paired with a VL domain to provide an antibody antigen-binding site, although as discussed further below a VH or VL domain alone may be used to bind antigen. For example, the Antibody 1 VH domain (see Table 2) may be paired with the Antibody 1 VL domain, so that an antibody antigen-binding site is formed comprising both the antibody 1 VH and VL domains. Analogous embodiments are provided for the other VH and VL domains disclosed herein. In other embodiments, the Antibody 1 VH is paired with a VL domain other than the Antibody 1. Light-chain promiscuity is well established in the art. Again, analogous embodiments are provided by the invention for the other VH and VL domains disclosed herein. Thus, the VH of any of the antibodies in Table 2 may be paired with the VL of the same or any other antibodies in Table 2.

A further aspect of the invention is an antibody molecule comprising a VH domain that has at least 60, 70, 80, 85, 90, 95, 98 or 99% amino acid sequence identity with a VH domain of any of antibodies shown in Table 2, or comprising a set of HCDRs (e.g., HCDR1, HCDR2, and/or HCDR3) shown in Table 1a or 1b. The antibody molecule may optionally also comprise a VL domain that has at least 60, 70, 80, 85, 90, 95, 98 or 99% amino acid sequence identity with a VL domain of any of the antibodies 1 to 28, or with a set of LCDRs (e.g. LCDR1, LCDR2, and/or LCDR3) shown in Table 1a or 1b. Algorithms that can be used to calculate % identity of two amino acid sequences include e.g. BLAST [37], FASTA [38], or the Smith-Waterman algorithm [39], e.g. employing default parameters.

Binding members of the present invention may further comprise antibody constant regions or parts thereof, e.g. human antibody constant regions or parts thereof. For example, a VL domain may be attached at its C-terminal end to antibody light chain constant domains including human Cκ or Cλ chains. Similarly, a binding member based on a VH domain may be attached at its C-terminal end to all or part (e.g. a CH1 domain) of an immunoglobulin heavy chain derived from any antibody isotype, e.g. IgG, IgA, IgE and IgM and any of the isotype sub-classes, particularly IgG1, IgG2, IgG3 and IgG4. IgG1 is advantageous due to its ease of manufacture and stability, e.g., half-life. Any synthetic or other constant region variants which modulate binding member function and/or properties e.g. stabilizing variable regions, may also be useful in the present invention.

Furthermore, it may be desired according to the present invention to modify the amino acid sequences described herein, in particular those of human heavy chain constant regions to adapt the sequence to a desired allotype, e.g. an allotype found in the Caucasian population.

A binding member may comprise an antibody molecule, or binding fragment thereof, having one or more CDRs, e.g. a set of CDRs, within an antibody framework. For example, one or more CDRs or a set of CDRs of an antibody may be grafted into a framework (e.g. human framework) to provide an antibody molecule. The framework regions may be of human germline gene sequences, or be non-germlined. Thus, the framework may be germlined where one or more residues within the framework are changed to match the residues at the equivalent position in the most similar human germline framework. Thus, a binding member of the invention may be an isolated human antibody molecule having VH domain comprising a set of HCDRs in a human germline framework, e.g. human germline IgG VH framework. The binding member also has a VL domain comprising a set of LCDRs, e.g. in a human germline IgG VL framework.

VH and/or VL framework residues may be modified as discussed and exemplified herein e.g. using site-directed mutagenesis. A VH or VL domain according to the invention, or a binding member comprising such a VL domain, preferably has the VH and/or VL domain sequence of an antibody of Table 2 and comprising a HCDR3 of the invention.

A non-germlined antibody molecule has the same CDRs, but different frameworks, compared to a germlined antibody molecule. Germlined antibodies may be produced by germlining framework regions of the VH and VL domain sequences shown herein for these antibodies.

Alterations may be made in one or more framework regions and/or one or more CDRs. The alterations normally do not result in loss of function, so a binding member comprising a thus-altered amino acid sequence should retain an ability to bind and/or neutralize IL-1R1. It may retain the same quantitative binding and/or neutralizing ability as a binding member in which the alteration is not made, e.g. as measured in an assay described herein. The binding member comprising a thus-altered amino acid sequence may have an improved ability to bind and/or neutralize IL-1R1.

Alteration may comprise replacing one or more amino acid residue(s) with a non-naturally occurring or non-standard amino acid, modifying one or more amino acid residue into a non-naturally occurring or non-standard form, or inserting one or more non-naturally occurring or non-standard amino acid into the sequence. Examples of numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring. Several naturally occurring non-standard amino acids are known in the art, such as 4-hydroxyproline, 5-hydroxylysine, 3-methylhistidine, N-acetylserine, etc. [40]. Those amino acid residues that are derivatised at their N-alpha position will only be located at the N-terminus of an amino-acid sequence. Normally in the present invention an amino acid is an L-amino acid, but it may be a D-amino acid. Alteration may therefore comprise modifying an L-amino acid into, or replacing it with, a D-amino acid. Methylated, acetylated and/or phosphorylated forms of amino acids are also known, and amino acids in the present invention may be subject to such modification.

Amino acid sequences in antibody domains and binding members of the invention may comprise non-natural or non-standard amino acids described above. Non-standard amino acids (e.g. D-amino acids) may be incorporated into an amino acid sequence during synthesis, or by modification or replacement of the "original" standard amino acids after synthesis of the amino acid sequence.

Use of non-standard and/or non-naturally occurring amino acids increases structural and functional diversity, and can thus increase the potential for achieving desired IL-1R1-binding and neutralizing properties in a binding member of the invention. Additionally, D-amino acids and analogues have been shown to have better pharmacokinetic profiles compared with standard L-amino acids, owing to in vivo degradation of polypeptides having L-amino acids after administration to an animal e.g. a human.

Novel VH or VL regions carrying CDR-derived sequences of the invention may be generated using random mutagenesis of one or more selected VH and/or VL genes to generate mutations within the entire variable domain. Such a technique is described by Gram et al. [41], who used error-prone PCR. In some embodiments one or two amino acid substitutions are made within an entire variable domain or set of CDRs.

Another method that may be used is to direct mutagenesis to CDR regions of VH or VL genes. Such techniques are disclosed by Barbas et al. [42] and Schier et al. [43].

All the above-described techniques are known as such in the art and the skilled person will be able to use such techniques to provide binding members of the invention using routine methodology in the art.

A further aspect of the invention provides a method for obtaining an antibody antigen-binding site for IL-1R1, the method comprising providing by way of addition, deletion, substitution or insertion of one or more amino acids in the amino acid sequence of a VH domain set out herein, optionally combining the VH domain thus provided with one or more VL domains, and testing the VH domain or VH/VL combination or combinations to identify a binding member or an antibody antigen-binding site for IL-1R1 and optionally with one or more desired properties, e.g. ability to neutralize IL-1R1 activity. Said VL domain may have an amino acid sequence which is substantially as set out herein. An analogous method may be employed in which one or more sequence variants of a VL domain disclosed herein are combined with one or more VH domains.

Variable domain amino acid sequence variants of any of the VH and VL domains whose sequences are specifically disclosed herein may be employed in accordance with the present invention, as discussed. Particular variants may include one or more amino acid sequence alterations (addition, deletion, substitution and/or insertion of an amino acid residue). In certain embodiments, the variants have less than about 20, less than 15, less than 10 or less than 5 such alterations.

As noted above, a CDR amino acid sequence substantially as set out herein may be carried as a CDR in a human antibody variable domain or a substantial portion thereof. The HCDR3 sequences substantially as set out herein represent embodiments of the present invention and each of these may be carried as a HCDR3 in a human heavy chain variable domain or a substantial portion thereof, optionally in combination with a HCDR1, HCDR2, LCDR1, LCDR2 and/or LCDR3 of the invention.

Binding members of the invention also include fragments of antibodies that comprise an antibody antigen binding site. Fragments of an antibody are produced by recombinant DNA techniques, or by enzymatic or chemical cleavage of intact antibodies. Antibody fragments that comprise an antibody antigen-binding site include, but are not limited to, molecules such as Fab, Fab', Fab'-SH, scFv, Fv, dAb, Fd and disulphide stabilized variable region (dsFv). Various other antibody molecules including one or more antibody antigen-binding sites have been engineered, including for example $Fab_2$, $Fab_3$, diabodies, triabodies, tetrabodies and minibodies. Antibody molecules and methods for their construction and use are described in Holliger & Hudson (44).

It has been shown that fragments of a whole antibody can perform the function of binding antigens. Examples of binding fragments are (i) the Fab fragment consisting of VL, VH, constant light chain domain (CL) and constant heavy chain domain 1 (CH1) domains; (ii) the Fd fragment consisting of the VH and CH1 domains; (iii) the Fv fragment consisting of the VL and VH domains of a single antibody; (iv) the dAb fragment [45, 46, 47], which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site [48, 49]; (viii) bispecific single chain Fv dimers (for example as disclosed in WO 1993/011161) and (ix) "diabodies", multivalent or multispecific fragments constructed by gene fusion (for example as disclosed in WO94/13804 and [50]). Fv, scFv or diabody molecules may be stabilized by the incorporation of disulphide bridges linking the VH and VL domains [51]. Minibodies comprising a say joined to a CH3 domain may also be made [52]. Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

Antibody fragments of the invention can be obtained starting from a parent antibody molecule (Antibody 1 or 4) or any of the antibody molecules 2, 3, 5 to 10, by methods such as digestion by enzymes e.g. pepsin or papain and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers, such as those supplied by for example the company Applied Biosystems Inc (Foster City, Calif., USA), or by nucleic acid synthesis and expression.

Functional antibody fragments according to the present invention include any functional fragment whose half-life is increased by a chemical modification, for example by PEGylation, or by incorporation in a liposome.

A dAb (domain antibody) is a small monomeric antigen-binding fragment of an antibody, namely the variable region of an antibody heavy or light chain [47]. VH dAbs occur naturally in camelids (e.g. camel, llama) and may be produced by immunizing a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. Camelid VH dAbs are being developed for therapeutic use under the name "Nanobodies™". A binding member of the present invention may be a dAb comprising a VH or VL domain substantially as set out herein, or a VH or VL domain comprising a set of CDRs substantially as set out herein.

Antibodies of the invention include bispecific antibodies. Bispecific or bifunctional antibodies form a second generation of monoclonal antibodies in which two different variable regions are combined in the same molecule [53]. Their use has been demonstrated both in the diagnostic field and in the therapy field from their capacity to recruit new effector functions or to target several molecules on the surface of tumour cells. Where bispecific antibodies are to be used, these may be conventional bispecific antibodies, which can be manufactured in a variety of ways [54], e.g. prepared chemically or from hybrid hybridomas, or may be any of the bispecific antibody fragments mentioned above. These antibodies can be obtained by chemical methods [55, 56] or somatic methods

[57, 58] but likewise and preferentially by genetic engineering techniques which allow the heterodimerization to be forced and thus facilitate the process of purification of the antibody sought [59]. Examples of bispecific antibodies include those of the BiTE™ technology in which the binding domains of two antibodies with different specificity can be used and directly linked via short flexible peptides. This combines two antibodies on a short single polypeptide chain. Diabodies and say can be constructed without an Fc region, using only variable domains, potentially reducing the effects of anti-idiotypic reaction.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because they can be readily constructed and expressed in *E. coli*. Diabodies (and many other polypeptides, such as antibody fragments) of appropriate binding specificities can be readily selected using phage display (WO 1994/13804) from libraries. If one arm of the diabody is to be kept constant, for instance, with a specificity directed against IL-1R1, then a library can be made where the other arm is varied and an antibody of appropriate specificity selected. Bispecific whole antibodies may be made by alternative engineering methods as described in Ridgeway et al. [60] or a described in WO 1996/27011, WO 1998/50431 and WO 2006/028936.

Alternatively, a binding member of the invention may comprise an antigen-binding site within a non-antibody molecule, normally provided by one or more CDRs e.g. a set of CDRs in a non-antibody protein scaffold, as discussed further below.

An antigen binding site may be provided by means of arrangement of CDRs on non-antibody protein scaffolds, such as fibronectin or cytochrome B etc. [61, 62, 63], or by randomizing or mutating amino acid residues of a loop within a protein scaffold to confer binding specificity for a desired target. Scaffolds for engineering novel binding sites in proteins have been reviewed in detail by Nyaren et al. [63]. Protein scaffolds for antibody mimics are disclosed in WO200034784, which is herein incorporated by reference in its entirety, in which the inventors describe proteins (antibody mimics) that include fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties, such as an ability to enter cells, penetrate deep into tissues or reach targets within other structures, or to bind within protein cavities of the target antigen. Use of antigen binding sites in non-antibody protein scaffolds is reviewed in Wess, 2004 [64]. Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from *S. aureus*, transferrin, tetranectin, fibronectin (e.g. 10th fibronectin type III domain), lipocalins as well as gamma-crystalline and other Affilin™ scaffolds (Scil Proteins). Examples of other approaches include synthetic "Microbodies" based on cyclotides—small proteins having intra-molecular disulphide bonds, Microproteins (Versabodies™, Amunix Inc, Mountain View, Calif., USA) and ankyrin repeat proteins (DARPins, Molecular Partners AG, Zürieh-Schlieren, Switzerland). Such proteins also include small, engineered protein domains such as, for example, immuno-domains (see for example, U.S. Patent Publication Nos. 2003/082630 and 2003/157561). Immuno-domains contain at least one complementarily determining region (CDR) of an antibody.

A binding member according to the present invention may comprise other amino acids, e.g. forming a peptide or polypeptide, such as a folded domain, or to impart to the molecule another functional characteristic in addition to ability to bind antigen. Binding members of the invention may carry a detectable label, or may be conjugated to a toxin or a targeting moiety or enzyme (e.g. via a peptidyl bond or linker). For example, a binding member may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

The invention also comprises binding members which have been modified to change, i.e. increase, decrease or eliminate, the biological effect function of the binding members, for example antibodies with modified Fc regions. In some embodiments, the binding members or antibodies as disclosed herein can be modified to enhance their capability of fixing complement and participating in complement-dependent cytotoxicity (CDC). In other embodiments, the binding members or antibodies can be modified to enhance their capability of activating effector cells and participating in antibody-dependent cytotoxicity (ADCC). In yet other embodiments, the binding members or antibodies as disclosed herein can be modified both to enhance their capability of activating effector cells and participating in antibody-dependent cytotoxicity (ADCC) and to enhance their capability of fixing complement and participating in complement-dependent cytotoxicity (CDC).

In some embodiments, the binding members or antibodies as disclosed herein can be modified to reduce their capability of fixing complement and participating in complement-dependent cytotoxicity (CDC). In other embodiments, the binding members or antibodies can be modified to reduce their capability of activating effector cells and participating in antibody-dependent cytotoxicity (ADCC). In yet other embodiments, the binding members or antibodies as disclosed herein can be modified both to reduce their capability of activating effector cells and participating in antibody-dependent cytotoxicity (ADCC) and to reduce their capability of fixing complement and participating in complement-dependent cytotoxicity (CDC).

In certain embodiments, the half-life of a binding member or antibody as disclosed herein and of compositions of the invention is at least about 4 to 7 days. In certain embodiments, the mean half-life of a binding member or antibody as disclosed herein and of compositions of the invention is at least about 2 to 5 days, 3 to 6 days, 4 to 7 days, 5 to 8 days, 6 to 9 days, 7 to 10 days, 8 to 11 days, 8 to 12, 9 to 13, 10 to 14, 11 to 15, 12 to 16, 13 to 17, 14 to 18, 15 to 19, or 16 to 20 days. In other embodiments, the mean half-life of a binding member or antibody as disclosed herein and of compositions of the invention is at least about 17 to 21 days, 18 to 22 days, 19 to 23 days, 20 to 24 days, 21 to 25 days, 22 to 26 days, 23 to 27 days, 24 to 28 days, 25 to 29 days, or 26 to 30 days. In still further embodiments the half-life of a binding member or antibody as disclosed herein and of compositions of the invention can be up to about 50 days. In certain embodiments, the half-lives of antibodies and of compositions of the invention can be prolonged by methods known in the art. Such prolongation can in turn reduce the amount and/or frequency of dosing of the antibody compositions. Antibodies with improved in vivo half-lives and methods for preparing them are disclosed in U.S. Pat. No. 6,277,375; and International Publication Nos. WO 1998/23289 and WO 1997/3461.

In another embodiment, the invention provides an article of manufacture including a container. The container includes a composition containing a binding member or antibody as disclosed herein, and a package insert or label indicating that the composition can be used to treat disorder associated with IL-1R1.

In other embodiments, the invention provides a kit comprising a composition containing a binding member or antibody as disclosed herein, and instructions to administer the composition to a subject in need of treatment.

The present invention provides formulation of proteins comprising a variant Fc region. That is, a non-naturally occurring Fc region, for example an Fc region comprising one or more non naturally occurring amino acid residues. Also encompassed by the variant Fc regions of present invention are Fc regions which comprise amino acid deletions, additions and/or modifications.

The serum half-life of proteins comprising Fc regions may be increased by increasing the binding affinity of the Fc region for FcRn. In one embodiment, the Fc variant protein has enhanced serum half life relative to comparable molecule.

In another embodiment, the present invention provides an Fc variant, wherein the Fc region comprises at least one non naturally occurring amino acid at one or more positions selected from the group consisting of 239, 330 and 332, as numbered by the EU index as set forth in Kabat. In a specific embodiment, the present invention provides an Fc variant, wherein the Fc region comprises at least one non naturally occurring amino acid selected from the group consisting of 239D, 330L and 332E, as numbered by the EU index as set forth in Kabat. Optionally, the Fc region may further comprise additional non-naturally occurring amino acid at one or more positions selected from the group consisting of 252, 254, and 256, as numbered by the EU index as set forth in Kabat. In a specific embodiment, the present invention provides an Fc variant, wherein the Fc region comprises at least one non naturally occurring amino acid selected from the group consisting of 239D, 330L and 332E, as numbered by the EU index as set forth in Kabat and at least one non naturally occurring amino acid at one or more positions selected from the group consisting of 252Y, 254T and 256E, as numbered by the EU index as set forth in Kabat.

In another embodiment, the present invention provides an Fc variant, wherein the Fc region comprises at least one non naturally occurring amino acid at one or more positions selected from the group consisting of 234, 235 and 331, as numbered by the EU index as set forth in Kabat. In a specific embodiment, the present invention provides an Fc variant, wherein the Fc region comprises at least one non naturally occurring amino acid selected from the group consisting of 234F, 235F, 235Y, and 331S, as numbered by the EU index as set forth in Kabat. In a further specific embodiment, an Fc variant of the invention comprises the 234F, 235F, and 331S non naturally occurring amino acid residues, as numbered by the EU index as set forth in Kabat. In another specific embodiment, an Fc variant of the invention comprises the 234F, 235Y, and 331S non naturally occurring amino acid residues, as numbered by the EU index as set forth in Kabat. In another specific embodiment, the present invention provides an Fc variant, wherein the Fc region comprises at least one non naturally occurring amino acid selected from the group consisting of 234F, 235E and 331S, as numbered by the EU index as set forth in Kabat. In another specific embodiment, the present invention provides an Fc variant, wherein the Fc region comprises the non naturally occurring amino acid consisting of 234F, 235E and 331S, as numbered by the EU index as set forth in Kabat. Optionally, the Fc region may further comprise additional non naturally occurring amino acid at one or more positions selected from the group consisting of 252, 254, and 256, as numbered by the EU index as set forth in Kabat. In a specific embodiment, the present invention provides an Fc variant, wherein the Fc region comprises at least one non naturally occurring amino acid selected from the group consisting of 234F, 235F, 235Y, and 331S, as numbered by the EU index as set forth in Kabat; and at least one non naturally occurring amino acid at one or more positions are selected from the group consisting of 252Y, 254T and 256E, as numbered by the EU index as set forth in Kabat.

In another embodiment, the present invention provides an Fc variant protein formulation, wherein the Fc region comprises at least a non naturally occurring amino acid at one or more positions selected from the group consisting of 239, 330 and 332, as numbered by the EU index as set forth in Kabat. In a specific embodiment, the present invention provides an Fc variant protein formulation, wherein the Fc region comprises at least one non naturally occurring amino acid selected from the group consisting of 239D, 330L, and 332E, as numbered by the EU index as set forth in Kabat. Optionally, the Fc region may further comprise additional non naturally occurring amino acid at one or more positions selected from the group consisting of 252, 254, and 256, as numbered by the EU index as set forth in Kabat. In a specific embodiment, the present invention provides an Fc variant protein formulation, wherein the Fc region comprises at least one non naturally occurring amino acid selected from the group consisting of 239D, 330L and 332E, as numbered by the EU index as set forth in Kabat and at least one non naturally occurring amino acid at one or more positions are selected from the group consisting of 252Y, 254T and 256E, as numbered by the EU index as set forth in Kabat.

In another embodiment, the present invention provides an Fc variant protein formulation, wherein the Fc region comprises at least one non naturally occurring amino acid at one or more positions selected from the group consisting of 234, 235 and 331, as numbered by the EU index as set forth in Kabat. In a specific embodiment, the present invention provides an Fc variant protein formulation, wherein the Fc region comprises at least one non naturally occurring amino acid selected from the group consisting of 234F, 235F, 235Y, and 331S, as numbered by the EU index as set forth in Kabat. Optionally, the Fc region may further comprise additional non naturally occurring amino acid at one or more positions selected from the group consisting of 252, 254, and 256, as numbered by the EU index as set forth in Kabat. In a specific embodiment, the present invention provides an Fc variant protein formulation, wherein the Fc region comprises at least one non naturally occurring amino acid selected from the group consisting of 234F, 235F, 235Y, and 331S, as numbered by the EU index as set forth in Kabat; and at least one non naturally occurring amino acid at one or more positions are selected from the group consisting of 252Y, 254T and 256E, as numbered by the EU index as set forth in Kabat.

Methods for generating non naturally occurring Fc regions are known in the art. For example, amino acid substitutions and/or deletions can be generated by mutagenesis methods, including, but not limited to, site-directed mutagenesis (Kunkel, *Proc. Natl. Acad. Sci.* USA 82:488-492 (1985)), PCR mutagenesis (Higuchi, "PCR Protocols: A Guide to Methods and Applications", Academic Press, San Diego, pp. 177-183 (1990)), and cassette mutagenesis (Wells et al., Gene 34:315-323 (1985)). Preferably, site-directed mutagenesis is performed by the overlap-extension PCR method (Higuchi, in "PCR Technology: Principles and Applications for DNA Amplification", Stockton Press, New York, pp. 61-70 (1989)). The technique of overlap-extension PCR (Higuchi, ibid.) can also be used to introduce any desired mutation(s) into a target sequence (the starting DNA). For example, the first round of PCR in the overlap-extension method involves amplifying the target sequence with an outside primer (primer 1) and an internal mutagenesis primer (primer 3), and separately with a second outside primer (primer 4) and an internal primer (primer 2), yielding two PCR segments (segments A and B). The internal mutagenesis primer (primer 3) is designed to contain mismatches to the target sequence specifying the desired mutation(s). In the second round of PCR, the products of the first round of PCR (segments A and B) are amplified by PCR using the two outside primers (primers 1 and 4). The resulting full-length PCR segment (segment C) is digested with restriction enzymes and the resulting restriction fragment is cloned into an appropriate vector. As the first step of mutagenesis, the starting DNA (e.g., encoding an Fc fusion protein, an antibody or simply an Fc region), is operably cloned into a mutagenesis vector. The primers are designed to reflect the desired amino acid substitution. Other methods useful for the generation of variant Fc regions are known in the art (see, e.g., U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 6,821,505; 6,277,375; U.S. Patent Publication Nos. 2004/0002587 and PCT Publications WO 94/29351; WO 99/58572; WO 00/42072; WO 02/060919; WO 04/029207; WO 04/099249; WO 04/063351; WO 06/23403).

In some embodiments of the invention, the glycosylation patterns of the antibodies provided herein are modified to enhance ADCC and CDC effector function. See Shields R L et al., (2002) JBC. 277:26733; Shinkawa T et al., (2003) JBC. 278:3466 and Okazaki A et al., (2004) J. Mol. Biol., 336: 1239. In some embodiments, an Fc variant protein comprises one or more engineered glycoforms, i.e., a carbohydrate composition that is covalently attached to the molecule comprising an Fc region. Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, Nat. Biotechnol 17:176-180; Davies et al., 20017 Biotechnol Bioeng 74:288-294; Shields et al, 2002, J Biol Chem 277:26733-26740; Shinkawa et al., 2003, J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A PCT WO 02/311140A1; PCT WO 02/30954A1; Potillegent™ technology (Biowa, Inc. Princeton, N.J.); GlycoMAb™ glycosylation engineering technology (Glycart Biotechnology AG, Zurich, Switzerland). See, e.g., WO 00/061739; EA01229125; US 20030115614; Okazaki et al., 2004, JMB, 336: 1239-49.

It is also known in the art that the glycosylation of the Fc region can be modified to increase or decrease effector function (see for examples, Umana et al., 1999, Nat. Biotechnol 17:176-180; Davies et al., 2001, Biotechnol Bioeng 74:288-294; Shields et al, 2002, J Biol Chem 277:26733-26740; Shinkawa et al., 2003, J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (Glycart Biotechnology AG, Zurich, Switzerland). Accordingly, in one embodiment the Fc regions of the antibodies of the invention comprise altered glycosylation of amino acid residues. In another embodiment, the altered glycosylation of the amino acid residues results in lowered effector function. In another embodiment, the altered glycosylation of the amino acid residues results in increased effector function. In a specific embodiment, the Fc region has reduced fucosylation. In another embodiment, the Fc region is afucosylated (see for examples, U.S. Patent Application Publication No. 2005/0226867). In another embodiment the Fc region is sialylated, such as wherein at least one galactose moiety is connected to a respective terminal sialic acid moiety by a $\alpha 2,6$ linkage (see for example: International Patent Application Publication No. WO2009079382).

The binding members are useful for treating and/or preventing disorders that are mediated by IL-1R1, especially inflammatory disorders such as rheumatoid arthritis, osteoarthritis (OA) asthma and chronic obstructive pulmonary disease (COPD). The binding members are also useful for treating and/or preventing disorders that are mediated by IL-1R1 such as HIV-1, solid tumours, leukaemias, Alzheimers disease and ischaemic disease.

Further aspects of the present invention provide for compositions containing binding members of the invention, and their use in methods of inhibiting and/or neutralizing IL-1R1, including methods of treatment of the human or animal body by therapy.

For example, binding members according to the invention may be used in a method of treatment and/or prevention, or used in a method of diagnosis, of a biological response, disease, disorder, or condition in the human or animal body (e.g. in a human patient), or in vitro.

The method of treatment and/or prevention may comprise administering to said patient a binding member of the invention in an amount sufficient to measurably neutralize IL-1R1. Conditions treatable in accordance with the present invention include any in which IL-1R1 plays a role, such as COPD and asthma.

Binding members of the present invention may be used in methods of diagnosis or treatment in human or animal subjects, especially human. Binding member of the invention may be used in the preparation of a medicament for use in methods of diagnosis or treatment in human or animal subjects, especially human. The invention further provides the use of a binding member of the present invention for diagnosis or treatment in human or animal subjects, especially humans. Treatment comprises disorders characterized by biological effects mediated by IL-1R1, particularly inflammatory disorders such as rheumatoid arthritis, osteoarthritis (OA) asthma and COPD.

Accordingly, the invention provides a method for treating inflammatory disorders, such as rheumatoid arthritis, osteoarthritis, asthma and COPD in a mammal, comprising administering to said mammal a binding member of the invention. In another embodiment the invention provides the use of a binding member of the invention in the manufacture of a medicament for the treatment of inflammatory disorders, such as rheumatoid arthritis, osteoarthritis, asthma and COPD in a mammal. In another embodiment the invention provides the use of a binding member of the invention for the treatment of inflammatory disorders, such as rheumatoid arthritis, osteoarthritis, asthma and COPD in a mammal. In one embodiment the mammal is a human, in another embodiment the mammal is a non-human animal. In one embodiment the binding member is an antibody, VH domain, or VL domain of the invention, in an amount sufficient to neutralize IL-1R1.

Accordingly, the invention provides a method for the inhibition of neutrophil recruitment and chemotaxis into the lung in a mammal, comprising administering to said mammal a binding member of the invention. In another embodiment the invention provides the use of a binding member of the invention in the manufacture of a medicament for the inhibition of neutrophil recruitment and chemotaxis into the lung in a mammal. In another embodiment the invention provides the use of a binding member of the invention for inhibition of neutrophil recruitment and chemotaxis into the lung in a mammal. In one embodiment the mammal is a human, in another embodiment the mammal is a non-human animal. In one embodiment the binding member is an antibody, VH domain, or VL domain of the invention, in an amount sufficient to neutralize IL-1R1.

Accordingly, the invention provides a method for treating a disorder selected from HIV, solid tumours, leukaemias, Alzheimer's disease, type II diabetes, ischaemic disease and atherosclerosis in a mammal, comprising administering to said mammal a binding member of the invention. In another embodiment the invention provides the use of a binding member of the invention in the manufacture of a medicament for the treatment of a disorder selected from HIV, solid tumours, leukaemias, Alzheimer's disease, type II diabetes, ischaemic disease and atherosclerosis in a mammal. In another embodiment the invention provides the use of a binding member of the invention for the treatment of a disorder selected from HIV, solid tumours, leukaemias, Alzheimer's disease, type II diabetes, ischaemic disease and atherosclerosis in a mammal. In one embodiment the mammal is a human, in another embodiment the mammal is a non-human animal. In one embodiment the binding member is an antibody, VH domain, or VL domain of the invention, in an amount sufficient to neutralize IL-1R1.

When test cells are contacted with the binding member of the invention in vitro, a control cell(s) may also be used for positive controls (e.g., reactions containing no binding member) and/or negative controls (e.g., reactions containing no IL-1R1 and/or antigen).

When cells are contacted by the binding member in vivo, for example, by administering the binding member of the invention to a mammal exhibiting IL-1α- and/or IL-1β-mediated biological responses, the binding member of the invention is administered in amounts sufficient to neutralize IL-1R1.

Still further, the invention provides a method for reducing IL-1R1-mediated activity in a mammal, such as a human, comprising administering a binding member, such as an antibody, VH domain, or VL domain of the invention. In another embodiment the invention provides the use of a binding member of the invention in the manufacture of a medicament for reducing IL-1R1-mediated activity in a mammal. In another embodiment the invention provides the use of a binding member of the invention for reducing IL-1R1-mediated activity in a mammal. In one embodiment the mammal is a human, in another embodiment the mammal is a non-human animal. In one embodiment the binding member is an antibody, VH domain, or VL domain of the invention, in an amount sufficient to neutralize IL-1R1 and reduce IL-1R1-mediated activity.

Diseases or disorders for which binding members of the invention may be used include but are not limited to:

1. Respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS), adenovirus, and ARDS and ALI;

2. Bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kawasaki's disease, Kikuchi disease; drug-induced arthalgias, tendonititides, and myopathies;

3. Pain and connective tissue remodelling of musculoskeletal disorders due to injury, for example sports injury, or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis);

4. Skin: psoriasis, parapsoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, mycosis fungoides, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

5. Eyes: blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

6. Gastrointestinal tract: glossitis, gingivitis, periodontitis; oesophagitis, including reflux; eosinophilic gastro-enteritis, mastocytosis, Crohn's disease, colitis e.g. ulcerative colitis, indeterminant colitis, proctitis, microscopic colitis, pruritis ani; Coeliac disease, irritable bowel syndrome, irritable bowel disorder, non-inflammatory diarrhoea and food-related allergies which may have effects remote from the gut (thr example migraine, rhinitis or eczema);

7. Abdominal: hepatitis, including autoimmune, alcoholic and viral; fibrosis and cirrhosis of the liver; cholecystitis; pancreatitis, both acute and chronic;

8. Genitourinary: nephritis including interstitial and glomerulonephritis; nephrotic syndrome; cystitis including acute and chronic (interstitial) cystitis and thinner's ulcer; acute and chronic urethritis, prostatitis, epididymitis, oophoritis and salpingitis; vulvo-vaginitis; Peyronie's disease; erectile dysfunction (both male and female);

9. Allograft rejection: acute and chronic following, for example, transplantation of kidney, heart, liver, lung, bone marrow, skin or cornea or following blood transfusion; or acute and chronic graft versus host disease;

10. CNS: Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; tropical spastic paraparesis, neurosarcoidosis; central and peripheral nervous system complications of malignant, infectious or autoimmune processes;

11. Other auto-immune and allergic disorders (including in combination with other allergy therapies) including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome; pre-term labour 12. Other disorders with an inflammatory or immunological component; including acquired immune deficiency syndrome (AIDS), leprosy, Sezary syndrome, and paraneoplastic syndromes;

13. Cardiovascular: atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins; and 14. Oncology: treatment of common cancers including prostate, breast, lung, ovarian, pancreatic, bowel and colon, stomach, skin and brain tumours and, malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes.

The data presented herein with respect to binding and neutralization of IL-1R1 thus indicate that binding members of the invention can be used to treat or prevent such disorders, including the reduction of severity of the disorders. Accordingly, the invention provides a method of treating or reducing the severity of at least one symptom of any of the disorders mentioned herein, comprising administering to a patient in need thereof an effective amount of one or more binding members of the present invention alone or in a combined therapeutic regimen with another appropriate medicament known in the art or described herein such that the severity of at least one symptom of any of the above disorders is reduced.

Binding members of the invention may be used in appropriate animals and in animal models of disease, especially monkeys.

Thus, the binding members of the present invention are useful as therapeutic agents in the treatment of diseases or disorders involving IL-1R1, e.g. IL-1R1 production, expression and/or activity, especially aberrant production, expression, or activity. A method of treatment may comprise administering an effective amount of a binding member of the invention to a patient in need thereof, wherein production, expression and/or activity of IL-1R1 is thereby decreased. A method of treatment may comprise (i) identifying a patient demonstrating increased IL-1R1 or IL-1 levels or activity thereof, for instance using the diagnostic methods described above, and (ii) administering an effective amount of a binding member of the invention to the patient, wherein increased production, expression and/or activity of IL-1R1 is decreased. An alternative method of treatment may comprise (i) identifying a patient who has no apparent increase in IL-1R1-mediated activity but who is believed to benefit from administration of a binding member of the invention, and (ii) administering an effective amount of a binding member of the invention to the patient. An effective amount according to the invention is an amount that decreases the increased production, expression and/or activity of IL-1R1 so as to decrease or lessen the severity of at least one symptom of the particular disease or disorder being treated, but not necessarily cure the disease or disorder.

The invention also provides a method of antagonizing at least one effect of IL-1R1 comprising contacting with or administering an effective amount of one or more binding members of the present invention such that said at least one effect of IL-1R1 is antagonised. Effects of IL-1R1 that may be antagonised by the methods of the invention include biological responses mediated by IL-1α and/or IL-1β, and any downstream effects that arise as a consequence of these binding reactions.

Accordingly, further aspects of the invention provide the use of an isolated binding member, such as an antibody, VH domain or VL domain of the invention for the manufacture of a medicament for treating a disorder associated with, or mediated by, IL-1R1 as discussed herein. Such use of, or methods of making, a medicament or pharmaceutical composition comprise formulating the binding member with a pharmaceutically acceptable excipient.

A pharmaceutically acceptable excipient may be a compound or a combination of compounds entering into a pharmaceutical composition not provoking secondary reactions and which allows, for example, facilitation of the administration of the active compound(s), an increase in its lifespan and/or in its efficacy in the body, an increase in its solubility in solution or else an improvement in its conservation. These pharmaceutically acceptable excipients are well known and will be adapted by the person skilled in the art as a function of the nature and of the mode of administration of the active compound(s) chosen.

Binding members of the present invention will usually be administered in the form of a pharmaceutical composition, which may comprise at least one component in addition to the binding member. Thus pharmaceutical compositions according to the present invention, and for use in accordance with the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, inhaled, intra-tracheal, topical, intra-vesicular or by injection, as discussed below.

Pharmaceutical compositions for oral administration, such as for example single domain antibody molecules (e.g. "Nanobodies™") etc are also envisaged in the present invention. Such oral formulations may be in tablet, capsule, powder, liquid or semi-solid form. A tablet may comprise a solid carrier, such as gelatin or an adjuvant. Liquid pharmaceutical compositions generally comprise a liquid carrier, such as water, petroleum, animal or vegetable oils, mineral oil or synthetic oil. Physiological saline solution, dextrose or other saccharide solution or glycols, such as ethylene glycol, propylene glycol or polyethylene glycol may be included.

For intra-venous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

Binding members of the present invention may be formulated in liquid, semi-solid or solid forms depending on the physicochemical properties of the molecule and the route of delivery. Formulations may include excipients, or combinations of excipients, for example: sugars, amino acids and surfactants. Liquid formulations may include a wide range of antibody concentrations and pH. Solid formulations may be produced by lyophilisation, spray drying, or drying by supercritical fluid technology, for example. Formulations of anti-IL-1R1 will depend upon the intended route of delivery: for example, formulations for pulmonary delivery may consist of particles with physical properties that ensure penetration into the deep lung upon inhalation; topical formulations (e.g. for treatment of scarring, e.g. dermal scarring) may include viscosity modifying agents, which prolong the time that the drug is resident at the site of action. A binding member may be prepared with a carrier that will protect the binding member against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known to those skilled in the art [65].

Anti-IL-1R1 treatment may be given orally (such as for example single domain antibody molecules (e.g. "Nanobodies™")) by injection (for example, subcutaneously, intra-articular, intra-venously, intra-peritoneal, intra-arterial or intra-muscularly), by inhalation, intra-tracheal, by the intra-vesicular route (instillation into the urinary bladder), or topically (for example intra-ocular, intra-nasal, rectal, into wounds, on skin). The treatment may be administered by pulse infusion, particularly with declining doses of the binding member. The route of administration can be determined by the physicochemical characteristics of the treatment, by special considerations for the disease or by the requirement to optimize efficacy or to minimize side-effects. One particular route of administration is intra-venous. Another route of administering pharmaceutical compositions of the present invention is subcutaneously. It is envisaged that anti-IL-1R1 treatment will not be restricted to use in the clinic. Therefore, subcutaneous injection using a needle-free device is also advantageous.

Examples of intravenous formulations include:
25 mM histidine,
120 mM sodium chloride
pH 6.0.

A binding member for IL-1R1 or composition comprising a binding member for IL-1R1 may be used as part of a combination therapy in conjunction with an additional medicinal component. Combination treatments may be used to provide significant synergistic effects, particularly the combination of an anti-IL-1R1 binding member with one or more other drugs. A binding member for IL-1R1 may be administered concurrently or sequentially or as a combined preparation with another therapeutic agent or agents, for the treatment of one or more of the conditions listed herein.

A binding member of the invention may be formulated and/or used in combination with other available treatments for Il-1R1 mediated diseases such as obstructive diseases of the airways, asthma and allergic disorders, or other disorders involving IL-1R1 mediated effects.

A binding member according to the present invention may be provided as sole therapy or in combination or addition with one or more of the following agents:

a cytokine or agonist or antagonist of cytokine function (e.g. an agent which acts on cytokine signalling pathways, such as a modulator of the SOCS system), such as an alpha-, beta- and/or gamma-interferon; insulin-like growth factor type I (IGF-1), its receptors and associated binding proteins; interleukins (IL), e.g. one or more of IL-2 to -33, and/or an interleukin antagonist or inhibitor, such as anakinra; inhibitors of receptors of interleukin family members or inhibitors of specific subunits of such receptors, a tumour necrosis factor alpha (TNF-α) inhibitor, such as an anti-TNF monoclonal antibodies (for example infliximab, adalimumab and/or CDP-870) and/or a TNF receptor antagonist, e.g. an immunoglobulin molecule (such as etanercept) and/or a low-molecular-weight agent, such as pentoxyfylline;

a modulator of B cells, e.g. a monoclonal antibody targeting B-lymphocytes (such as CD20 (rituximab) or MRA-aIL16R) or T-lymphocytes (e.g. CTLA4-Ig, HuMax Il-15 or Abatacept);

a modulator that inhibits osteoclast activity, for example an antibody to RANKL;

a modulator of chemokine or chemokine receptor function, such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 and CXCR6 (for the C—X—C family) and $CX_3CR1$ for the $C—X_3—C$ family;

an inhibitor of matrix metalloproteases (MMPs), i.e. one or more of the stromelysins, the collagenases and the gelatinases as well as aggrecanase, especially collagenase-1 (MMP-1), collagenase-2 (MMP-8), collagenase-3 (MMP-13), stromelysin-1 (MMP-3), stromelysin-2 (MMP-10) and/or stromelysin-3 (MMP-11) and/or MMP-9 and/or MMP-12, e.g. an agent such as doxycycline;

a leukotriene biosynthesis inhibitor, 5-lipoxygenase (5-LO) inhibitor or 5-lipoxygenase activating protein (FLAP) antagonist, such as zileuton; ABT-761; fenleuton; tepoxalin; Abbott-79175; Abbott-85761; N-(5-substituted)-thiophene-2-alkylsulfonamides; 2,6-di-tert-butylphenolhydrazones; methoxytetrahydropyrans such as Zeneca ZD-2138; the compound SB-210661; a pyridinyl-substituted 2-cyanonaphthalene compound, such as L-739,010; a 2-cyanoquinoline compound, such as L-746,530; indole and/or a quinoline compound, such as MK-591, MK-886 and/or BAY×1005;

a receptor antagonist for leukotrienes (LT) B4, LTC4, LTD4, and LTE4, selected from the group consisting of the phenothiazin-3-1s, such as L-651,392; amidino compounds, such as CGS-25019c; benzoxalamines, such as ontazolast; benzenecarboximidamides, such as BIIL 284/260; and compounds, such as zafirlukast, ablukast, montelukast, pranlukast, verlukast (MK-679), RG-12525, Ro-245913, iralukast (CGP 45715A) and BAY×7195;

a phosphodiesterase (PDE) inhibitor, such as a methylxanthanine, e.g. theophylline and/or aminophylline; and/or a selective PDE isoenzyme inhibitor, e.g. a PDE4 inhibitor and/or inhibitor of the isoform PDE4D and/or an inhibitor of PDE5;

a histamine type 1 receptor antagonist, such as cetirizine, loratadine, desloratadine, fexofenadine, acrivastine, terfenadine, astemizole, azelastine, levocabastine, chlorpheniramine, promethazine, cyclizine, and/or mizolastine (generally applied orally, topically or parenterally);

a proton pump inhibitor (such as omeprazole) or gastroprotective histamine type 2 receptor antagonist;

an antagonist of the histamine type 4 receptor;

an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride and ethylnorepinephrine hydrochloride;

an anticholinergic agent, e.g. a muscarinic receptor (M1, M2, and M3) antagonist, such as atropine, hyoscine, glycopyrrolate, ipratropium bromide, tiotropiumrn bromide, oxitropium bromide, pirenzepine and telenzepine;

a beta-adrenoceptor agonist (including beta receptor subtypes 1-4), such as isoprenaline, salbutamol, formoterol, salmeterol, terbutaline, orciprenaline, bitolterol mesylate and/or pirbuterol, e.g. a chiral enantiomer thereof;

a chromone, e.g. sodium chromoglycate and/or nedocromil sodium;

a glucocorticoid, such as flunisolide, triamcinolone acetonide, beclomethasone dipropionate, budesonide, fluticasone propionate, ciclesonide, and/or mometasone furoate;

an agent that modulate nuclear hormone receptors, such as a PPAR;

an immunoglobulin (Ig) or Ig preparation or an antagonist or antibody modulating Ig function, such as anti-IL-1R1 that binds to the same or a different epitope as the binding member of the invention;

other systemic or topically-applied anti-inflammatory agent, e.g. thalidomide or a derivative thereof, a retinoid, dithranol and/or calcipotriol;

combinations of aminosalicylates and sulfapyridine, such as sulfasalazine, mesalazine, balsalazide, and olsalazine; and immunomodulatory agents, such as the thiopurines; and corticosteroids, such as budesonide;

an antibacterial agent, e.g. a penicillin derivative, a tetracycline, a macrolide, a beta-lactam, a fluoroquinolone, metronidazole and/or an inhaled aminoglycoside; and/or an antiviral agent, e.g. acyclovir, famciclovir, valaciclovir, ganciclovir, cidofovir; amantadine, rimantadine; ribavirin; zanamavir and/or oseltamavir; a protease inhibitor, such as indinavir, nelfinavir, ritonavir and/or saquinavir; a nucleoside reverse transcriptase inhibitor, such as didanosine, lamivudine, stavudine, zalcitabine, zidovudine; a non-nucleoside reverse transcriptase inhibitor, such as nevirapine, efavirenz;

a cardiovascular agent, such as

1) Anti dyslipidaemia agents such as, HMG-CoA reductase inhibitors (eg statins); PPARa agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);

2) Antihypertensive agents such as, β blockers (eg atenolol, inderal); ACE inhibitors (eg lisinopril); Calcium antagonists (eg. nifedipine); Angiotensin receptor antagonists (eg candesartan), a antagonists and diuretic agents (eg. furosemide, benzthiazide);

3) Haemostasis modulators such as, antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and Low molecular weight analogues, hirudin) and warfarin;

4) Agents which antagonise the actions of glucagon; and

5) Anti-inflammatory agents, such as non steroidal anti inflammatory drugs (eg. aspirin) and steroidal anti-inflammatory agents (eg. cortisone).

6) modulators of blood cell morphology, such as pentoxyfylline.

an anti-diabetic agent such as:
1) Insulin and insulin analogues;
2) insulin secretagogues including sulphonylureas (for example glibenclamide, glipizide), prandial glucose regulators (for example repaglinide, nateglinide);
3) Agents that improve incretin action (for example dipeptidyl peptidase IV inhibitors for example Saxagliptin, Sitagliptin, Vildagliptin or Alogliptin, and GLP-1 agonists);
4) insulin sensitising agents including PPARgamma agonists (for example pioglitazone and rosiglitazone), and agents with combined PPARalpha and gamma activity;
5) Agents that modulate hepatic glucose balance (for example metformin, fructose 1, 6 bisphosphatase inhibitors, glycogen phopsphorylase inhibitors, glycogen synthase kinase inhibitors);
6) Agents designed to reduce the absorption of glucose from the intestine (for example acarbose);
7) Agents that prevent the reabsorption of glucose by the kidney (SGLT inhibitors);
8) Agents designed to treat the complications of prolonged hyperglycaemia (for example aldose reductase inhibitors);

an anti-obesity agent such as a noradrenaline/serotonin non-selective reuptake inhibitor.

a CNS agent, such as an antidepressant (such as sertraline), anti-Parkinsonian drug (such as deprenyl, L-dopa, ropinirole, pramipexole; MAOB inhibitor, such as selegine and rasagiline; comP inhibitor, such as tasmar; A-2 inhibitor, dopamine reuptake inhibitor, NMDA antagonist, nicotine agonist, dopamine agonist and/or inhibitor of neuronal nitric oxide synthase) and an anti-Alzheimer's drug, such as donepezil, rivastigmine, tacrine, COX-2 inhibitor, propentofylline or metrifonate;

an agent for the treatment of acute and chronic pain, e.g. a centrally or peripherally-acting analgesic, such as an opioid analogue or derivative, carbamazepine, phenyloin, sodium valproate, amitryptiline or other antidepressant agent, paracetamol, or non-steroidal anti-inflammatory agent;

a parenterally or topically-applied (including inhaled) local anaesthetic agent, such as lignocaine or an analogue thereof;

an anti-osteoporosis agent, e.g. a hormonal agent, such as raloxifene, or a biphosphonate, such as alendronate;

(i) a tryptase inhibitor; (ii) a platelet activating factor (PAF) antagonist; (iii) an interleukin converting enzyme (ICE) inhibitor; (iv) an IMPDH inhibitor; (v) an adhesion molecule inhibitors including VLA-4 antagonist; (vi) a cathepsin; (vii) a kinase inhibitor, e.g. an inhibitor of tyrosine kinases (such as Btk, Itk, Jak3 MAP examples of inhibitors might include (Gefitinib, Imatinib mesylate), a serine/threonine kinase (e.g. an inhibitor of MAP kinase, such as p38, JNK, protein kinases A, B and C and IKK), or a kinase involved in cell cycle regulation (e.g. a cylin dependent kinase); (viii) a glucose-6 phosphate dehydrogenase inhibitor; (ix) a kinin-B$_1$- and/or B$_2$-receptor antagonist; (x) an anti-gout agent, e.g. colchicine; (xi) a xanthine oxidase inhibitor, e.g. allopurinol; (xii) a uricosuric agent, e.g. probenecid, sulfinpyrazone, and/or benzbromarone; (xiii) a growth hormone secretagogue; (xiv) transforming growth factor (TGFβ); (xv) platelet-derived growth factor (PDGF); (xvi) fibroblast growth factor, e.g. basic fibroblast growth factor (bFGF); (xvii) granulocyte macrophage colony stimulating factor (GM-CSF); (xviii) capsaicin cream; (xix) a tachykinin NK$_1$. and/or NK$_3$. receptor antagonist, such as NKP-608C, SB-233412 (talnetant) and/or D-4418; (xx) an elastase inhibitor, e.g. UT-77 and/or ZD-0892; (xxi) a TNF-alpha converting enzyme inhibitor (TACE); (xxii) induced nitric oxide synthase (iNOS) inhibitor or (xxiii) a chemoattractant receptor-homologous molecule expressed on TH2 cells (such as a CRTH2 antagonist); (xxiv) an inhibitor of a P38 (xxv) agent modulating the function of Toll-like receptors (TLR) and (xxvi) an agent modulating the activity of purinergic receptors, such as P2x7; (xxvii) an inhibitor of transcription factor activation, such as NFkB, API, and/or STATS.

A binding member according to the present invention may also be provided as sole therapy or in combination or addition with conventional surgery or radiotherapy or cancer chemotherapy. Such cancer chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-2-hydroxyethyl)piperazin-1-yl]-2-methylpyrimidin-4-ylamino}thiazole-5-carboxamide (dasatinib, BMS-354825; *J. Med. Chem.* 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMIN107); inhibitors of serine/threonine kinases (for example Ras/Raf signalling inhibitors such as farnesyl transferase inhibitors, for example sorafenib (BAY 43-9006), tipifamib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in international Patent Applications WO097/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in international Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumour cell lines and approaches using anti-idiotypic antibodies.

An inhibitor may be specific or may be a mixed inhibitor, e.g. an inhibitor targeting more than one of the molecules (e.g. receptors) or molecular classes mentioned above.

The binding member could also be used in association with a chemotherapeutic agent such as a tyrosine kinase inhibitor in co-administration or in the form of an immunoconjugate. Fragments of said antibody could also be use in bispecific antibodies obtained by recombinant mechanisms or biochemical coupling and then associating the specificity of the above described antibody with the specificity of other antibodies able to recognize other molecules involved in the activity for which IL-1R1 is associated.

For treatment of an inflammatory disease, e.g. rheumatoid arthritis, osteoarthritis, asthma, allergic rhinitis, chronic obstructive pulmonary disease (COPD), or psoriasis, a binding member of the invention may be combined with one or more agents, such as non-steroidal anti-inflammatory agents (hereinafter NSAIDs) including non-selective cyclo-oxygenase (COX)-1/COX-2 inhibitors whether applied topically or systemically, such as piroxicam, diclofenac, propionic acids, such as naproxen, flurbiprofen, fenoprofen, ketoprofen and ibuprofen, fenamates, such as mefenamic acid, indomethacin, sulindac, azapropazone, pyrazolones, such as phenylbutazone, salicylates, such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intra-muscular, intra-venous or intra-articular routes); methotrexate, leflunomide; hydroxychloroquine, d-penicillamine, auranofin or other parenteral or oral gold preparations; analgesics; diacerein; intra-articular therapies, such as hyaluronic acid derivatives; and nutritional supplements, such as glucosamine.

A binding member of the invention and one or more of the above additional medicinal components may be used in the manufacture of a medicament. The medicament may be for separate or combined administration to an individual, and accordingly may comprise the binding member and the additional component as a combined preparation or as separate preparations. Separate preparations may be used to facilitate separate and sequential or simultaneous administration, and allow administration of the components by different routes e.g. oral and parenteral administration.

In accordance with the present invention, compositions provided may be administered to mammals. Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the type of binding member, the method of administration, the scheduling of administration and other factors known to medical practitioners. Prescription of treatment, e.g. decisions on dosage etc, is within the responsibility of general practitioners and other medical doctors and may depend on the severity of the symptoms and/or progression of a disease being treated. Appropriate doses of antibody are well known in the art [66, 67]. Specific dosages indicated herein or in the Physician's Desk Reference (2003) as appropriate for the type of medicament being administered may be used. A therapeutically effective amount or suitable dose of a binding member of the invention can be determined by comparing its in vitro activity and in vivo activity in an animal model. Methods for extrapolation of effective dosages in mice and other test animals to humans are known. The precise dose will depend upon a number of factors, including whether the antibody is for diagnosis, prevention or for treatment, the size and location of the area to be treated, the precise nature of the antibody (e.g. whole antibody, fragment or diabody) and the nature of any detectable label or other molecule attached to the antibody. A typical antibody dose will be in the range 100 µg to 1 g for systemic applications, and 1 µg to 1 mg for topical applications. An initial higher loading dose, followed by one or more lower doses, may be administered.

Typically, the antibody will be a whole antibody, e.g. the IgG1 isotype, IgG2 isotype, IgG3 isotype or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. Treatments may be every two to four weeks for subcutaneous administration and every four to eight weeks for intra-venous administration. Treatment may be periodic, and the period between administrations is about two weeks or more, e.g. about three weeks or more, about four weeks or more, or about once a month. Treatment may be given before, and/or after surgery, and/or may be administered or applied directly at the anatomical site of surgical treatment.

The binding members of the invention also have diagnostic utility, such as for detecting the presence or amount of IL-1R1, such as in a sample patient with an obstructive disease of the airways or other inflammatory disorder involving IL-1R. Such diagnostic utility may involve labelling a binding member of the invention.

Binding members of the invention may be labelled with a detectable or functional label. Thus, a binding member or antibody molecule can be present in the form of an immunoconjugate so as to obtain a detectable and/or quantifiable signal. An immunoconjugate may comprise an antibody molecule of the invention conjugated with detectable or functional label. A label can be any molecule that produces or can be induced to produce a signal, including but not limited to fluorescers, radiolabels, enzymes, chemiluminescers or photosensitizers. Thus, binding may be detected and/or measured by detecting fluorescence or luminescence, radioactivity, enzyme activity or light absorbance.

Suitable labels include, by way of illustration and not limitation, enzymes, such as alkaline phosphatase, glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase e.g. horseradish peroxidase;

dyes;

fluorescent labels or fluorescers, such as fluorescein and its derivatives, fluorochrome, rhodamine compounds and derivatives, GFP (GFP for "Green Fluorescent Protein"), dansyl, umbelliferone, phycoerythrin, phycocyanin, allophycocyanin, o-phthaldehyde, and fluorescamine; fluorophores such as lanthanide cryptates and chelates e.g. Europium etc (Perkin Elmer and Cis Biointernational), chemoluminescent labels or chemiluminescers, such as isoluminol, luminol and the dioxetanes;

bio-luminescent labels, such as luciferase and luciferin;

sensitizers;

coenzymes;

enzyme substrates;

radiolabels including but not limited to bromine77, carbon14, cobalt57, fluorine8, gallium67, gallium 68, hydrogen3 (tritium), indium111, indium113m, iodine123m, iodine125, iodine126, iodine131, iodine133, mercury107, mercury203, phosphorous32, rhenium99m, rhenium101, rhenium105, ruthenium95, ruthenium97, ruthenium 103, ruthenium105, scandium47, selenium75, sulphur35, technetium99, technetium99m, tellurium121m, tellurium122m, tellurium125m, thulium165, thulium167, thulium168, yttrium199 and other radiolabels mentioned herein;

particles, such as latex or carbon particles; metal sol; crystallite; liposomes; cells, etc., which may be further labelled with a dye, catalyst or other detectable group;

molecules such as biotin, digoxygenin or 5-bromodeoxyuridine;

toxin moieties, such as for example a toxin moiety selected from a group of *Pseudomonas* exotoxin (PE or a cytotoxic fragment or mutant thereof), Diptheria toxin or a cytotoxic fragment or mutant thereof a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

Suitable enzymes and coenzymes are disclosed in Litman, et al., U.S. Pat. No. 4,275,149, and Bogusiaski, et al., U.S. Pat. No. 4,318,980, each of which are herein incorporated by reference in their entireties. Suitable fluorescers and chemiluminescers are disclosed in Litman, et al., U.S. Pat. No. 4,275,149, which is incorporated herein by reference in its entirety. Labels further include chemical moieties, such as biotin that may be detected via binding to a specific cognate detectable moiety, e.g. labelled avidin or streptavidin. Detectable labels may be attached to antibodies of the invention using conventional chemistry known in the art.

Immunoconjugates or their functional fragments can be prepared by methods known to the person skilled in the art. They can be coupled to enzymes or to fluorescent labels directly or by the intermediary of a spacer group or of a linking group, such as a polyaldehyde, like glutaraldehyde, ethylenediaminetetraacetic acid (EDTA), diethylene-triaminepentaacetic acid (DPTA), or in the presence of coupling agents, such as those mentioned above for the therapeutic conjugates. Conjugates containing labels of fluorescein type can be prepared by reaction with an isothiocyanate.

The methods known to the person skilled in the art existing for coupling the therapeutic radioisotopes to the antibodies either directly or via a chelating agent, such as EDTA, DTPA mentioned above can be used for the radioelements which can be used in diagnosis. It is likewise possible to perform labelling with sodium 25 by the chloramine T method [68] or else with technetium99m by the technique of Crockford et al., (U.S. Pat. No. 4,424,200, herein incorporated by reference in its entirety) or attached via DTPA as described by Hnatowich (U.S. Pat. No. 4,479,930, herein incorporated by reference in its entirety).

There are numerous methods by which the label can produce a signal detectable by external means, for example, by visual examination, electromagnetic radiation, heat, and chemical reagents. The label can also be bound to another binding member that binds the antibody of the invention, or to a support.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. This second wavelength emission may also transfer energy to a labelled acceptor molecule, and the resultant energy dissipated from the acceptor molecule by emission of light for example fluorescence resonance energy transfer (FRET). Other labels that directly produce a signal include radioactive isotopes and dyes.

Alternately, the label may need other components to produce a signal, and the signal producing system would then include all the components required to produce a measurable signal, which may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al. U.S. Pat. No. 5,185,243, which is herein incorporated herein by reference in its entirety.

The present invention provides a method comprising causing or allowing binding of a binding member as provided herein to IL-1R1. As noted, such binding may take place in vivo, e.g. following administration of a binding member or encoding nucleic acid to a human or animal (e.g., a mammal), or it may take place in vitro, for example in ELISA, Western blotting, immunocytochemistry, immunoprecipitation, affinity chromatography, and biochemical or cell-based assays.

Generally, complexes between the binding member of the invention and IL-1R1 may be detected by, inter alia, enzyme-linked immunoassay, radioassay, immunoprecipitation, fluorescence immunoassay, chemiluminescent assay, immunoblot assay, lateral flow assay, agglutination assay and particulate-based assay.

The present invention also provides for measuring levels of antigen directly, by employing a binding member according to the invention for example in a biosensor system. For instance, the present invention comprises a method of detecting and/or measuring binding to IL-1R1, comprising, (i) exposing said binding member to IL-1R1 and (ii) detecting binding of said binding member to IL-1R1, wherein binding is detected using any method or detectable label described herein. This, and any other binding detection method described herein, may be interpreted directly by the person performing the method, for instance, by visually observing a detectable label. Alternatively, this method, or any other binding detection method described herein, may produce a report in the form of an autoradiograph, a photograph, a computer printout, a flow cytometry report, a graph, a chart, a test tube or container or well containing the result, or any other visual or physical representation of a result of the method.

The amount of binding of binding member to IL-1R1 may be determined. Quantitation may be related to the amount of the antigen in a test sample, which may be of diagnostic interest. Screening for IL-1R1 binding and/or the quantitation thereof may be useful, for instance, in screening patients for diseases or disorders referred to herein and/or any other disease or disorder involving aberrant IL-1R1 production, expression and/or activity.

A diagnostic method of the invention may comprise (i) obtaining a tissue or fluid sample from a subject, (ii) exposing said tissue or fluid sample to one or more binding members of the present invention; and (iii) detecting bound IL-1R1 as compared with a control sample, wherein an increase in the amount of IL-1R1 binding as compared with the control may indicate an aberrant level of IL-1R1 production, expression or activity. Tissue or fluid samples to be tested include blood, serum, urine, biopsy material, tumours, or any tissue suspected of containing aberrant IL-1R1 levels. Subjects testing positive for aberrant IL-1R1 levels or activity may also benefit from the treatment methods disclosed later herein.

The diagnostic method of the invention may further comprise capturing a complex of the binding member and IL-1R1 via an immobilized antigen. For example, an antigen may be immobilized on a lateral strip assay for capturing antigen-specific IL-1R1 in a sample of interest.

Those skilled in the art are able to choose a suitable mode of determining binding of the binding member to an antigen according to their preference and general knowledge, in light of the methods disclosed herein.

The reactivities of binding members in a sample may be determined by any appropriate means. Radioimmunoassay (RIA) is one possibility. Radioactive labelled antigen is mixed with unlabelled antigen (the test sample) and allowed to bind to the binding member. Bound antigen is physically separated from unbound antigen and the amount of radioactive antigen bound to the binding member determined. The more antigen there is in the test sample the less radioactive antigen will bind to the binding member. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red, and lanthanide chelates or cryptates. Suitable chromogenic dyes include diamininobenzidine.

Other reporters include macromolecular colloidal particles or particulate material, such as latex beads that are colored, magnetic or paramagnetic, and biologically or chemically active agents that can directly or indirectly cause detectable signals to be visually observed, electronically detected or otherwise recorded. These molecules may be enzymes, which catalyze reactions that develop, or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual binding member-reporter conjugates may be used to derive quantifiable absolute or relative data of the relevant binding member binding in samples (normal and test).

A kit comprising a binding member according to any aspect or embodiment of the present invention is also provided as an aspect of the present invention. In the kit, the binding member may be labelled to allow its reactivity in a sample to be determined, e.g. as described further below. Further the binding member may or may not be attached to a solid support. Components of a kit are generally sterile and in sealed vials or other containers. Kits may be employed in diagnostic analysis or other methods for which binding members are useful. A kit may contain instructions for use of the components in a method, e.g. a method in accordance with the present invention. Ancillary materials to assist in or to enable performing such a method may be included within a kit of the invention. The ancillary materials include a second, different binding member which binds to the first binding member and is conjugated to a detectable label (e.g., a fluorescent label, radioactive isotope or enzyme). Antibody-based kits may also comprise beads for conducting an immunoprecipitation. Each component of the kits is generally in its own suitable container. Thus, these kits generally comprise distinct containers suitable for each binding member. Further, the kits may comprise instructions for performing the assay and methods for interpreting and analyzing the data resulting from the performance of the assay.

The present invention also provides the use of a binding member as above for measuring antigen levels in a competition assay, that is to say a method of measuring the level of antigen in a sample by employing a binding member as provided by the present invention in a competition assay. This may be where the physical separation of bound from unbound antigen is not required. Linking a reporter molecule to the binding member so that a physical or optical change occurs on binding is one possibility. The reporter molecule may directly or indirectly generate detectable signals, which may be quantifiable. The linkage of reporter molecules may be directly or indirectly, covalently, e.g. via a peptide bond or non-covalently. Linkage via a peptide bond may be as a result of recombinant expression of a gene fusion encoding antibody and reporter molecule.

In one embodiment the present invention includes a method of identifying an IL-1R1 binding compound, comprising (i) immobilizing IL-1R1 to a support, (ii) contacting said immobilized IL-1R1 simultaneously or in a step-wise manner with at least one tagged or labelled binding member according to the invention and one or more untagged or unlabelled test binding compounds, and (iii) identifying a new IL-1R1 binding compound by observing a decrease in the amount of bound tag from the tagged binding member. Such methods can be performed in a high-throughput manner using a multiwell or array format. Such assays may be also be performed in solution. See, for instance, U.S. Pat. No. 5,814,468, which is herein incorporated by reference in its entirety. As described above, detection of binding may be interpreted directly by the person performing the method, for instance, by visually observing a detectable label, or a decrease in the presence thereof. Alternatively, the binding methods of the invention may produce a report in the form of an autoradiograph, a photograph, a computer printout, a flow cytometry report, a graph, a chart, a test tube or container or well containing the result, or any other visual or physical representation of a result of the method.

The present invention further provides an isolated nucleic acid encoding a binding member of the present invention. Nucleic acid may include DNA and/or RNA. In one embodiment, the present invention provides a nucleic acid that codes for a CDR or set of CDRs or VH domain or VL domain or antibody antigen-binding site or antibody molecule, e.g. scFv or IgG1, of the invention.

In further aspects, the invention provides an isolated nucleic acid which comprises a sequence encoding a binding member of the invention, VH domain and/or VL domain according to the present invention. For example, SEQ ID NOS: 92, 2, 122, 102, 12, 62, 22, 32, 72, 42, 112, 52, and 82 encode exemplary VH domains of the present invention, and SEQ ID NOS: 97, 7, 127, 107, 17, 67, 27, 37, 77, 47, 117, 57, and 87 encode exemplary VL domains of the present invention.

The present invention also provides constructs in the form of plasmids, vectors, transcription or expression cassettes which comprise at least one nucleic acid as above.

The present invention also provides a recombinant host cell that comprises one or more constructs as above and provides a method of production of the encoded product, which method comprises expression from said encoding construct. Expression may conveniently be achieved by culturing under appropriate conditions recombinant host cells containing the construct. Following production by expression a VH or VL domain, or binding member may be isolated and/or purified using any suitable technique, then used as appropriate.

Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

A yet further aspect provides a method of production of an antibody or VH variable domain, the method including causing expression from encoding nucleic acid. Such a method may comprise culturing host cells under conditions for production of said antibody VH variable domain.

Analogous methods for production of VL variable domains and binding members, such as antibodies, comprising a VH and/or VL domain are provided as further aspects of the present invention.

A method of production may comprise a step of isolation and/or purification of the product. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals. The expression of antibodies and antibody fragments in prokaryotic cells is well established in the art. For a review, see for example Plückthun [69]. A common bacterial host is *E. coli*.

Expression in eukaryotic cells in culture is also available to those skilled in the art as an option for production of a binding member [70, 71, 72]. Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral e.g. 'phage, as appropriate [73]. Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. [74].

A further aspect of the present invention provides a host cell containing nucleic acid as disclosed herein. Such a host cell may be in vitro and may be in culture. Such a host cell may be in vivo. In vivo presence of the host cell may allow intra-cellular expression of the binding members of the present invention as "intrabodies" or intra-cellular antibodies. Intrabodies may be used for gene therapy.

The invention also includes methods of preparing a binding member, a VH domain and/or a VL domain of the invention, which comprise expressing said nucleic acid under conditions to bring about production of said binding member, VH domain and/or VL domain, and recovering it by isolating or purifying the binding member.

A still further aspect provides a method comprising introducing nucleic acid of the invention into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene. The purification of the expressed product may be achieved by methods known to one of skill in the art.

Nucleic acid of the invention may be integrated into the genome (e.g. chromosome) of the host cell. Integration may be promoted by inclusion of sequences that promote recombination with the genome, in accordance with standard techniques.

The present invention also provides a method that comprises using a construct as stated above in an expression system in order to express a binding member or polypeptide as above.

In general, for the preparation of monoclonal antibodies or their functional fragments, especially of murine origin, it is possible to refer to techniques which are described in particular in the manual "Antibodies" [75] or to the technique of preparation from hybridomas described by Köhler and Milstein [76].

Monoclonal antibodies can be obtained, for example, from a cell obtained from an animal immunized against IL-1R1, or one of its fragments containing the epitope recognized by said monoclonal antibodies. Suitable fragments and peptides or polypeptides comprising them may be used to immunize animals to generate antibodies against IL-1R1. Said IL-1R1, or one of its fragments, can especially be produced according to the usual working methods, by genetic recombination starting with a nucleic acid sequence contained in the cDNA sequence coding for IL-1R1 or fragment thereof, by peptide synthesis starting from a sequence of amino acids comprised in the peptide sequence of the IL-1R1 and/or fragment thereof.

The monoclonal antibodies can, for example, be purified on an affinity column on which IL-1R1 or one of its fragments containing the epitope recognized by said monoclonal antibodies, has previously been immobilized. More particularly, the monoclonal antibodies can be purified by chromatography on protein A and/or G, followed or not followed by ion-exchange chromatography aimed at eliminating the residual protein contaminants as well as the DNA and the lipopolysaccharide (LPS), in itself, followed or not followed by exclusion chromatography on Sepharose™ gel in order to eliminate the potential aggregates due to the presence of dimers or of other multimers. In one embodiment, the whole of these techniques can be used simultaneously or successively.

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

Further techniques available in the art of antibody engineering have made it possible to isolate human and humanized antibodies. For example, human hybridomas can be made as described by Kontermann & Dubel [77]. Phage display, another established technique for generating binding members has been described in detail in many publications, such as Kontermann & Dubel [77] and WO92/01047 (discussed further below), and U.S. Pat. No. 5,969,108, U.S. Pat. No. 5,565,332, U.S. Pat. No. 5,733,743, U.S. Pat. No. 5,858,657, U.S. Pat. No. 5,871,907, U.S. Pat. No. 5,872,215, U.S. Pat. No. 5,885,793, U.S. Pat. No. 5,962,255, U.S. Pat. No. 6,140,471, U.S. Pat. No. 6,172,197, U.S. Pat. No. 6,225,447, U.S. Pat. No. 6,291,650, U.S. Pat. No. 6,492,160 and U.S. Pat. No. 6,521,404.

Transgenic mice in which the mouse antibody genes are inactivated and functionally replaced with human antibody genes while leaving intact other components of the mouse immune system, can be used for isolating human antibodies [78]. Humanized antibodies can be produced using techniques known in the art such as those disclosed in for example WO91/09967, U.S. Pat. No. 5,585,089, EP592106, U.S. Pat. No. 5,565,332 and WO93/17105. Further, WO2004/006955 describes methods for humanizing antibodies, based on selecting variable region framework sequences from human antibody genes by comparing canonical CDR structure types for CDR sequences of the variable region of a non-human antibody to canonical CDR structure types for corresponding CDRs from a library of human antibody sequences, e.g. germline antibody gene segments. Human antibody variable regions having similar canonical CDR structure types to the non-human CDRs form a subset of member human antibody sequences from which to select human framework sequences. The subset members may be further ranked by amino acid similarity between the human and the non-human CDR sequences. In the method of WO2004/006955, top ranking human sequences are selected to provide the framework sequences for constructing a chimeric antibody that functionally replaces human CDR sequences with the non-human CDR counterparts using the selected subset member human frameworks, thereby providing a humanized antibody of high affinity and low immunogenicity without need for comparing framework sequences between the non-human and human antibodies. Chimeric antibodies made according to the method are also disclosed.

Synthetic antibody molecules may be created by expression from genes generated by means of oligonucleotides synthesized and assembled within suitable expression vectors, for example as described by Knappik et al. [79] or Krebs et al. [80].

As noted above, a binding member in accordance with the present invention modulates and may neutralize a biological activity of IL-1R1. As described herein, IL-R1-binding members of the present invention may be optimised for neutralizing potency. Generally, potency optimisation involves mutating the sequence of a selected binding member (normally the variable domain sequence of an antibody) to generate a library of binding members, which are then assayed for potency and the more potent binding members are selected. Thus selected "potency-optimised" binding members tend to have a higher potency than the binding member from which the library was generated. Nevertheless, high potency binding members may also be obtained without optimisation, for example a high potency binding member may be obtained directly from an initial screen e.g. a biochemical neutralization assay. A "potency optimized" binding member refers to a binding member with an optimized potency of neutralization of a particular activity or downstream function. Assays and potencies are described in more detail elsewhere herein. The present invention provides both potency-optimized and non-optimized binding members, as well as methods for potency optimization from a selected binding member. The present invention thus allows the skilled person to generate binding members having high potency.

Although potency optimization may be used to generate higher potency binding members from a given binding member, it is also noted that high potency binding members may be obtained even without potency optimization.

In a further aspect, the present invention provides a method of obtaining one or more binding members able to bind the antigen, the method including bringing into contact a library of binding members according to the invention and said antigen, and selecting one or more binding members of the library able to bind said antigen.

The library may be displayed on particles or molecular complexes, e.g. replicable genetic packages, such as yeast, bacterial or bacteriophage (e.g. T7) particles, viruses, cells or covalent, ribosomal or other in vitro display systems, each particle or molecular complex containing nucleic acid encoding the antibody VH variable domain displayed on it, and optionally also a displayed VL domain if present. Phage display is described in WO 92/01047 and e.g. U.S. Pat. No. 5,969,108, U.S. Pat. No. 5,565,332, U.S. Pat. No. 5,733,743, U.S. Pat. No. 5,858,657, U.S. Pat. No. 5,871,907, U.S. Pat. No. 5,872,215, U.S. Pat. No. 5,885,793, U.S. Pat. No. 5,962,255, U.S. Pat. No. 6,140,471, U.S. Pat. No. 6,172,197, U.S. Pat. No. 6,225,447, U.S. Pat. No. 6,291,650, U.S. Pat. No. 6,492,160 and U.S. Pat. No. 6,521,404, each of which is herein incorporated by reference in their entirety.

Following selection of binding members able to bind the antigen and displayed on bacteriophage or other library particles or molecular complexes, nucleic acid may be taken from a bacteriophage or other particle or molecular complex displaying a selected binding member. Such nucleic acid may be used in subsequent production of a binding member or an antibody VH or VL variable domain by expression from nucleic acid with the sequence of nucleic acid taken from a bacteriophage or other particle or molecular complex displaying a said selected binding member.

An antibody VH variable domain with the amino acid sequence of an antibody VH variable domain of a said selected binding member may be provided in isolated form, as may a binding member comprising such a VH domain.

Ability to bind IL-1R1 may be further tested, also ability to compete with e.g. a parent antibody molecule (antibody 1 or 4) or an antibody molecule 2, 3, 5 to 10 (e.g. in scFv format and/or IgG format, e.g. IgG1) for binding to IL-1R1. Ability to neutralize IL-1R1 may be tested, as discussed further elsewhere herein.

A binding member according to the present invention may bind with the affinity of the parent (antibody 1 or 4) or other antibody molecule, e.g. scFv, or one of antibodies 2, 3, 5 to 10, e.g. IgG1, or with an affinity that is better.

A binding member according to the present invention may neutralize a biological activity of IL-1R1 with the potency of the parent (antibody 1 or 4) or other antibody molecule, one of antibodies 2, 3, 5 to 10 e.g. scFv, or IgG1, or with a potency that is better.

Binding affinity and neutralization potency of different binding members can be compared under appropriate conditions.

Variants of the VH and VL domains and CDRs of the present invention, including those for which amino acid sequences are set out herein, and which can be employed in binding members for IL-1R1 can be obtained by means of methods of sequence alteration or mutation and screening for antigen binding members with desired characteristics. Examples of desired characteristics include but are not limited to:
Increased binding affinity for antigen relative to known antibodies which are specific for the antigen
Increased neutralization of an antigen activity relative to known antibodies which are specific for the antigen if the activity is known Specified competitive ability with a known antibody or ligand to the antigen at a specific molar ratio
Ability to immunoprecipitate complex
Ability to bind to a specified epitope
Linear epitope, e.g. peptide sequence identified using peptide-binding scan as described herein, e.g. using peptides screened in linear and/or constrained conformation
Conformational epitope, formed by non-continuous residues
Ability to modulate a new biological activity of IL-1R1, or downstream molecule.
Such methods are also provided herein.

Variants of antibody molecules disclosed herein may be produced and used in the present invention. Following the lead of computational chemistry in applying multivariate data analysis techniques to the structure/property-activity relationships [81] quantitative activity-property relationships of antibodies can be derived using well-known mathematical techniques, such as statistical regression, pattern recognition and classification [82, 83, 84, 85, 86, 87]. The properties of antibodies can be derived from empirical and theoretical models (for example, analysis of likely contact residues or calculated physicochemical property) of antibody sequence, functional and three-dimensional structures and these properties can be considered singly and in combination.

An antibody antigen-binding site composed of a VH domain and a VL domain is typically formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites [88,89]. These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions [88, 89].

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimization experiments. In a structural approach, a model can be created of the antibody molecule [90] using any freely available or commercial package, such as WAM [91]. A protein visualisation and analysis software package, such as insight II (Accelrys, Inc, San Diego, USA.) or Deep View [92] may then be used to evaluate possible substitutions at each position in the CDR. This information may then be used to make substitutions likely to have a minimal or beneficial effect on activity.

The techniques required to make substitutions within amino acid sequences of CDRs, antibody VH or VL domains and binding members generally are available in the art. Variant sequences may be made, with substitutions that may or may not be predicted to have a minimal or beneficial effect on activity, and tested for ability to bind and/or neutralize IL-1R1 and/or for any other desired property.

Variable domains employed in the invention may be obtained or derived from any germline or rearranged human variable domain, or may be a synthetic variable domain based on consensus or actual sequences of known human variable domains. A variable domain can be derived from a non-human antibody. A CDR sequence of the invention (e.g. HCDR3) may be introduced into a repertoire of variable domains lacking a CDR (e.g. HCDR3), using recombinant DNA technology. For example, Marks et al. [93] describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR2. Marks et al. further describe how this repertoire may be combined with a CDR2 of a particular antibody. Using analogous techniques, the CDR2-derived sequences of the present invention may be shuffled with repertoires of VH or VL domains lacking a CDR2, and the shuffled complete VH or VL domains combined with a cognate VL or VH domain to provide binding members of the invention. The repertoire may then be displayed in a suitable host system, such as the phage display system of WO92/01047, which is herein incorporated by reference in its entirety, or any of a subsequent large body of literature, including Kay, Winter & McCafferty [94], so that suitable binding members may be selected. A repertoire may consist of from anything from $10^4$ individual members upwards, for example at least $10^5$, at least $10^6$, at least $10^7$, at least $10^8$, at least $10^9$ or at least $10^{10}$ members or more. Other suitable host systems include, but are not limited to yeast display, bacterial display, T7 display, viral display, cell display, ribosome display and covalent display.

A method of preparing a binding member for IL-1R1 antigen is provided, which method comprises:

(a) providing a starting repertoire of nucleic acids encoding a VH domain which either include a CDR2 to be replaced or lack a CDR2 encoding region;

(b) combining said repertoire with a donor nucleic acid encoding an amino acid sequence substantially as set out herein for a VH CDR2 such that said donor nucleic acid is inserted into the CDR2 region in the repertoire, so as to provide a product repertoire of nucleic acids encoding a VH domain;

(c) expressing the nucleic acids of said product repertoire;

(d) selecting a binding member for IL-1R1; and (e) recovering said binding member or nucleic acid encoding it.

Again, an analogous method may be employed in which a VH or VL CDR3 of the invention is combined with a repertoire of nucleic acids encoding a VH or VL domain that either include a CDR3 to be replaced or lack a CDR3 encoding region.

Similarly, one or more, or all three CDRs may be grafted into a repertoire of VH or VL domains that are then screened for a binding member or binding members for IL-1R1.

Similarly, other VH and VL domains, sets of CDRs and sets of HCDRs and/or sets of LCDRs disclosed herein may be employed.

A substantial portion of an immunoglobulin variable domain may comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including antibody constant regions, other variable domains (for example in the production of diabodies) or detectable/functional labels as discussed in more detail elsewhere herein.

Although in some aspects of the invention, binding members comprise a pair of VH and VL domains, single binding domains based on either VH or VL domain sequences form further aspects of the invention. It is known that single immunoglobulin domains, especially VH domains, are capable of binding target antigens in a specific manner. For example, see the discussion of dAbs.

In the case of either of the single binding domains, these domains may be used to screen for complementary domains capable of forming a two-domain binding member able to bind IL-1R1. This may be achieved by phage display screening methods using the so-called hierarchical dual combinatorial approach as disclosed in WO92/01047, herein incorporated by reference in its entirety, in which an individual colony containing either an H or L chain clone is used to infect a complete library of clones encoding the other chain (L or H) and the resulting two-chain binding member is selected in accordance with phage display techniques, such as those described in that reference. This technique is also disclosed in Marks et al, ibid.

As used herein, the twenty standard "amino acids" and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ϵ-N,N,N-trimethyllysine, ϵ-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As used herein the term "allotype" is used with respect to antigenic determinants specified by allelic forms of antibody genes. Allotypes represent slight differences in the amino acid sequences of heavy or light chains of different individuals and are sequence differences between alleles of a subclass whereby an antisera recognize only the allelic differences. The most important types are Gm (heavy chain) and Km (light chain). Gm polymorphism is determined by the IGHG1, IGHG2 and IGHG3 genes which have alleles encoding allotypic antigenic determinants referred to as G1m, G2m, and G3m allotypes for markers of the human IgG1, IgG2 and IgG3 molecules. At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b5, b0, b3, b4, s, t, g 1, c5, u, v, g5) (Lefranc, et al., The human IgG subclasses: molecular analysis of structure, function and regulation. Pergamon, Oxford, pp. 43-78 (1990); Lefranc, G. et al., 1979, Hum. Genet.: 50, 199-21 1, both incorporated entirely by reference).

Allelic forms of human immunoglobulins have been well-characterized (WHO Review of the notation for the allotypic and related markers of human immunoglobulins. J Immunogen 1976, 3: 357-362; WHO Review of the notation for the allotypic and related markers of human immunoglobulins. 1976, Eur. J. Immunol. 6, 599-601; E. van Loghem, 1986, Allotypic markers, Monogr Allergy 19: 40-51, all incorporated entirely by reference). Additionally, other polymorphisms have been characterized (Kim et al., 2001, J. Mol. Evol. 54:1-9, incorporated entirely by reference).

As used herein the term "antibody" refers to an oligoclonal, a polyclonal antibody, a monoclonal antibody, a chimeric antibody, a CDR-grafted antibody, a multi-specific antibody, a bi-specific antibody, a catalytic antibody, a chimeric antibody, a humanized antibody, a fully human antibody or an anti-idiotypic antibody and antibodies that can be labeled in soluble or bound form as well as fragments, variants or derivatives thereof, either alone or in combination with other amino acid sequences provided by known techniques. An antibody may be from any species. The term antibody also includes binding fragments of the antibodies of the invention; exemplary fragments include Fv, Fab, Fab', Fab'-SH, single stranded antibody (svFC), dimeric variable region (Diabody), triabodies, tetrabodies, minibodies and disulphide stabilized variable region (dsFv).

An antibody typically has a tetrameric form, comprising two identical pairs of polypeptide chains, each pair having one "light" and one "heavy" chain. The variable regions of each light/heavy chain pair form an antibody binding site. An antibody refers to an antibody whether natural or partly or wholly synthetically produced. It must be understood here that the invention does not relate to the antibodies in natural form, that is to say they are not in their natural environment but have been isolated or obtained by purification from natural sources, or else obtained by genetic recombination, or by chemical synthesis, including modification with unnatural amino acids.

An antibody other than a "bispecific" or "bifunctional" antibody is understood to have each of its binding sites identical. An antibody substantially inhibits binding of a ligand to a receptor when an excess of antibody reduces the quantity of ligand bound to receptor by at least about 20%, 40%, 40%, 60% or 80%, and more usually greater than about 85% (as measured in an in vitro competitive binding assay).

As used herein, the term "antigen-binding site" is the part of a molecule that binds to and is complementary to all or part of the target antigen. In an antibody molecule it is referred to as the antibody antigen-binding site, and comprises the part of the antibody that binds to and is complementary to all or part of the target antigen. Where an antigen is large, a binding member may only bind to a particular part of the antigen, which part is termed an epitope. An antibody antigen-binding site may be provided by one or more antibody variable domains. An antigen binding site of an antibody is generally formed by the variable heavy (VH) and variable light (VL) immunoglobulin domains, with the antigen-binding interface formed by six surface polypeptide loops, termed complementarity determining regions (CDRs). There are three CDRs in each VH(HCDR1, HCDR2, HCDR3) and in each VL LCDR1, LCDR2, LCDR3), together with framework regions (FRs).

As used herein, the term "binding member" refers to a polypeptide or group of polypeptides that are comprised of at least one antigen binding site that is formed from the folding of polypeptide chains having three-dimensional binding spaces with internal surface shapes and charge distributions complementary to the features of an antigenic determinant of an antigen. In one embodiment, the binding member is specific for only one target site. In other embodiments, the binding member is specific for more than one target site. In one embodiment a binding member is an antibody, for example a monoclonal antibody.

As used herein the term "chimeric antibody" refers to molecules comprising an antibody antigen-binding site, or equivalent, fused to another polypeptide (e.g. derived from another species or belonging to another antibody class or subclass) are therefore included. Cloning and expression of chimeric antibodies are described in EP-A-0120694 and EP-A-0125023, and a large body of subsequent literature.

As used herein the term 'competes' indicates that the binding member competes for binding to IL-1R1 with any one of antibodies 1 to 10, i.e. competition is unidirectional.

As herein the term 'cross competes' indicates that the binding member competes for binding to IL-1R1 with any one of antibodies 1 to 10, and vice versa, i.e. competition is bidirectional.

As used herein the term 'complementarily determining region' (CDR) is intended to indicate the hypervariable regions of the heavy and light chains of the immunoglobulin as defined by Kabat et al. 1991 [95], and later editions. An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It may be as short as 2 amino acids although the longest size known is 26. CDR length may also vary according to the length that can be accommodated by the particular underlying framework. Functionally, HCDR3 plays a role in part in the determination of the specificity of the antibody [see references 96, 97, 98, 99, 100, 101, 102, 103].

As used herein, the term "epitope" includes any protein determinant capable of specific binding to a binding member, for example an immunoglobulin or T-cell receptor. Epitopic determinants usually consist of chemically active surface groupings of molecules such as amino acids or sugar side chains and may, but not always, have specific three-dimensional structural characteristics, as well as specific charge characteristics. An antibody is said to specifically bind an antigen when the dissociation constant is $\leq 1$ µM, preferably $\leq 100$ nM and most preferably $\leq 10$ nM.

As used herein the term "framework" refers to any combination of atoms, for example amino acids, which can hold one or more CDRs in a configuration which binds IL-1R1.

As used herein the term "Fv" refers to the minimum fragment of an antibody that retains both antigen-recognition and antigen-binding sites.

As used herein the term "Fab" refers to a fragment of an antibody that comprises the constant domain of the light chain and the CH1 domain of the heavy chain.

As used herein the term "huIL" refers to human interleukin.

As used herein the term "IL-1R1" means interleukin 1 receptor 1. The amino acid sequence of the IL-1R1 is publicly available (RefSeq NM_00877). In some embodiments IL-1R1 may be human or cynomolgus monkey IL-1R1. As described elsewhere herein, IL-1R1 may be recombinant, and/or may be either glycosylated or unglycosylated.

As used herein the term "Geomean" (also known as geometric mean), refers to the average of the logarithmic values of a data set, converted back to a base 10 number. This requires there to be at least two measurements, e.g. at least 2, preferably at least 5, more preferably at least 10 replicate. The person skilled in the art will appreciate that the greater the number of replicates the more robust the geomean value will be. The choice of replicate number can be left to the discretion of the person skilled in the art.

As used herein the term "Isolated" refers to the state in which binding members of the invention, or nucleic acid encoding such binding members, will generally be in accordance with the present invention. Thus, binding members, VH and/or VL domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes of origin other than the sequence encoding a polypeptide with the required function. Isolated members and isolated nucleic acid will be free or substantially free of material with which they are naturally associated, such as other polypeptides or nucleic acids with which they are found in their natural environment, or the environment in which they are prepared (e.g. cell culture) when such preparation is by recombinant DNA technology practiced in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

Heterogeneous preparations comprising anti-IL-1R1 antibody molecules also form part of the invention. For example, such preparations may be mixtures of antibodies with full-length heavy chains and heavy chains lacking the C-terminal lysine, with various degrees of glycosylation and/or with derivatized amino acids, such as cyclization of an N-terminal glutamic acid to form a pyroglutamic acid residue.

As used herein the term "monoclonal antibody" refers to an antibody from a substantially homogeneous population of antibodies that specifically bind to the same epitope. The term "mAb" refers to monoclonal antibody.

As used herein, the phrase "substantially as set out" refers to the characteristic(s) of the relevant CDRs of the VH or VL domain of binding members described herein will be either identical or highly similar to the specified regions of which the sequence is set out herein. As described herein, the phrase "highly similar" with respect to specified region(s) of one or more variable domains, it is contemplated that from 1 to about 6, e.g. from 1 to 5, including 1 to 3, or 1 or 2, or 3 or 4, amino acid substitutions may be made in the CDR and/or VH or VL domain.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

BRIEF DESCRIPTION OF THE TABLES AND FIGURES

Table 1a lists the amino acid sequences of the heavy and lightchain CDRs of each of antibodies 1-3.

Table 1b lists the amino acid sequences of the heavy and light chain CDRs of each of antibodies 4-10

Table 2 shows the sequences of exemplary binding members of the invention as shown in the appended sequence listing, in which SEQ ID numbers correspond as shown in Table 3.

Table 3 shows examples of lead scFv potencies in the HTRF® human receptor-ligand IL1β binding assay Table 4 shows examples of lead IgG1 potencies in the human IL-1β induced IL-8 release assay Table 5. shows optimised IgG1 and GL IgG2 potency for inhibition of IL-α- or IL-1β-induced IL-8 release in HeLa cells.

Table 6. shows potency of IL-1R family members and different IL-1R species in human IL-1R binding optimised IgG assay (DELFIA®).

Table 7. shows inhibition by optimised IgG in receptor-ligand (IL1Ra) HTRF®L binding assay.

Table 8. shows inhibition by optimised IgG of IL-1β induced IL-8 release from CYNOM-K1 cells expressing endogenous cynomolgus IL-1R Table 9. shows $IC_{50}$ values for inhibition of IL-1β induced IL-6 production in human whole blood.

Table 10, shows the results of affinity measurements for an anti-IL-1R1 FAb to soluble human IL-1R1 and soluble cynomolgus IL-1R1.

Table 11. shows the results of affinity measurements for Antibody 6 and AMG108 binding to soluble human IL-1R1.

Table 12. shows the $IC_{50}$ (in nM) of chimeric IL-1R1 molecules competing against human IL-1R1 binding to antibody FIG. 1. shows the sequence of Cynomolgus Monkey IL-1R1 extracellular domain cDNA [SEQ ID NO: 131]

FIG. 2. shows the sequence of Cynomolgus Monkey IL-1R1 extracellular domain amino acid sequence [SEQ ID NO: 132]

FIG. 3 shows the Human IL1R1Fc cDNA nucleotide sequence [SEQ ID NO: 133]

FIG. 4 shows the Human IL1R1Fc protein sequence [SEQ ID NO: 134]

FIG. 5 shows the Cynomolgus Monkey IL1R1Fc cDNA nucleotide sequence [SEQ ID NO: 135]

FIG. 6 shows the Cynomolgus Monkey IL1R1Fc protein sequence [SEQ ID NO: 136]

FIG. 7 shows the Human IL-1R1 extracellular sequence [SEQ ID NO: 137]

FIG. 8 shows the Human IL-1R1 cDNA sequence [SEQ ID NO: 138]

FIG. 9 shows the Cyno IL-1R1 Extracellular sequence (residues 1 to 337) [SEQ ID NO: 139]

FIG. 10 shows the Cyno cDNA extracellular IL-1R1 sequence [SEQ ID NO: 140]

FIG. 11 shows the sequence of mature human HIS-FLAG IL-1ra [SEQ ID NO: 141]

FIG. 12 shows the sequence of mature human HIS-FLAG IL-1β [SEQ ID NO: 142]

Figure 13:
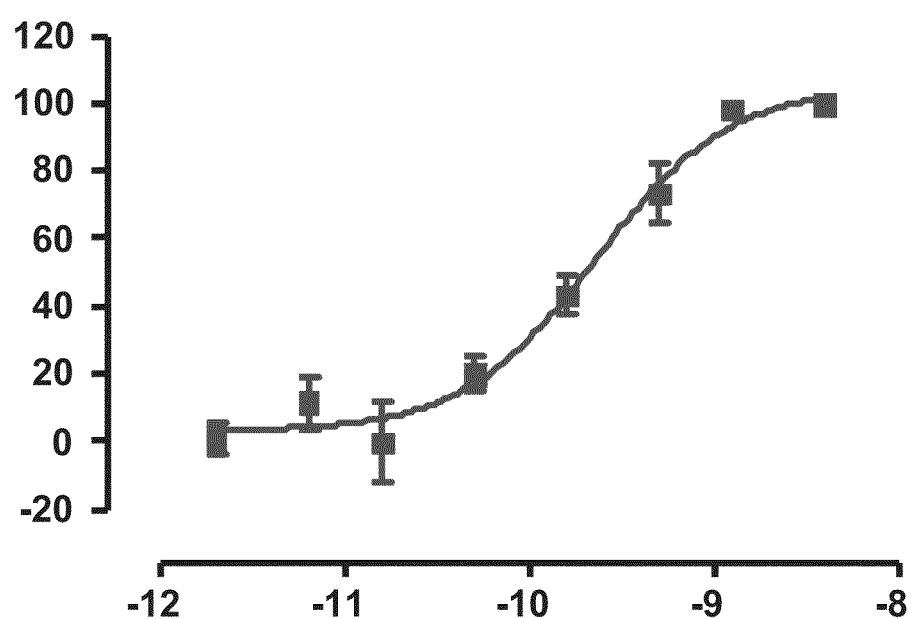

FIG. 13. shows the inhibition of IL-1β induced IL-6 production in human whole blood for Antibody 6 IgG2 (Example 2.7). The x axis shows the concentration of Antibody 6 (Log molar) and the Y axis is percentage inhibition of IL6 production.

FIG. 14. shows the SDCAT-CG primer which converts Glu to Gln in the Ribosome Display Construction and Retrieval of the Vh3_DP-47_(3-23) family

EXAMPLES

Naïve human single chain Fv (scFv) phage display libraries cloned in to a phagemid vector based on the filamentous phage M13 were used for selections [104, 105]).

Anti-IL-1R1 specific scFv antibodies are isolated from the phage display libraries using a series of selection cycles on recombinant human IL-1R1.

Selected scFv antibodies are optimized for binding to human IL-1R1 and/or for potency, and are reformatted as IgG antibodies.

Sequences

Sequences of exemplary binding members of the invention are shown in the appended sequence listing, in which SEQ ID NOS correspond as shown in Table 2 below wherein:
i) where an antibody number is followed by GL, for example 11GL this refers to the antibody wherein one or more of the residues have been mutated back to the germline configuration, in general where GL is used all non-germline residues which can be mutated back to germline without appreciable loss of activity have been germlined. It should be noted that in the specification where any one or all of antibodies 1 to 10 are referred to this also includes any germlined variants listed in Table 2.

And the CDRs are shown in Tables 1a and 1b.

TABLE 1a

| Kabat | HCDR1 | | | | | HCDR2 | | | | | | | | | | | | | | |
|---|---|---|---|---|---|---|---|---|---|---|---|---|---|---|---|---|---|---|---|---|
| numbering | 31 | 32 | 33 | 34 | 35 | 50 | 51 | 52 | 52A | 53 | 54 | 55 | 56 | 57 | 58 | 59 | 60 | 61 | 62 | 63 | 64 | 65 |
| Antibody 1 | S | Y | A | | S | A | I | S | G | S | G | G | S | T | Y | Y | A | D | S | V | K | G |
| Antibody 2 | | | | | | | | | | | | | | | | | | | | | | |
| Antibody 3 | | | | | | | | | | | | | | | | | | | | | | |

| Kabat | HCDR3 | | | | | | | | | | | | | | | |
|---|---|---|---|---|---|---|---|---|---|---|---|---|---|---|---|---|
| numbering | 95 | 96 | 97 | 98 | 99 | 100 | 100A | 100B | 100C | 100D | 100E | 100F | 100G | 100H | 100I | 101 | 102 |
| Antibody 1 | D | G | A | S | S | T | N | W | G | Y | N | Y | Y | G | M | D | V |
| Antibody 2 | | | | | | | | | | | T | V | D | A | A | V | D |
| Antibody 3 | | | | | | | | | | | T | L | D | P | P | G | V |

| Kabat | LCDR1 | | | | | | | | | | | | LCDR2 | | | | | |
|---|---|---|---|---|---|---|---|---|---|---|---|---|---|---|---|---|---|---|
| numbering | 24 | 25 | 26 | 27 | 27A | 27B | 28 | 29 | 30 | 31 | 32 | 33 | 34 | 50 | 51 | 52 | 53 | 54 | 55 | 56 |
| Antibody 1 | S | G | S | S | S | N | I | G | S | N | Y | V | F | W | N | N | Q | R | P | S |
| Antibody 2 | | | | | | | | | | | | | | | | | | | | |
| Antibody 3 | | | | | | | | | | | | | | | | | | | | |

| Kabat | LCDR3 | | | | | | | | | |
|---|---|---|---|---|---|---|---|---|---|---|
| numbering | 89 | 90 | 91 | 92 | 93 | 94 | 95 | 95A | 95B | 96 | 97 |
| Antibody 1 | A | A | W | D | D | S | L | S | G | L | V |
| Antibody 2 | | | | | | H | | E | Q | | H |
| Antibody 3 | | | | | | A | A | R | V | | L |

TABLE 1b

| Kabat | HCDR1 | | | | | HCDR2 | | | | | |
|---|---|---|---|---|---|---|---|---|---|---|---|
| numbering | 31 | 32 | 33 | 34 | 35 | 50 | 51 | 52 | 52A | 53 | 54 | 55 |
| Antibody 4 | S | Y | A | M | S | A | I | S | G | S | G | G |
| Antibody 5 | | | | | | | | | | | | |
| Antibody 6 | | | | | | | | | | | | |
| Antibody 7 | | | | | | | | | | | | |
| Antibody 8 | | | | | | | | | | | | |
| Antibody 9 | | | | | | | | | | | | |
| Antibody 10 | | | | | | | | | | | | |

| Kabat | HCDR2 | | | | | | | | | HCDR3 | | |
|---|---|---|---|---|---|---|---|---|---|---|---|---|
| numbering | 56 | 57 | 58 | 59 | 60 | 61 | 62 | 63 | 64 | 65 | 95 | 96 | 97 |
| Antibody 4 | S | T | Y | Y | A | D | S | Y | X | G | P | L | Y |
| Antibody 5 | | | | | | | | | | | | | |
| Antibody 6 | | | | | | | | | | | | | |
| Antibody 7 | | | | | | | | | | | | | |
| Antibody 8 | | | | | | | | | | | | | |
| Antibody 9 | | | | | | | | | | | | | |
| Antibody 10 | | | | | | | | | | | | | |

TABLE 1b-continued

| Kabat numbering | HCDR3 | | | | | | | | | | |
|---|---|---|---|---|---|---|---|---|---|---|---|
| | 98 | 99 | 100 | 100A | 100B | 100C | 100D | 100E | 100F | 100G | 100H | 100I |
| Antibody 4 | Y | Y | D | G | S | D | Y | T | T | Y | D | A |
| Antibody 5 | | | | A | P | P | P | L | G | | | G |
| Antibody 6 | | | | E | Q | Y | G | V | V | | | |
| Antibody 7 | | | | A | A | P | P | L | G | | | G |
| Antibody 8 | | | | A | P | S | P | L | G | | | G |
| Antibody 9 | | | | E | Q | Y | G | L | V | | | |
| Antibody 10 | | | | E | | L | A | L | P | V | Y | D |

| Kabat numbering | HCDR3 | | | LCDR1 | | | | | | | | |
|---|---|---|---|---|---|---|---|---|---|---|---|---|
| | 100J | 101 | 102 | 24 | 25 | 26 | 27 | 27A | 27B | 27C | 28 | 29 | 30 |
| Antibody 4 | F | D | I | T | G | S | S | S | N | I | G | A | G |
| Antibody 5 | | | | | | | | | | | | | |
| Antibody 6 | / | F | V | | | | | | | | | | |
| Antibody 7 | | | | | | | | | | | | | |
| Antibody 8 | | | | | | | | | | | | | |
| Antibody 9 | | | | | | | | | | | | | |
| Antibody 10 | A | | | | | | | | | | | | |

| Kabat numbering | LCDR1 | | | | LCDR2 | | | | | | |
|---|---|---|---|---|---|---|---|---|---|---|---|
| | 31 | 32 | 33 | 34 | 50 | 51 | 52 | 53 | 54 | 55 | 56 |
| Antibody 4 | Y | D | V | H | G | D | T | H | R | P | S |
| Antibody 5 | | | | | | | | | | | |
| Antibody 6 | | | | | | | | | | | |
| Antibody 7 | | | | | | | | | | | |
| Antibody 8 | | | | | | | | | | | |
| Antibody 9 | | | | | | | | | | | |
| Antibody 10 | | | | | | | | | | | |

| Kabat numbering | LCDR3 | | | | | | | | | |
|---|---|---|---|---|---|---|---|---|---|---|
| | 89 | 90 | 91 | 92 | 93 | 94 | 95 | 95A | 95B | 96 | 97 |
| Antibody 4 | Q | S | Y | D | T | S | L | S | G | S | L |
| Antibody 5 | | | | | | A | G | G | | H | H |
| Antibody 6 | | | | | | V | R | L | H | H | V |
| Antibody 7 | | | | | | D | A | A | R | H | Q |
| Antibody 8 | | | | | | H | | V | A | H | V |
| Antibody 9 | | | | | | L | | L | A | P | Q |
| Antibody 10 | | | | | | R | A | D | D | A | H |

TABLE 2

| Antibody | SEQ ID No. | Description |
|---|---|---|
| 1 | 91 | VH/DNA |
| 1 | 92 | VH/amino acid |
| 1 | 93 | HCDR1 |
| 1 | 94 | HCDR2 |
| 1 | 95 | HCDR3 |
| 1 | 96 | VL/DNA |
| 1 | 97 | VL/amino acid |
| 1 | 98 | LCDR1 |
| 1 | 99 | LCDR2 |
| 1 | 100 | LCDR3 |
| 2 | 1 | VH/DNA |
| 2 | 2 | VH/amino acid |
| 2 | 3 | HCDR1 |
| 2 | 4 | HCDR2 |
| 2 | 5 | HCDR3 |
| 2 | 6 | VL/DNA |
| 2 | 7 | VL/amino acid |
| 2 | 8 | LCDR1 |
| 2 | 9 | LCDR2 |
| 2 | 10 | LCDR3 |
| 3 | 121 | VH/DNA |
| 3 | 122 | VH/amino acid |
| 3 | 123 | HCDR1 |
| 3 | 124 | HCDR2 |
| 3 | 125 | HCDR3 |
| 3 | 126 | VL/DNA |
| 3 | 127 | VL/amino acid |
| 3 | 128 | LCDR1 |
| 3 | 129 | LCDR2 |
| 3 | 130 | LCDR3 |
| 4 | 101 | VH/DNA |
| 4 | 102 | VH/amino acid |
| 4 | 103 | HCDR1 |
| 4 | 104 | HCDR2 |
| 4 | 105 | HCDR3 |
| 4 | 106 | VL/DNA |
| 4 | 107 | VL/amino acid |
| 4 | 108 | LCDR1 |
| 4 | 109 | LCDR2 |
| 4 | 110 | LCDR3 |
| 5 | 11 | VH/DNA |
| 5 | 12 | VH/amino acid |
| 5 | 13 | HCDR1 |
| 5 | 14 | HCDR2 |
| 5 | 15 | HCDR3 |
| 5 | 16 | VL/DNA |
| 5 | 17 | VL/amino acid |
| 5 | 18 | LCDR1 |
| 5 | 19 | LCDR2 |
| 5 | 20 | LCDR3 |

TABLE 2-continued

| Antibody | SEQ ID No. | Description |
| --- | --- | --- |
| 6 | 61 | VH/DNA |
| 6 | 62 | VH/amino acid |
| 6 | 63 | HCDR1 |
| 6 | 64 | HCDR2 |
| 6 | 65 | HCDR3 |
| 6 | 66 | VL/DNA |
| 6 | 67 | VL/amino acid |
| 6 | 68 | LCDR1 |
| 6 | 69 | LCDR2 |
| 6 | 70 | LCDR3 |
| 6GL | 21 | VH/DNA |
| 6GL | 22 | VH/amino acid |
| 6GL | 23 | HCDR1 |
| 6GL | 24 | HCDR2 |
| 6GL | 25 | HCDR3 |
| 6GL | 26 | VL/DNA |
| 6GL | 27 | VL/amino acid |
| 6GL | 28 | LCDR1 |
| 6GL | 29 | LCDR2 |
| 6GL | 30 | LCDR3 |
| 7 | 31 | VH/DNA |
| 7 | 32 | VH/amino acid |
| 7 | 33 | HCDR1 |
| 7 | 34 | HCDR2 |
| 7 | 35 | HCDR3 |
| 7 | 36 | VL/DNA |
| 7 | 37 | VL/amino acid |
| 7 | 38 | LCDR1 |
| 7 | 39 | LCDR2 |
| 7 | 40 | LCDR3 |
| 8 | 71 | VH/DNA |
| 8 | 72 | VH/amino acid |
| 8 | 73 | HCDR1 |
| 8 | 74 | HCDR2 |
| 8 | 75 | HCDR3 |
| 8 | 76 | VL/DNA |
| 8 | 77 | VL/amino acid |
| 8 | 78 | LCDR1 |
| 8 | 79 | LCDR2 |
| 8 | 80 | LCDR3 |
| 8GL | 41 | VH/DNA |
| 8GL | 42 | VH/amino acid |
| 8GL | 43 | HCDR1 |
| 8GL | 44 | HCDR2 |
| 8GL | 45 | HCDR3 |
| 8GL | 46 | VL/DNA |
| 8GL | 47 | VL/amino acid |
| 8GL | 48 | LCDR1 |
| 8GL | 49 | LCDR2 |
| 8GL | 50 | LCDR3 |
| 9 | 111 | VH/DNA |
| 9 | 112 | VH/amino acid |
| 9 | 113 | HCDR1 |
| 9 | 114 | HCDR2 |
| 9 | 115 | HCDR3 |
| 9 | 116 | VL/DNA |
| 9 | 117 | VL/amino acid |
| 9 | 118 | LCDR1 |
| 9 | 119 | LCDR2 |
| 9 | 120 | LCDR3 |
| 9GL | 51 | VH/DNA |
| 9GL | 52 | VH/amino acid |
| 9GL | 53 | HCDR1 |
| 9GL | 54 | HCDR2 |
| 9GL | 55 | HCDR3 |
| 9GL | 56 | VL/DNA |
| 9GL | 57 | VL/amino acid |
| 9GL | 58 | LCDR1 |
| 9GL | 59 | LCDR2 |
| 9GL | 60 | LCDR3 |
| 10GL | 81 | VH/DNA |
| 10GL | 82 | VH/amino acid |
| 10GL | 83 | HCDR1 |
| 10GL | 84 | HCDR2 |
| 10GL | 85 | HCDR3 |
| 10GL | 86 | VL/DNA |
| 10GL | 87 | VL/amino acid |
| 10GL | 88 | LCDR1 |
| 10GL | 89 | LCDR2 |
| 10GL | 90 | LCDR3 |

The invention will now be exemplified by the following non-limiting examples:

Example 1

Antibody Lead Isolation 1.1 Selections

Large single chain Fv (scFv) human antibody libraries cloned into a phagemid vector based on filamentous phage M13 were used for selections (106, 107). Anti-IL-1R specific scFv antibodies were isolated from the phage display libraries using a series of selection cycles on biotinylated recombinant human IL-1R-Fc essentially as previously described (108), In brief, the scFv-phage particles were incubated with 100 nM recombinant biotinylated human IL-1R-Fc fusion protein in solution (huIL-1R1-Fc fusion protein as described in Materials and Methods and biotinylated in-house). ScFv-phage bound to antigen were then captured on streptavidin-coated paramagnetic beads (Dynabeads® M-280) following the manufacturer's recommendations. The selected scFv-phage particles were then rescued as described previously (109), and the selection process was repeated for a second round.

A representative number of individual clones from the second round of selections was grown up in 96-well plates. ScFvs were expressed in bacterial periplasm and screened for their inhibitory activity in a human receptor-ligand (IL-1β) binding HTRF assay, described in Materials and Methods. ScFv which showed a significant inhibitory effect in this assay as crude periplasmic extracts, were subjected to DNA sequencing (106, 109). Unique scFvs were expressed again in bacteria and purified by affinity chromatography (110), and $IC_{50}$ values were determined by testing dilution series of purified scFvs in the same ligand-receptor binding assay.

1.2 Inhibition by scFv in a Receptor-Ligand (IL-1β) Binding Assay

Selection outputs were screened in receptor-ligand binding HTRF® (Homogeneous Time-Resolved Fluorescence) assay format for inhibition of HIS FLAG tagged human IL1 beta (In house, E. coli expressed; HIS FLAG IL-1 beta) binding to human histidine tagged (HIS) IL1RFc fusion protein (in house).

The detailed assay method, and material expression method, is provided in the Materials and Methods section.

Examples of the lead scFv potencies obtained from the binding assay are shown in Table 3.

TABLE 3

Examples of lead scFv potencies in the HTRF ® human receptor-ligand IL1β binding assay

| Clone name | $IC_{50}$ (nM) in HTRF ® assay |
| --- | --- |
| Antibody 1 | IC 225 nM |
| Antibody 4 | 22.5 nM |
| Kineret | 0.323 nM |

IC = Incomplete inhibition curve; IC50 values are estimated

Data is from single experiment that is representative of several independent experiments

1.3 Reformatting of scFv to IgG1

Clones that were identified as inhibitory in the receptor-ligand HTRF binding assay were converted from scFv to IgG$_1$ format by sub-cloning the V$_H$ and V$_L$ domains into vectors expressing whole antibody heavy and light chains respectively. The V$_H$ domain was cloned into a vector (pEU15.1) containing the human heavy chain constant domains and regulatory elements to express whole IgG heavy chain in mammalian cells. Similarly, the V$_L$ domain was cloned into a vector (pEU4.4) for the expression of the human light chain (lambda) constant domains and regulatory elements to express whole IgG light chain in mammalian cells. Vectors for the expression of heavy chains and light chains were based on those originally described in reference (111). Our vectors have been engineered simply by introducing an OriP element. To obtain IgGs, the heavy and light chain IgG expressing vectors were transfected into EBNA-HEK293 mammalian cells. IgGs were expressed and secreted into the medium. Harvests were pooled and filtered prior to purification, then IgG was purified using Protein A chromatography. Culture supernatants were loaded on a column of appropriate size of Ceramic Protein A (BioSepra) and washed with 50 mM Tris-HCl pH 8.0, 250 mM NaCl. Bound IgG was eluted from the column using 0.1 M Sodium Citrate (pH 3.0) and neutralised by the addition of Tris-HCl (pH 9.0). The eluted material was buffer exchanged into PBS using Nap 10 columns (Amersham, #17-0854-02) and the concentration of IgG was determined spectrophotometrically using an extinction coefficient based on the amino acid sequence of the IgG (112). The purified IgG were analysed for aggregation and degradation using SEC-HPLC and by SDS-PAGE.

1.4 Germlining of Parents KENB026 and KENB061

The amino acid sequences of the V$_H$ and V$_L$ domains of the parent antibodies Antibody 1 and Antibody 4 that were inhibitory in the biological assay were aligned to the known human germline sequences in the VBASE database (113), and the closest germline was identified by sequence similarity. Without considering the Vernier residues (114), which were left unchanged, changes in frameworks of the VH and VL domains were reverted to the closest germline sequence to identically match human antibodies, using standard site directed mutagenesis techniques with the appropriate mutagenic primers. These mutagenesis procedures were performed in the IgG vectors for parent.

1.5 Germlining the Lead Antibodies as IgG2

The parent Antibody 4 (in IgG1 format) was used as a template for mutagenesis for germlining lead antibodies. The individual VH and VL CDR3 sequences of leads were introduced into the germlined parent in the IgG1 vector to produce germlined leads using standard site directed mutagenesis techniques with appropriate primers.

The IgG1 to IgG2 conversion was conducted using standard cloning procedures. IgG1 VH lead plasmids were isolated and the germlined VH removed for cloning into the IgG2 VH vector.

Germline Information

Antibody 1: VH Vh3_DP-47_(3-23), Vl Vlambda1_DPL3_(1g).

| Position | Antibody amino acid | Germline amino acid | Changed? |
|---|---|---|---|
| Antibody 1 Vh94 | Arg | Lys | No |
| Antibody 2 Vh108 | Thr | Leu | No |
| Antibody 3 Vl2 | Ala | Ser | No |
| Vl 8 | Ser | Pro | No |
| Vl 39 | Phe | Leu | No |
| Vl 45 | Gln | Lys | No |
| Vl 48 | Val | Ileu | No |
| Vl 49 | Lys | Tyr | No |

Antibody 4: VH Vh3_DP-47_(3-23), Vl Vlambda1_DPL8_(1e).

| | Position | Antibody amino acid | Germline amino acid | Changed? |
|---|---|---|---|---|
| Antibody 4 | Vh 108 | Met | Leu | No |
| Antibody 5 | Vl74 | Val | Ala | No |
| Antibody 6 | Vl76 | Ala | Thr | No |
| Antibody 7 | | | | |
| Antibody 8 | | | | |
| Antibody 9 | | | | |
| Antibody 7 | Vernier position 1 | Gln | Glu | Yes[1] |
| Antibody 8 | | | | |
| Antibody 9 | | | | |
| Antibody 6 | VH CDR3 | 17 amino acids | 18 amino acids | No[2] |
| Antibody 9 | Vh103 | Gly | Trp | No |

[1] This is because of a base change from GAA (Glu) to CAA (Gln) when using the primer SDCATCG (see primer and Vh3_DP-47_(3-23) frame-work sequence alignment for ribosome display library construction and retrieval - FIG. 14). This residue (although vernier) was reverted back to Glutamic acid (Glu) during the germ-line process because it was artificially introduced. Antibody 6 was also amplified using SDCATCG but position 1 was corrected to a Glu during the IgG1 conversion process.
[2] This deletion is likely to have occurred during the ribosome display conversion and selection process. Ribosome display is a process that is PCR-based and uses an error prone polymerase.

1.6 Inhibition of IL-1-Induced IL-8 Release from HeLa Cells

To determine the bioactivity of IL-1R inhibitors, a panel of scFvs inhibitory in the receptor-ligand binding assay were converted to IgG and their activity was evaluated in a HeLa human cell assay by measuring dose-dependent inhibition of IL-1β- and IL-1α-induced IL-8 release. For details of the assay method, see the Materials and Methods section.

In this assay, the inhibitory activity of a panel of anti-IL-1R IgGs was determined in response to an EC$_{50}$ concentration of human IL-1β or IL-1α (defined as the concentration of IL-1 which gives a half maximal response in the assay; approx 2 pM in this case). Antibodies demonstrating any significant inhibition of the IL-1-induced response were taken forward into a lead isolation panel and examples are shown in Table 4. Germlined IgG$_1$ variants of Antibody 1 and Antibody 4 were also shown to be active in this assay.

TABLE 4

Examples of lead IgG1 potencies in the human IL-1β induced IL-8 release assay

| Clone Name | IC$_{50}$ (nM) (N = 2-5) |
|---|---|
| Antibody 1 | 95.9 |
| Antibody 4 | 22.0 |
| AMG 108 | 0.009 |
| Kineret | 0.01 |

IC$_{50}$s represent geometric means from 2 to 5 independent experiments

Example 2

Antibody Optimisation

2.1 Affinity Maturation

Antibody 4 and Antibody 1 were optimised using affinity-based phage and ribosome display selections.

Large scFv-phage libraries derived from the lead clones were created by oligonucleotide-directed mutagenesis of the variable heavy ($V_H$) and light ($V_L$) chain complementarity determining regions 3 (CDR3) using standard molecular biology techniques as described (115). The libraries were subjected to affinity-based phage display selections in order to select variants with higher affinity for human IL-1R-Fc. In consequence, these were expected to show an improved inhibitory activity for human IL-1β binding IL-1R1. The selections were performed essentially as described previously (108). In brief, the scFv-phage particles were incubated with recombinant biotinylated human IL-1R-Fc in solution. ScFv-phage bound to antigen were then captured on streptavidin-coated paramagnetic beads (Dynabeads® M-280) following the manufacturer's recommendations. The selected scFv-phage particles were then rescued as described previously (109), and the selection process was repeated in the presence of decreasing concentrations of biotinylated human IL-1R-1 (50 nM to 0.05 nM over 3 rounds).

Crude scFv-containing periplasmic extracts were prepared of a representative number of individual clones from the variable heavy (VH) and the variable light (VL) selection outputs and screened in a receptor-ligand binding HTRF® (Homogeneous Time-Resolved Fluorescence) assay format for inhibition of HIS FLAG tagged human IL1 beta (In house, *E. coli* expressed; HIS FLAG IL-1 beta) binding to human histidine tagged (HIS) IL1RFc fusion protein (in house). Screening hits, i.e. scFv variants, which showed a significantly improved inhibitory effect when compared to their respective parent antibody, were subjected to DNA sequencing, and unique variants from variable heavy and variable light library outputs were produced as purified scFv for further characterisation. Some scFv were then selected and were converted to IgG1 and tested again in an effort to realise additional potency gain.

The variable heavy (VH) and variable light (VL) selection outputs comprising of large numbers of scFv variants with the ability to inhibit the binding of human IL-1β to human IL-1RI were recombined to form a single library in phage display format in which clones contained randomly paired individually randomised VH and VL sequences. Phage selections were then continued as described previously in the presence of decreasing concentrations of biotinylated human IL-1R-Fc (0.1 nM to 5 pM over a further 3 rounds).

Alternatively, a ribosome display method was used to recombine selection outputs. For ribosome display, the variable heavy (VH) and variable light (VL) selection outputs comprising of large numbers of scFv variants with the ability to inhibit the binding of human IL-1β to human IL-1RI were recombined to form a single library by polymerase chain reaction (PCR) and adapted to ribosome display format essentially as described in reference 116. Ribosome display affinity-based selections were carried out on the recombined libraries and the selection process was repeated in the presence of decreasing concentrations of biotinylated-human IL-1RI (1 nM to 5 pM over 3 rounds). Ribosome display outputs were then cloned into a phage display vector for further characterisation essentially as described in reference 117.

Crude scFv-containing periplasmic extracts were prepared of a representative number of individual clones from the phage display and the ribosome display outputs and screened for their ability to inhibit the binding of human bio-human Il-1β to human Il-1RI receptor. Screening hits i.e. scFv variants, which showed a significantly improved inhibitory effect when compared to their respective parent antibody and leads generated prerecombination, were subjected to DNA sequencing and unique recombined variants were produced as purified scFv for further characterisation.

The most active scFv in this assay were converted to non-germline IgG$_1$ and/or germlined IgG$_2$ as described in Example 1.3 and 1.5, and were tested for specificity in a competition ELISA format, in the receptor-ligand IL-1Ra HTRF and the HeLa IL-1-beta and -alpha induced IL-8 release assays. The antibodies were also tested for cross-reactivity to cynomolgus IL-1R1.

2.3 Inhibition by Optimised IgGs of IL-1β- and IL-1α-Induced IL-8 Release from HeLa Cells Improvements in bioactivity of clones, following lead optimisation and reformatting to IgG, were assessed in the HeLa IL-8 release assay using huIL-1-beta and huIL-1 alpha (R&D Systems) at EC$_{80}$ concentrations (5 pM for both) as described in the Materials and Methods section. Results are shown in Table 5.

TABLE 5

Optimised IgG1 and GL IgG2 potency for inhibition IL- α- or IL-1β- induced IL-8 release in HeLa cells

| | IC$_{50}$ (pM) | | |
|---|---|---|---|
| | IgG1 | GLIgG2 | |
| Clone Name | IL-1 beta (N = 6-7) | IL-1 beta (N = 5-6) | IL-1 alpha (N = 3) |
| Antibody 2 | 77.5 | — | — |
| Antibody 3 | 49.4 | — | — |
| Antibody 5 | 32.0 | — | — |
| Antibody 6 | 7.8 | — | — |
| Antibody 6GL | — | 11.9 | 3.1 |
| Antibody 7 | 42.6 | — | — |
| Antibody 8 | 29.3 | — | — |
| Antibody 8 GL | — | 41.9 | 197.2 |
| Antibody 9 | 11.5 | — | — |
| Antibody 9 GL | — | 6.9 | 16.2 |
| Antibody 10GL | — | 24.2 | 13.8 |
| AMG 108 | 5.3 | 5.9 | 11.7 |
| Kineret | 6.2 | 2.0 | 1.7 |

IC$_{50}$ represent geometric means of the number of experiments indicated

A subset of clones with increased potency compared to parent were subsequently analysed in additional assays including cynomolgus IL-1R assay using CYNOM-K1 cells, (described in sections below and assay descriptions in Materials and Methods). Optimised antibodies were compared with IL-1Ra (Kineret®; Amgen, provided commercially from a pharmacy outlet) and AMG108 sequence from US 2004/0097712 published 20 May 2004).

2.4 Selectivity and Species Cross Reactivity of Optimized Antibodies in DEL 14® Epitope Competition Assays The selectivity and species cross reactivity of lead antibodies to IL-1R family members was established using DELFIA® epitope competition assays.

The assay measured the inhibition of biotinylated human HIS-IL1RFc (in house expressed and biotinylated in-house) binding each optimised anti-IL1R antibody.

Titrations of non biotinylated purified human recombinant IL1sRII (R&D Systems), human recombinant IL-1R6/IL1 R rp2/Fc (R&D Systems), human recombinant IL18R alpha/IL-1 R5/Fc (R&D systems) and recombinant human IL-1R4 (ST2)/Fc (R&D systems) were tested in each assay to establish the potency for each structurally related family member, as measured by $IC_{50}$ values in the assay.

Titrations of IL-1R species including human HIS-IL1RFc (in house), cynomologus HIS-IL1RFc (in house) and rat IL-1RFc (in house) were tested in each assay to establish the species cross-reactivity of the optimised antibodies.

Example results are summarized in Table 6. The results indicate that lead optimised antibodies were selective for human IL-1R and also similarly bound cynomolgus IL-1R, and did not recognise structurally related proteins. Rat IL-1R-Fc was not recognised by any of the optimised antibodies.

TABLE 6

Potency of IL-1R family members and different IL-1R species in human IL-1R binding optimised IgG assay (DELFIA ®)

| | $IC_{50}$ (nM) of IL-IR species/family members | | | | | | |
|---|---|---|---|---|---|---|---|
| Clone Name | Human his IL-1RFc | Cyno his IL1RFc | Rat his IL1RFc | Human IL1sRII | Human IL1R6Fc | IL18R alpha Fc | IL1R4 (ST2) Fc |
| Antibody 6GL | 0.199 | 0.405 | NI | NI | NI | NI | NI |
| Antibody 8GL | 0.241 | 0.454 | NI | NI | NI | NI | NI |
| Antibody 9GL | 0.145 | 0.261 | NI | NI | NI | NI | NI |
| Antibody 10GL | 0.096 | 0.186 | NI | NI | NI | NI | NI |

$IC_{50}$ values represent geometric mean of three independent experiments
NI: No inhibition of huIL-1RFc was observed 2.5 Inhibition by Optimised IgG in a Receptor-Ligand (IL-1Ra) Binding Assay The ability of lead antibodies to inhibit IL-1Ra to IL-1R1 was assessed in a receptor-ligand binding HTRF® (Homogeneous Time-Resolved Fluorescence) assay format for inhibition of HIS FLAG tagged human IL1Ra (In house, E. coli expressed; HIS FLAG IL-1RA) binding to human histidine tagged (HIS) IL1RFc fusion protein (in house), as described in the Materials and methods section.

This was to determine whether an advantageous epitope had been obtained, where the antibodies competed for binding for IL-1Ra to IL-1R1 in addition to IL-1-beta and IL-1-alpha. In vivo this would liberate receptor-bound IL-1Ra, thereby allowing it to bind to another receptor, which is believed to be advantageous. IL-1Ra may be able to access tissues otherwise poorly accessible to IgGs, and it may also penetrate tissues distal from the circulation faster than IgGs. It is declared in the patent for AMG108 Amgen (US2004/0097712A1) and Hoffmann-La Roche AG (WO 2005/023872) that these prior art antibodies do not directly compete with IL-1Ra binding to IL-1R1. It was discussed in Amgen's patent (US2004/0097712A1) that antibodies that competed with IL-1 but did not compete with the IL-1Ra showed superior potency in assays designed to show inhibition of IL-1-mediated effects to those that did compete with IL-1 and IL-1ra, and thus represented a superior epitope. We surprisingly report that antibodies that do inhibit IL-1ra as well as IL-1, can be similarly potent in inhibition assays of IL-1 activity to the antibodies described in US2004/0097712A1, that did not.

Example results are shown in table 7 below, confirming that prior art antibodies were not able to fully compete with IL-1Ra binding to IL-1R1, but that our lead antibodies completely inhibited this interaction, with $IC_{50}s$ as shown.

TABLE 7

Inhibition by optimised IgG in receptor-ligand (IL1Ra) HTRF ® binding assay

| Clone | $IC_{50}$ (nM) |
|---|---|
| Antibody 2 IgG1 | 0.256 |
| Antibody 3 IgG1 | 0.469 |
| Antibody 5 IgG1 | 0.186 |
| Antibody 6 IgG1 | 0.100 |
| Antibody 7 IgG1 | 0.168 |
| Antibody 8 IgG1 | 0.156 |
| Antibody 9 IgG1 | 0.156 |
| Antibody 6GL IgG2 | 0.181 |

TABLE 7-continued

Inhibition by optimised IgG in receptor-ligand (IL1Ra) HTRF ® binding assay

| Clone | $IC_{50}$ (nM) |
|---|---|
| Antibody 8GL IgG2 | 0.363 |
| Antibody 9GL IgG2 | 0.208 |
| Antibody 10GL IgG2 | 0.323 |
| AMG108 IgG2 | NI |
| DEI5-8 IgG4 | NI |
| Kineret | 0.323 |

$IC_{50}$ values represent geometric mean of three independent experiments
NI: No significant inhibition of IL1Ra was observed
GL: Germlined 2.6 Inhibition by Optimised IgG of huIL-1β-Induced IL-8 Release from CYNOM-K1 Cells In order to establish whether lead antibodies were as effective at inhibiting activity of IL-1β signalling through endogenously expressed cynomolgus IL-1R1, the ability of lead IgG to inhibit huIL-1β-induced IL-8 release from CYNOM-K1 cells was measured. Lead antibodies clearly and completely inhibited IL-1β acting through cynomolgus IL-1R1 with equal activity to IL-1Ra, whereas AMG108 IgG did not inhibit this interaction. A commercially available ELISA for human IL-8 was shown to also detect cynomolgus IL-8 in cell supernatants and was used to determine the IL-1-induced effect on CYNOM-K1 cells.

TABLE 8

Inhibition by optimised IgG of IL-1β induced IL-8 release from CYNOM-K1 cells expressing endogenous cynomolgus IL-1R

| Clone name | $IC_{50}$ (nM) (n = 2) |
|---|---|
| Antibody 6GL IgG2 | 0.8, 0.6 |
| Antibody 8GL IgG2 | 4.2, 2.5 |

TABLE 8-continued

Inhibition by optimised IgG of IL-1β induced IL-8 release
from CYNOM-K1 cells expressing endogenous cynomolgus IL-1R

| Clone name | IC$_{50}$ (nM) (n = 2) |
|---|---|
| Antibody 9GL IgG2 | 1.2, 1.1 |
| Antibody 10GL IgG2 | 0.9, 0.7 |
| AMG108 IgG2 | NI, NI |
| Isotype control IgG2 | NI, NI |
| Kineret | 0.2, 0.8 |

IC$_{50}$s reported are IC$_{50}$s from each of 2 independent experiments
NI = no inhibition of IL-1 beta induced IL-8 release observed 2.7 Inhibition of IL-1β induced IL-6 Production in Human Whole Blood Whole blood was collected from normal volunteers (6 donors) into sodium heparin monovette containers. Whole blood (80 μls) was aliquoted into wells of 96 well plates containing 10 μls of Anti-IL-1RI monoclonal Ab Antibody 6GL IgG2 in assay buffer (1% BSA in PBS), IL-1β was added 30 minutes later to give a final concentration of 30 pM (EC$_{50}$). The supernatants were harvested after 18 hours and IL-6 levels in the supernatant measured using an ELISA (R&D Systems IL-6 ELISA). The anti-IL-1RI antibody blocked IL-1 activity as shown in FIG. 13. The range of IC50 values for inhibition of IL-1 induced IL-6 production in human whole blood are shown in Table 9. The mean IC$_{50}$ for the 6 donors was 229 pM.

TABLE 9

IC$_{50}$ values for inhibition of IL-1β induced IL-6
production in human whole blood.

| Donor | 1 | 2 | 3 | 4 | 5 | 6 |
|---|---|---|---|---|---|---|
| IC$_{50}$ (pM) | 91 | 295 | 116 | 309 | 167 | 321 |

Equivalent data is provided in Example 4 for Antibody 6 with a different Fc format, Antibody 6 IgG1TM (Triple Mutant, 234F, 235E and 331S).

Assay Materials and Methods
Receptor-Ligand (IL1 Beta) Binding HTRF® Assay

Selection outputs were screened in receptor-ligand binding HTRF® (Homogeneous Time-Resolved Fluorescence, Cis-Bio, Bedford, Mass., USA) assay format for inhibition of HIS FLAG tagged human IL1 beta (In house, *E. coli* expressed; HIS FLAG IL-1 beta) binding to human histidine tagged (HIS) IL1RFc fusion protein (In house HEK EBNA expressed, as described below). More details of the HTRF® assay can be found in Mathis (1995) Clinical Chemistry 41(9), 1391-1397.

Outputs during lead isolation were screened as undiluted, crude scFv containing periplasmic extracts prepared in 200 mM HEPES buffer pH7.4, 0.5 mM EDTA and 0.5 M sucrose. 5 μl of crude scFv sample was added to a 384 well low volume assay plate (Costar 3676). This was then followed by addition of 2 nM human HIS IL1RFc to a volume of 20 μl. Assay plates were then sealed and incubated at room temperature in dark for 1 hour.

After pre-incubation of the assay plates, 5 μl of 4 nM HIS FLAG IL1 beta was added. This was followed by 5 μl of 20 nM anti-FLAG IgG labelled with XL665 (CIS Bio international 61FG2XLB) and 5 μl of 3.2 nM anti-human Fc IgG labelled with cryptate (CIS Bio International 61HFCKLB). All dilutions were performed in phosphate buffered saline (PBS) containing 0.4 M potassium fluoride and 0.1% BSA (assay buffer).

Assay plates were incubated for 3 h at room temperature in dark, prior to reading time resolved fluorescence at 620 nm and 665 nm emission wavelengths using an EnVision plate reader (Perkin Elmer).

Data were analysed by calculating % Delta F values and % specific binding for each sample according to equation 1 and equation 2 respectively.

Receptor-ligand assays were also performed using an alternative source of FLAG IL1 beta (Alexis, ALX-522-056) as follows. 5 μl of crude scFv containing periplasmic extracts prepared in 200 mM HEPES buffer pH7.4, 0.5 mM EDTA and 0.5 M sucrose was added to a 384 well low volume assay plate (Costar 3676). This was then followed by addition of 8 nM human HIS IL1RFc to a volume of 20 μl. Assay plates were then sealed and incubated at room temperature in dark for 1 hour.

After pre-incubation of the assay plates, 5 μl of 80 nM FLAG IL1 beta (Alexis ALX-522-056) was added. This was followed by 5 μl of 40 nM anti-FLAG IgG labelled with XL665 (CIS Bio international 61FG2XLB) and 5 μl of 3.2 nM anti-human Fc IgG labelled with cryptate (CIS BIO International 61HFCKLB). All dilutions were performed in phosphate buffered saline (PBS) containing 0.4 M potassium fluoride and 0.1% BSA (assay buffer).

Assay plates were incubated for 3 h at room temperature in dark, prior to reading time resolved fluorescence at 620 nm and 665 nm emission wavelengths using an EnVision plate reader (Perkin Elmer).

Data were analysed by calculating % Delta F values and % specific binding for each sample according to equation 1 and equation 2 respectively.

$$\% \text{ Delta } F = \frac{(\text{sample } 665/620 \text{ nM ratio value}) - (\text{non-specific control } 665/620 \text{ nM ratio value})}{(\text{non-specific control } 665/620 \text{ nM ratio value})} \times 100 \quad \text{Equation 1}$$

% Delta F values were subsequently used to calculate % specific binding as described in equation 2.

$$\% \text{ specific binding} = \frac{\% \text{ Delta } F \text{ of sample}}{\% \text{ Delta } F \text{ of total binding control}} \times 100 \quad \text{Equation 2}$$

Purified scFv from positive clones identified from screening were tested in either of the above receptor-ligand HTRF® assays for inhibition of binding of human HIS FLAG tagged IL1 beta to human HIS IL1RFc. A skilled person could modify these assays to test IgG or other inhibitor formats. A titration of scFv concentrations was used in order to establish the clone potency as measured by IC$_{50}$ values in the assay. All dilutions were carried out in assay buffer. 5 μl of a titration of purified scFv sample was added to a 384 well low volume assay plate (Costar 3676). This was then followed by addition of 2 nM human HIS IL1RFc (when using in house HIS IL1 beta) or 8 nM HIS IL1RFc (when using Alexis source IL1 beta) to a volume of 20 μl. Assay plates were then sealed and incubated at room temperature in dark for 1 hour. The subsequent addition steps were carried out as exactly as described for crude scFv containing periplasmic extracts.

Assay plates were incubated for 3 h at room temperature in dark, prior to reading time resolved fluorescence at 620 nm and 665 nm emission wavelengths using an EnVision plate reader (Perkin Elmer).

Data was analysed by calculating % Delta F values for each sample. Delta F and specific binding were determined according to equation 1 and equation 2 respectively. $IC_{50}$ values were determined using GraphPad Prism software by curve fitting using a four-parameter logistic equation (Equation 3).

$$Y=\text{Botton}-(\text{Top}-\text{Bottom})/(1\times10\char`\^((\text{Log } EC50-X)*\text{Hill-Slope}))$$ Equation 3

X is the logarithm of concentration. Y is specific binding Y starts at Bottom and goes to Top with a sigmoid shape.

A reference mouse anti-human IL1R1 mAb (Fitzgerald 10-173) and IL-1 receptor antagonist anakinra (Kineret®; AMGEN commercial pharmacy) were included in all purified scFv titration assays as positive controls.

For lead optimisation crude scFv were diluted in assay buffer. 5 µl of diluted crude scFv sample was added to a 384 well low volume assay plate (Costar 3676). This was then followed by addition of 2 nM human HIS IL RFc to a volume of 20 µl. Assay plates were then sealed and incubated at room temperature in dark for 1 hour.

After pre-incubation of the assay plates, 5 µl of 40 nM HIS FLAG IL1 beta (in-house E. coli expressed) was added. This was followed by 5 µl of 40 nM anti-FLAG IgG labelled with XL665 (CIS Bio international 61FG2XLB) and 5 µl of 3.2 nM anti-human Fc IgG labelled with cryptate (CIS BIO International 61HFCKLB). All dilutions were performed in phosphate buffered saline (PBS) containing 0.4 M potassium fluoride and 0.1% BSA (assay buffer).

Assay plates were incubated for 3 h at room temperature in dark, prior to reading time resolved fluorescence at 620 nm and 665 nm emission wavelengths using an EnVision plate reader (Perkin Elmer).

As for lead isolation, delta F and specific binding were calculated as described by equation 1 and equation 2 respectively.

Receptor-Ligand (IL1 Receptor Antagonist) Binding HTRF® Assay

Purified scFv from positive clones identified from screening were tested in receptor-ligand IL1 receptor antagonist (IL1ra) binding HTRF® assay. IgG were also tested in this assay format.

A titration of inhibitor was used in order to establish the clone potency as measured by $IC_{50}$ values in the assay. All dilutions were carried out in assay buffer as for ligand binding assay above. 5 µl of a titration of inhibitor was added to a 384 well low volume assay plate (Costar 3676). This was then followed by addition of 0.4 nM cryptate labelled HIS IL1RFc. Assay plates were then sealed and incubated at room temperature in dark for 1 hour.

After pre-incubation, 5 µl of 0.6 nM FLAG HIS IL1ra (In house E. coli expressed) was added. This was immediately followed by 5 µl of 40 nM anti-FLAG IgG labelled with XL665 (CIS BIO 61FG2XLB).

Assay plates were incubated for 3 h at room temperature in dark, prior to reading time resolved fluorescence at 620 nm and 665 nm emission wavelengths using an EnVision plate reader (Perkin Elmer).

Data was analysed by calculating % Delta F and % specific binding according to equation 1 and equation 2 respectively. $IC_{50}$ values were determined using GraphPad Prism software by curve fitting using a four-parameter logistic equation (Equation 3).

Selectivity and Species Cross Reactivity of Antibodies in Competition Binding Assays Purified IgG were adsorbed onto 96-well Maxisorp microtitre plates (Nunc) in PBS at a concentration which gave a significant signal when biotinylated human HIS IL1RFc was added at approximately its estimated $K_D$ for that particular IgG. Excess IgG was washed away with PBS-Tween (0.1% v/v) and the wells were blocked with non-fat dried milk in PBS (3% w/v) for 1 h. A dilution series of each of the following competitors was prepared in 3% non-fat dried milk, starting at a concentration of approximately 400-fold the $K_D$ value of the interaction between biotinylated human IL1RFc and the respective IgG: Cynomolgus monkey (Macaca fascicularis) HIS IL1RFc (in house HEK EBNA expressed, as described below), rat HIS IL1RFc (in house HEK EBNA expressed), recombinant human IL1 sRI (R&D systems 269-1R/CF), human IL-1R6/IL-1R rp2/Fc (R&D systems 872-RP), recombinant human IL-18 R alpha (IL-1 R5)/Fc (R&D systems 816-LR), recombinant human IL-1 R4 (ST2)/Fc (R&D systems 523-ST). Non-biotinylated human HIS IL1RFc was included as a positive control. 25 µl of this dilution series was added to the blocked IgG assay plate.

25 µl of 1.4 nM biotinylated human HIS IL1RFc was added to the assay plate. The plate was then sealed and incubated at room temperature for 2 h. Unbound antigen was removed by washing with PBS-Tween (0.1% v/v), while the remaining biotinylated human IL1RFc was detected by streptavidin-Europium3+ conjugate (DELFIA® detection, PerkinElmer). Time-resolved fluorescence was measured at 620 nm on an EnVision plate reader (PerkinElmer). Fluorescence data was plotted as europium counts. $IC_{50}$ values were determined using GraphPad Prism software by curve fitting using a four-parameter logistic equation (Equation 3).

Generation of Recombinant Human and Cynomolgus Monkey IL-1R1 Fc Fusion Proteins

A cDNA encoding the sequence of human IL-1R1 extracellular domain (amino acid residues 1-336 NP_000868) was amplified from human liver cDNA via PCR using primers based on the human IL-1R1 cDNA sequence (RefSeq NM_00877). A cDNA encoding cynomolgus monkey (Macaca fascicularis) IL-1R1 extracellular domain sequence (amino acid residues 1-336) was amplified from cynomolgus monkey liver cDNA using identical primers as used for the human PCR amplification. The cynomolgus monkey sequence was determined by analysis of PCR products using standard di-deoxy fluorescent terminator sequencing. The resultant DNA sequence is shown in FIG. 1 and the predicted amino acid sequence is shown FIG. 2. The resulting cDNAs were sub-cloned following the manufacturer's instructions into pENTR/D-TOPO (invitrogen).

The cDNA fragments coding the IL-1R1 extracellular domains were then transferred to mammalian expression vector pDEST12.2 (Invitrogen) using LR Gateway® reaction (Invitrogen). The pDEST12.2 vector had been modified to contain the human $IgG_1$ Fc coding region in-frame with the inserted gene of interest, and also by insertion of the oriP origin of replication from the pCEP4 vector (Invitrogen) allowing episomal plasmid replication upon transfection into cell lines expressing the EBNA-1 gene product (such as HEK293-EBNA cells). The resultant nucleotide and predicted amino acid sequences for the human IL-1R1Fc are shown in FIG. 3 and FIG. 4, and for cynomolgus monkey IL-1R1Fc in FIG. 5 and FIG. 6 respectively.

Protein was purified from conditioned media using Protein G chromatography followed by Size Exclusion chromatography.

Generation of Recombinant Human and Cynomolgus Rat IL-1R-Fc Fusion Proteins

Rat IL-1R-Fc was made by analogous methodology to the generation of recombinant human and cynomolgus monkey IL-1R1 Fc fusion proteins as described above.

HeLa IL-1α- and IL-1β-Induced IL-8 Release Assay

HeLa cells (European Collection of Cell Cultures, ECACC catalogue no. 93021013, a human negroid cervix epitheloid carcinoma cell line (Cancer Res 1952; 12:264; Proc Soc Exp Biol Med 1954; 87:480) maintained in MEM plus 10% fetal bovine serum plus 1% non-essential amino acids; cells were split between 1:4 and 1:12 from 100% confluency for routine culture) were seeded in 96-well flat-bottomed tissue culture assay plates (Costar) at $1.5 \times 10^4$ cells/well in 100 μl culture media volume/well (Dulbecco's Modified Eagle Medium (Invitrogen) with 10% (v/v) heat inactivated foetal bovine serum (Invitrogen), 1% (v/v) non-essential amino acids (Invitrogen)) and cells were then cultured overnight (16-18 h) in a humidified atmosphere at 37° C. and 5% $CO_2$.

A titration of purified scFv/IgG was prepared in culture media and 50 μl/well of this dilution series was added to the HeLa cells without removing overnight culture medium and pre-incubated with HeLa cells for 30-60 min at 37° C. This was followed by addition of 50 μl/well of ILα/IL-1β and incubation for 4-5 h in a humidified atmosphere at 37° C. and 5% $CO_2$. The concentration of the ligand used was $EC_{50}$ or above depending on the potency of the scFv/IgG being tested, where $EC_{50}$ is the concentration of ligand that produced half the maximum response to the ligand in this assay (calculated in a similar fashion to Equation 3.)

A reference mouse anti-human IL1R1 mAb (Fitzgerald 10-173) and IL-1 receptor antagonist anakinra (Kineret®; provided commercially from a pharmacy outlet) were included in titration assays as positive controls.

Supernatants (conditioned culture media) were harvested and stored at −20° C. until IL-8 analysis (usually less than 1 week).

IL-8 levels in supernatants were determined using human IL-8 Duoset ELISA kit (R & D Systems). IL-8 capture antibody (4 μg/ml diluted in PBS, 50 μl/well) was adsorbed to 96 well low auto-fluorescent, high protein binding plates (FluoroNunc Maxisorb plates) overnight at 4° C. Excess IgG was removed by washing with PBS-Tween and the wells were blocked with 1% bovine serum albumin (BSA) in PBS for 1 hour at room temperature, after which plates were washed as described previously. 80 μl of 0.1% bovine serum albumin (BSA) in PBS was added per well. 20 μl/well of conditioned culture media was then added to give 1:5 dilution of the conditioned culture media. IL-8 standards (from 1000 pg/ml, 1:2 dilution) were also added to ELISA plates as an ELISA control and the plates were incubated at room temperature for 2 hours.

Following incubation, plates were washed as before to remove unbound proteins. Biotinylated IL-8 detection Ab (20 ng/ml in reagent diluent (0.1% BSA/PBS); 50 μl/well) was then added to the plates and incubated at RT for 1 h. Unbound detection antibody was removed by washing with PBS-Tween (0.1% v/v), while the remaining biotinylated antibody was detected by streptavidin-Europium3+ conjugate (DELFIA® detection, PerkinElmer). Time-resolved fluorescence was measured at 615 nm on a Victor plate reader (PerkinElmner). Fluorescence data was plotted as europium counts.

Inhibitor data was normalized to percentage of maximal IL-8 release using the Europium counts from IL-1 stimulation in the absence of inhibitor control (max control) and no IL-1 control (media control) as Equation 4.

$IC_{50}$ values were determined using GraphPad Prism software by curve fitting using a four-parameter logistic equation (Equation 3).

CYNOMK1 IL-1β-Induced IL-8 Release Assay

CYNOM-K1 cells (cynomolgus-derived fibroblast cell line; European Collection of Cell Cultures, ECACC ref no 90071809; maintained according to suppliers instructions) were harvested using 0.25% trypsin/EDTA and seeded in 96-well flat-bottomed tissue culture assay plates (Costar) at $8 \times 10^3$ cells/well in 100 μl culture media volume/well (Minimum Essential medium MEM (invitrogen) with 20% (v/v) non-heat inactivated foetal bovine serum (Invitrogen), 1% (v/v) non-essential amino acids (Invitrogen)) and cells were then cultured overnight (16-18 hours) in a humidified atmosphere at 37° C. and 5% $CO_2$.

A titration of purified scFv/IgG was prepared in culture media and 50 μl/well of this dilution series was added to the CYNOM-K1 cells without removing overnight culture medium and pre-incubated with CYNOM-K1 cells for 30-60 min at 37° C. This was followed by addition of 50 μl/well of ILα/IL-1β and incubation for 4-5 hours in a humidified atmosphere at 37° C. and 5% $CO_2$. The concentration of the ligand used was $EC_{80}$, where $EC_{80}$ is the concentration of ligand that produced 80% of the maximum response to the ligand in this assay (calculated in a similar fashion to Equation 3.)

IL-1 receptor antagonist anakinra (Kineret®; provided commercially from a pharmacy outlet) was included in titration assays as a positive control.

Supernatants (conditioned culture media) were harvested and stored at −20° C. until IL-8 analysis (usually less than 1 week).

IL-8 levels in supernatants were determined using human IL-8 Duoset ELISA kit (R & D Systems). IL-8 capture antibody (4 μg/ml diluted in PBS, 50 μl/well) was adsorbed to 96 well low auto-fluorescent, high protein binding plates (FluoroNunc Maxisorb plates) overnight at 4° C. Excess IgG was removed by washing with PBS-Tween and the wells were blocked with 1% bovine serum albumin (BSA) in PBS for 1 h at room temperature, after which plates were washed as described previously. 80 μl of 0.1% bovine serum albumin (BSA) in PBS was added per well. 20 μl/well of conditioned culture media was then added to give 1:5 dilution of the conditioned culture media. IL-8 standards (from 1000 pg/ml, 1:2 dilution) were also added to ELISA plates as an ELISA control and the plates were incubated at RT for 2 hours.

Following incubation, plates were washed as before to remove unbound proteins. Biotinylated IL-8 detection Ab (20 ng/ml in reagent diluent (0.1% BSA/PBS); 50 μl/well) was then added to the plates and incubated at room temperature for 1 hour. Unbound detection antibody was removed by washing with PBS-Tween (0.1% v/v), while the remaining biotinylated antibody was detected by streptavidin-Europium3+ conjugate (DELFIA® detection, PerkinElmer). Time-resolved fluorescence was measured at 615 nm on a Victor plate reader (PerkinElmer). Fluorescence data was plotted as europium counts.

Inhibitor data was normalized to percentage of maximal IL-8 release using the Europium counts from IL-1 stimulation in the absence of inhibitor control (max control) and no IL-1 control (media control) as Equation 4.

$$\% \text{ max } IL\text{-}8 \text{ release} = \frac{(\text{Sample} - \text{media control})}{(\text{Max control} - \text{media control})} \times 100 \quad \text{Equation 4}$$

$$\% \text{ max } IL\text{-}8 \text{ release} = \frac{(\text{Sample} - \text{media control})}{(\text{Max control} - \text{media control})} \times 100 \quad \text{Equation 4}$$

IC$_{50}$ values were determined using GraphPad Prism software by curve fitting using a four-parameter logistic equation (Equation 3).

Cloning Human IL-1R1 Extracellular Domain

Sequence RefSeqNM 00877 was used as the reference sequence for human IL-1R1. The extracellular domain (residues 1-336) was amplified by PCR using human liver cDNA as a template. The primers used were NC268 (5'-CACCAT-GAAAGTGTTACTCAGAC) and NC269 (5'-CTTCTG-GAAATTAGTGACTGG). The amplified PCR product was cloned into pENTR-D-TOPO from Invitrogen using the manufacturer's instructions. Several clones were obtained and sequenced. Clone 4 was identical to the reference sequence and was kept for subsequent use.

The human polymorphism A124G was generated using standard site directed mutagenesis of the relevant GCA codon to GGA in human pENTR-D-topo IL-1R1 clone 4.

Cloning Cyno IL-1R1 Extracellular Domain

The sequence of the cynomolgus cDNA encoding IL-1R1 was available in the EMBL database (EMBL AY497008). This sequence was highly homologous to the human sequence, however it lacked the first 5' 27 bp of the coding sequence when compared to human IL-1R1. The cDNA encoding the soluble extracellular domain of cynomolgus monkey IL-1R1 (residues 1-336) was amplified by PCR using cynomolgus liver cDNA as a template. The primers used were NC268 as above which was the human IL-1R1 5'-primer, and NC270 (5'-CTTCTGGAATTTAGTGACTGG) as the reverse primer. The amplified PCR product was cloned into pENTR-D-TOPO from Invitrogen.

Several clones were sequenced and there were changes from the translated reference sequence used (EMBL AY497008).

The changes were
1. S17F: TCT in published sequence TTT in all clones (signal sequence)
2. V66I: GTA in published sequence ATA in all clones
3. H173N: CAC in published sequence and in clone5, AAC in all other clones In order to check the validity of these sequence changes compared to the published sequence the amplified cDNA encoding the extracellular domain was sequenced directly using standard di-deoxy fluorescent terminator sequencing. The S17F change was present in the amplified PCR product and appears to be a genuine change from the published sequence. The V66I change was also present in the amplified PCR product and appears to be a genuine change from the published sequence. The H173N change appears to be a genuine polymorphism as both a CAC and AAC codon was at present the same position at the same intensity. Direct sequencing of the PCR product identified a further polymorphism E300K. In this case, the sequencing reaction clearly showed equal amounts of the GAA and AAA codons.

Cloning Rat IL-1R1 Extracellular Domain

The sequence of rat cDNA encoding IL-1R1 was obtained from the EMBL database (EMBL ID RNIL1R) and used as a reference sequence. The extracellular domain (residues 1-336) was amplified by PCR using rat liver cDNA as a template. The primers used were NC288 (5'-CACCATGCT-GCCGAGGCTTG) and NC289 (5'-ATTCTTGAAGTCAG-GAACTGGGT). The amplified PCR product was cloned into pENTR-D-TOPO from Invitrogen using the manufacturer's instructions. Several clones were obtained and sequenced. Clone 1 was identical to the reference sequence and was kept for subsequent use.

Cloning Expression and Purification of Human HIS FLAG IL-1Ra

The sequence of human IL-1Ra was obtained from RefSeq database (NM_173842) and used as the reference sequence. The cDNA encoding the mature sequence of human IL-1Ra (residues 26-177) was amplified by PCR from human lung cDNA. The primers used were IL1RaF (5'-CCTCATATG-GAAAACCTGTACTTCCAGTCTCGAC-CCTCTGGGAGAAA) and IL1RaR (5'-ATATCTCGAGC-TACTCGTCCTCCTGGAAG). The design of primer IL1RaF was such that a Tobacco Etch Mosaic Virus protease (TEV) cleavage site was immediately adjacent to the N-terminal arginine residue of the mature IL-1Ra. The amplified PCR product was cloned into pCR4blunt-topo from invitrogen using the manufacturer's instructions.

Several clones were obtained and their sequences generated. A clone with the correct coding sequence compared to the reference sequence was chosen for further manipulation. The insert DNA was subsequently sub-cloned into a pT7 *E. coli* expression vector using the NdeI site in frame with an N-terminal (HIS)$_6$-FLAG tag.

To express soluble HIS-FLAG tagged protein, the expression plasmid was transformed into chemically competent BL21 (DE3) star cells from Invitrogen. Cells containing the expression plasmid were cultured in Lysogeny Broth (LB, which contains 10 g/liter tryptone, 5 g/liter yeast extract, 5 g/liter NaCl) at 37° C. to an OD600 of 0.5 IPTG was then added from a 1M stock to a final concentration of 50 µM. Cells were incubated at 37° C. for 3 hours. Cells were harvested by centrifugation at 6,000 rpm for 10 minutes and the pellets were stored at −80° C. The cells were thawed and resuspended in 50 mM Tris, pH18.0, 10% glycerol, 0.3M NaCl, 10 mM imidazole (buffer A) plus Complete protease inhibitors (Roche). The cells were lysed by sonication for 3×30 seconds on ice using a Heatsystems-Ultrasonics Inc. sonicator. The lysate was centrifuged at 100,000 g and 4° C. for 30 minutes. The supernatant was subjected to affinity chromatography using Ni-NTA Superflow (Qiagen). Bound material was eluted with buffer A containing 0.3M imidazole. Fractions containing IL-1Ra were pooled and buffer exchanged into PBS using a Hiprep 26/10 desalting column (GE Healthcare). The purity of the sample was tested using SDS-gel electrophoresis. The protein was analysed by gel filtration chromatography and found to be monomeric.

LPS was removed from 5 ml (14 mg) of the purified IL-1Ra using polymyxin B agarose (Sigma Prod. No. P1411). Sigma Polymyxin agarose were washed three times with LPS-free PBS (Sigma D8537) and applied to an empty BioRad Polyprep column and the beads were allowed to settle under gravity. The mil of packed beads were washed with 10 ml of LPS-free PBS. The IL-1ra sample was applied to the column and allowed to pass through the resin under gravity. The sample was passed through a further 1 ml polymyxin column. LPS levels in the IL-1Ra sample before and after polymyxin treatment were determined using a Pyrochrome LAL assay (Associates of Cape Cod Inc. C0180).

The molecular mass of the LPS—free protein was measured using intact mass analysis using Q-ToF mass spectroscopy. The measured mass was within 1 Da of the calculated mass (20325.67 Da) of the His-Flag-Tev-IL-1ra without the N-terminal Met.

Cloning, Expression and Purification of Human HIS FLAG-IL-1β

The sequence of human IL-1β was obtained from RefSeq database (NM_000576) and used as the reference sequence. The cDNA encoding the mature sequence of human IL-1β (residues 117-269) was amplified by PCR from human lung cDNA. The primers used were IL1bF (5'-CCTCATATG-GAAAACCTGTACTTCCAGTCTGCACCTG-TACGATCACTG) and IL1bR (5'-ATATCTCGAGTTAG-GAAGACACAAATTGCATGG). The design of primer IL1bF was such that a Tobacco Etch Mosaic Virus protease (TEV) cleavage site was immediately adjacent to the N-terminal alanine residue of the mature IL-1β. The amplified PCR product was cloned into pCR4blunt-topo from Invitrogen using the manufacturer's instructions. Several clones were obtained and their sequences generated. A clone with the correct coding sequence compared to the reference sequence was chosen for further manipulation. The insert DNA was subsequently sub-cloned into a pT7 *E. coli* expression vector using the NdeI site in frame with an N-terminal (HIS)$_6$-FLAG tag.

To express soluble HIS-FLAG tagged IL-1β protein, the expression plasmid was transformed into chemically competent BL21 (DE3) star cells from Invitrogen. Cells containing the expression plasmid were cultured in LB at 37 C to an OD600 of 0.5. IPTG was then added from a 1M stock to a final concentration of 50 µM. Cells were incubated at 37° C. for a further 3 hours. Cells were harvested by centrifugation at 6,000 rpm for 10 minutes and the pellets were stored at −80° C. The cells were thawed and resuspended in 50 mM Tris, pH8.0, 10% glycerol, 0.3M NaCl, 10 mM imidazole (buffer A) plus Complete™ protease inhibitors (Roche). The cells were lysed by sonication for 3×30 seconds on ice using a Heatsystems-Ultrasonics Inc. sonicator. The lysate was centrifuged at 100,000 g and 4° C. for 30 minutes. The supernatant was subjected to affinity chromatography using Ni-NTA Superflow (Qiagen). Bound material was eluted with buffer A containing 0.3M imidazole. Fractions containing IL-1β were pooled and buffer exchanged into PBS using a Hiprep 26/10 desalting column (GE Healthcare). The purity of the sample was tested using SDS-gel electrophoresis. The protein was analysed by gel filtration chromatography and found to be monomeric.

LPS was removed from the purified IL-1β in essentially the same way as described above using polymyxin B agarose (Sigma Prod. No. P1411).

The molecular mass of the LPS-free IL-1β protein was measured using intact mass analysis using Q-ToF mass spectroscopy. The measured mass was within 1 Da of the calculated mass (20576.10 Da) of the His-Flag-Tev-IL-1β without the N-terminal Met Example 3

Affinity Measurements of Antibody 6 and AMG108

The affinity of the antibodies to IL-1R1 of the invention were measured in two ways, both using KinExA™. technology (118). KinExA™. (Kinetic Exclusion Assay) is a flow spectrofluorometric based technology that can be used to accurately quantify high affinity interactions, including those in the sub-picomolar range (119).

Firstly either a monomerised FAb was allowed to come to equilibrium with sIL-1R1-Fc (soluble sIL-1R1-Fc), or the IgG was allowed to come to equilibrium with sIL-1R1 (untagged). These equilibrated solutions of the interacting molecules were then analysed using KinExA™. 3200 technology. In brief, for each equilibrated sample, the KinExA™. 3200 instrument automatically packed a fresh column of sIL-1R1 conjugated micro-beads. The sample containing antibody (or FAb fragment), antigen, and Ab/antigen (or FAb/antigen) complex (in Dulbecco's PBS, 1 mg mL$^{-1}$ bovine serum albumin, 0.02% (w/v) sodium azide) was flowed rapidly (0.25 mL/min) through the column to keep the contact time of the sample with the antigen-beads extremely brief. This rapid contact time ensured that, for high affinity (slowly dissociating) interactions, dissociation of the complex was negligible during this short contact time. Free antibody bound to the IL-1R1-beads. A Cy5™ (cyanine) fluorescently labelled secondary antibody, mouse anti-human IgG (heavy and light chain specific) was then passed through the column. Labelled secondary antibody bound to the antibody bound to the column. A buffer wash removed excess label, leaving fluorescence signal on the bead column directly proportional to the amount of free receptor in the original sample. By making a titration of a range of different concentrations of antibody and sIL-1R1, and measuring free antibody after each of these conditions, a $K_D$ was estimated for the antibody to the receptor (least squares fitting, using a 1:1 reversible bimolecular interaction model within the supplied KinExA™. Pro software). Although affinity estimates using BIAcore technology (Surface Plasmon Resonance) were comparable, the extremely slow dissociation rates means that the KinExA™. evaluation gives a more reliable measure of affinity at $K_D$ values <10 pM.

The results of affinity measurements for an anti-IL-1R1FAb to soluble human IL-1R1 and soluble cynomolgus IL-1R1 is given in Table 10 below. The results show that this antibody bound to human and cynomolgus IL-1R1 with equally high affinity, and despite being on an epitope where competition with IL-1-alpha, -beta and IL-1 receptor antagonist (IL-1ra) were all possible, the affinity for the receptor is very high. The affinity to human sIL-1R1 was compared for an example antibody as an IgG1TM format to AMG108 IgG2. AMG108 IgG2 does not bind to cynomolgus IL-1R1-Fc, and AMG108 being an IgG2 does not readily form monomeric stable homogeneous FAb fragments. Thus only a comparison between whole IgGs was possible. The results in Table 11, demonstrate that affinity to the human sIL-1R1 was comparable between the example antibody and AMG108. In a previous publication (International Patent Application No: WO 2004/022718) there were disclosed antibodies which competed with IL-1ra, however, these (designated the second class of antibodies identified) were of lower affinity and potency. In contrast, here we demonstrate an antibody that competes for IL-1ra yet has a very high affinity to IL-1R1. The results for the FAb and IgG1TM for Antibody 6 were similar.

TABLE 10

| Antibody | KD Human IL1-R1-Fc | KD CynoIL1-R1-Fc |
|---|---|---|
| Antibody 6 FAb | 2.5 pM | 2.8 pM |

TABLE 11

| Antibody | KD Human sIL-1R1 |
|---|---|
| Antibody 6 IgG1TM | 3.05 pM |
| AMG108 IgG2 | 4.12 pM |

Methods:
FAb Monomerisation

Antibody 6 IgG1TM (Triple Mutant, 234F, 235E and 331S) was digested in solution using activated papain. Papain (SIGMA) (6.2 mgs) was activated by dissolving in 620 µl Dulbeccos PBS (D-PBS) and incubating with 62 µl 100 mM L-Cys in D-PBS followed by 10 µl 1M NaHCO$_3$ in D-PBS. The solution was then desalted on a D-PBS equilibrated Sephadex G25 (PD-10) column and the 2.75-3.85 ml fraction collected. This cleared unwanted residual L-Cys and inhibitory low molecular weight papain autolysis products. 250 µl Antibody 6 IgG1TM (9.32 mgml$^{-1}$) with 25 µl NaHCO$_3$ in D-PBS (to increase pH to 8-8.5) and 50 µl L-Cys activated papain PD-10 eluate (as described above) were mixed and the reaction incubated at RT. Reaction progress was followed by injecting 50 µl samples onto a Superdex 75 size exclusion chromatography column that had been equilibrated with D-PBS at 0.5 mL min$^{-1}$. All of the remaining digest was added to 0.43 g (damp weight) Protein C Sepharose 4 Fast Flow. The peak corresponding to monomeric FAb fragment was collected and concentrated to 105 µl using an Amicon Ultra 4 10,000 MWCO centrifugal concentrator (Millipore, Billerica, Mass., USA). This was then re-injected onto a Superdex 75 column, and the peak corresponding to FAb fraction was collected. The 21.0-21.8 minute fraction from the final Superdex 75 purification step was used as a source of pure Antibody 6 FAb. The FAb was reanalyzed on a Superdex 75 column after 3 days storage at 4° C. and <0.4% multimer was measured, demonstrating that the monomeric FAb preparation was sufficiently stable for the affinity analysis. The purity of the monomeric FAb was also confirmed using reducing and non-reducing SDS-PAGE and reducing and non-reducing MALDI-TOF Mass Spectrometric analyses. KinExA™. Analysis IL-1R-Fcs, either human (SEQ ID NO: 134; expected peptide sequence based mass of 65,036.92 Da as fully reduced monomer; 133,039.8 Da as the –Fc dimer; 11,071 nM as monomer concentration) or cynomologous monkey (SEQ ID NO: 136; expected peptide sequence based mass of 65213.14 Da fully reduced, Swiss Prot, 130,392.3 Da as –Fc Dimer 7,974 nM as monomer concentration) were used as antigen for affinity measurements with Antibody 6 FAb (direct comparison of affinities with Human and cyno IL-1Rs). Human s IL-1R1 (R&D Systems, expected peptide sequence based mass of 49,503 Da) was used as antigen in the experiments to measure the affinities of AMG108 and Antibody 6 as IgGs (for direct comparison of the affinities of AMG108 and Antibody 6 IgGs).

Due to the long equilibration times, all buffers used in the KinExA™. experiments were 0.2 µm filter sterilised. For the column (common to both FAb and IgG based measurements) human IL-1R1 (R&D Systems) was used, and covalently bound to 100 mgs (1 µg IL-1R1 per mg beads) of azlactone UltraLink Biosupport beads (Thermo Fisher Scientific, Rockford, Ill., USA)) in 3 mls 50 mM sodium carbonate pH=8.4 at room temperature with constant agitation for 50 mins. Rinsing and blocking was achieved with 10 mgml$^{-1}$ BSA in 1M Tris pH18.7 (a single rinse of 1 ml, following centrifugation of the beads, and 2 ml with 25 r.p.m. agitation for 1.5 hrs at RT after a second centrifugation). Sedimented beads were finally transferred one more time into 2 mls fresh BSA buffer and stored at 4° C. until used. Finally this bead suspension, was added to 60 mls D-PBS+0.02% sodium azide, and connected onto the instrument bead handling system. Mouse anti-human IgG (H+L) Cy5 conjugate was made up at 1.4 mgml$^{-1}$ in 0.01M Na Phosphate, 0.25M NaCl (pH7.6) with 15 mgml$^{-1}$ BSA and 0.05% Na Azide. This was held at 4° C. until needed. FAbs and IgGs were diluted to 50 nM or 250 pM or 100 pM or 10 pM. FcRs were diluted in 2-fold dilution series incorporating Antibody 6 FAb or Antibody 6 Ab/AMG108Ab with a dilution series from 25 or 5 nM to 0.1525 pM (in Dulbecco's PBS, 1 mg mL$^{-1}$ bovine serum albumin, 0.02% (w/v) sodium azide). Complexes were allowed to come to equilibrium at 18° C. (room temperature) for 12-16 days, and then were flowed through the column following signal testing. Bound free antibody was detected using 50 µl Cy5 labelled secondary antibody. Data processing and analysis was performed using KinExA™. Pro (v 2.0.0, 17) software.

Example 4

Whole Blood Assay

Antibodies were analysed for potency in a whole blood assay, where IL-1beta (GIBCO, lyophilised, carrier free) incubation results in release of IL-6. In brief, antibodies were diluted to 15 µg/ml in PBS containing 1% BSA and then serially titrated in 1:3 dilutions in PBS/1% BSA. 10 µl of each concentration of antibody, or a PBS/1% BSA control was incubated with 80 ul of whole human blood for 30 mins at room temperature. 10 µl IL-1beta in PBS/1% BSA or PBS/BSA alone was added to give a final assay concentration of 30 pM and incubated for 22±2 hrs at 37° C. in a humidified 5% $CO_2$ incubator. 100 µl PBS was added to the wells and after spinning at 300 g for 10 minutes the supernatant was removed and analysed for IL-6 content using a commercially available huIL-6 ELISA kit (R&D Systems Duoset, as instructions).

The potency of Antibody 6 IgG1TM in this assay was 311 pM (83 pM-1.2 nM) (Mean $IC_{50}$; 95% CI).

Example 5

Epitope Mapping of Antibody 6 Interaction Using Chimeric Human/Mouse IL-1R1 Extracellular Domains 5.1 Generation of Whole Domain Swap Chimeric IL-1R1 Molecules.

Antibody 6 binds human IL-1R1 but not mouse IL-1R1. Using this property, chimeric IL-1R1 molecules were generated for epitope mapping. Whole domain-swap chimeras were created by replacing domain 1 (D1) (M1-Y122), domain 2 (D2) (N123-V227) or domain 3 (D3) (I228-K336) of human IL-1R1 ectodomain with corresponding mouse IL-1R1 sequence. Sub-domain swap chimeras were generated by replacing regions known to interact with IL1β [120] and IL1ra [121] from human IL-1R1 with corresponding regions from mouse IL-1R1. An HTRF (homogeneous time resolved fluorescence) competition assay was used to determine chimeras binding to antibody. In the assay antibody labelled with $Eu^{3+}$ cryptate interacted with Human IL-1R1 labelled with biotin. The interaction was detected by a FRET (Fluorescence Resonance Energy Transfer) signal between $Eu^{3+}$ cryptate and $XL^{ent!}$ labelled streptavidin [122].

5.1.1 Materials and Methods—Cloning, Expression and Purification of Chimeras cDNA molecules encoding chimeras of human IL-1R1 extracellular domain (amino acid residues 1-336 NP_000868) and mouse IL-1R1 extracellular domain (amino acid residues 1-338 NP_032388) were synthesised by primer extension PCR cloning and cloned into pDONR221 (Invitrogen Cat. No. 12536-017). The cDNA fragments coding for the IL-1R1 extracellular domain chimeras were then transferred to mammalian expression vector pDEST12.2 (Invitrogen) using LR Gateway Clonase II enzyme according to the manufacturer's instructions (Invitrogen Cat. No. 12538-120). The pDEST12.2 vector had been modified to contain a Human IgG1 Fc fragment and 6xhis tag (SEQ ID NO: 134) in-frame with the inserted gene of interest, and also by insertion of the oriP origin of replication from the pCEP4 vector (Invitrogen cat. no. V044-50) allowing episomal plasmid replication upon transfection into cell lines expressing the EBNA-1 gene product (such as CHO cells transfected with the EBNA-1 gene [CHO-EBNA]). Expressed protein in the supernatant from CHO-EBNA gene was purified using Protein G affinity chromatography (Hi-Trap Protein G HP column (GE Healthcare Cat. No. 17-0404-03)) followed by Size Exclusion chromatography (Superdex 200 column (GE Healthcare Cat. No. 17-1069-01)).

The sequence of human IL-1R1 extracellular domain (amino acid residues 1-336 NP_000868), vector encoded sequence, human IgG1 Fc tag and 6xhis tag is disclosed in SEQ ID NO: 134. The sequence of mouse IL-1R1 extracellular domain (amino acid residues 1-338 NP_032388), vector encoded sequence.

5.1.2 Binding of Antibody to IL-1R1 Chimeras

Antibody was cryptate labelled with $Eu^{3+}$ Cryptate labelling kit according to the manufacturer's instructions (CisBio International Cat No. 62EUSPEA) and IL-1R1/Fc (SEQ ID NO: 134, see Material and Methods) was Biotin labelled with EZ Link Sulfo-NHS-Biotin (Perbio Cat No. 21335) according to the manufacturer's instructions. Assay conditions were 0.25 nM Cryptate labelled antibody, 0.3 nM biotin labelled IL-1R1/Fc, 2.5 nM streptavidin $XL^{ent!}$ (CisBio International Cat. No. 611SAXLB) in 1×D-PBS, 0.1% BSA, 0.4M potassium fluoride in a total volume of 20 µl in a 384 well shallow well costar plate (3676). To the assay a dilution series (from maximum of 100 nM to 0.0017 nM) of test proteins was added and the assay incubated for 3 hours at room temperature. FRET signal was detected using a PerkinElmer EnVision plate reader using a 320 nm excitation filter and 620 nm and 665 nm emission filters. Results were calculated from the 665/620 ratio as a percentage of specific binding (signal with no competitor antigen). Results were analysed with Prism (GraphPad Software) using the sigmoidal dose response model.

5.2 Results

Antibody binding of chimeric molecules was tested in an HTRF (Homogeneous Time Resolved Fluorescence) competition assay. Molecules which bound antibody at the same paratope as human IL-1R1 inhibited the binding interaction, leading to a reduction in signal. From inhibition curves $IC_{50}$ values for human IL-1R1, mouse IL-1R1 and chimeric molecules were calculated (Table 12). If a molecule did not fully inhibit binding the percentage inhibition seen at the highest concentration was calculated. Chimeras that gave similar $IC_{50}$ values to native human IL-1R1 still contained the epitope. Chimeras which did not fully inhibit IL-1R1 binding to antibody, or showed an increased $IC_{50}$ value, did not contain the full epitope. These data enabled the localisation of the antibody epitope.

TABLE 12

$IC_{50}$ (in nM) of chimeric IL-1R1 molecules competing against human IL-1R1 binding to antibody. Chimeras composed of amino acid sequence from human (NP_000868) and mouse (NP_032388) IL-1R1 were tested for the ability to compete with human IL-1R1 in binding antibody. $IC_{50}$ values were calculated where a complete competition curve was obtained.

| Chimera | Sequence from NP_000868 | Sequence from NP_032388 | $IC_{50}$ (nM) in competition assay |
|---|---|---|---|
| HuIL-1R1 | M1-K336 | | 0.174 |
| MoIL-1R1 | | M1-K338 | 66% Inhibition* |
| MoD1-D2 HuD3 IL1R1 | M1-S17; I228-K336 | L20-V230 | 53% Inhibition* |
| MoD2 HuD1HuD3 IL1R1 | M1-Y122; I228-K336 | S126-V230 | 37% Inhibition* |
| MoD3 HuD1-D2 IL1R1 | M1-V227 | I231-K338 | 0.147 |
| MoD2-D3 HuD1 IL1R1 | M1-Y122 | S126-K338 | 18% Inhibition* |
| MoD1b IL1R1 | M1-R42; T54-K336 | K45-D56 | 0.201 |
| MoD2a IL1R1 | M1-Y122; A135-K336 | S126-I137 | 4.6 |
| MoD2b IL1R1 | M1-G139; L158-K336 | D140-E160 | 0.583 |
| MoD2c IL1R1 | M1-V177; L181-K336 | K181-K183 | 0.637 |
| MoD2d IL1R1 | M1-I213; I234-K336 | T220-V230 | 0.204 |
| MoD3a1 IL1R1 | M1-V246; V278-K336 | T254-P275 | 0.156 |
| MoD3a2 IL1R1 | M1-P272; S290-K336 | F276-K292 | 0.268 |
| MoD3b IL1R1 | M1-P309; Y329-K336 | F313-I331 | 0.337 |

*Where the chimera failed to completely inhibit human IL-1R1 binding to antibody the percentage inhibition seen at the highest concentration of chimera is shown.

The binding of chimeric human/mouse IL-1R1 chimeras has enabled the localisation of the human IL-1R1 epitope bound by antibody. Whole domain swap chimeras localised the epitope to D2 of human IL-1R1 (residues N123-V227) as all chimeras that contain the mouse D2 domain of IL1R1 replacing the human D2 IL1R1 (MoIL-1R1; MoD1-D2 HuD3 IL1R1; MoD2 HuD1 HuD3 IL1R1; MoD2-D3 HuD1) failed to completely inhibit Human IL1R1, whereas those containing D2 Human IL1R1 (HuIL-1R1; MoD3 HuD1-D2) were able to compete with human IL-1R1 (Table 12).

Human IL-1R1 contains 7 beta strands and 4 loop regions, spread across the three domains which are in close proximity to IL1β in a crystal structure [123]. Also the human IL1R1 contains 3 beta strands and 7 loop regions that are in close proximity to IL1 ra in a crystal structure (Schreuder et al., Nature 386:194-200, 1997). Beta strand or loop swap chimeras enabled the localisation of the human IL-1R1 epitope to a major component in domain 2 including beta strand a2 (residues N123-V134) and minor components in loop b2-c2 (residues L140-K157) (Vigers et al., Nature 386:190-194, 1997) and loop d2-e2 (residues K178-R180) (Schreuder et al., Nature 386:194-200, 1997). Chimeras without human beta strand a2 gave a 26 fold higher $IC_{50}$ than human IL1R1 binding to antibody and chimeras without loop b2-c2 or d2-e2 gave a >3 fold higher $IC_{50}$ than human IL-1R1 (Table x). Consistent with the domain swap data the beta strand a2, loops b2-c2 and d2-e2 are located in domain 2 (Vigers et al., Nature 386:190-194, 1997).

From these data the antibody binds amino acids in a discontinuous epitope of 33 amino acids in three regions of human IL-1R1; N123-V134, L140-K157 and K178-R180.

Biological Deposits Biological deposits in *E. coli* TOP10 have been made at:
NCIMB Limited
Ferguson Building,
Craibstone Estate,
Bucksburn,
Aberdeen,
AB21 9YA.
Scotland
UK
under the Budapest Treaty.

|  | Depositer's Strain Designation | Vector size (bps) | Insert Size | Deposit Date | Accession Number |
|---|---|---|---|---|---|
| Antibody 6 VH GL | 28PL GL VH | 2965 | 385 | 3 Nov. 2009 | NCIMB 41673 |
| Antibody 6 VL GL | 28PL GL VL | 2921 | 341 | 3 Nov. 2009 | NCIMB 41674 |
| Antibody 9 VH GL | 28Q1 GL VH | 2968 | 388 | 3 Nov. 2009 | NCIMB 41671 |
| Antibody 9 VL GL | 28Q1 GL VL | 2927 | 347 | 3 Nov. 2009 | NCIMB 41672 |

Said deposits represent another embodiment of the invention.

REFERENCES

All references cited anywhere in this specification, including those cited anywhere above, are incorporated herein by reference in their entirety and for all purposes.

1 Dinarello C A (2002) Clin Exp Rhematol 20 (5) S27, S1-S13
2 Dunn et al. (2001) Trends Immunol 22(10) 533-6
3 Schmitz et al (2005) Immunity 23, 279-90
4 Patterson D et al (1993) Genomics 15(1), 173-6
5 Steinkasserer A et al (1992) Genomics 13(3), 654-7
6 Black R A et al (1988) J Biol Chem 263(19), 9437-42
7 Niki Y et al (2004) J Immunol 172(1) 577-84
8 Wessendorf J H et al (1993) J Biol Chem 268(29) 22100-4
9 Carter D B et al (1990) Nature 344 (6267) 633-8
10 Eisenberg S P et al (1990) Nature 343 (6256) 341-6
11 Dewberry R et al (2000) Arterioscler Thromb Vase Biol 20 (11) 2394-400
12 Muzio M et al (1995) J Exp Med 182 (2) 623-8
13 Gabay C et al (1997) J Immunol 159 (12) 5905-13
14 Sims J E (2002) Current Opinion in Immunology 14, 117-122
15 Sims J E et al (1994) Clin Immunol Immunopathol 72 (1) 9-14
16 Colotta F et al (1994) Immunol Today 15 (12) 562-6
17 Vigers G P et al (1997) Nature 386 (6621) 190-4
18 Schreuder H et al (1997) Nature 386 (6621) 194-200
19 Boraschi D et al (1995) J Immunol 155 (10) 4719-25
20 Casadio R et al (2001) FEBS Lett 499 (1-2) 65-8
21 D'Ettorre C et al (1997) Eur Cyt Netw 8 (2) 161-71
22 Greenfeder S A et al (1995) J Biol Chem 270 (23) 13757-65
23 Hanmum et al (1990) Nature 343, 336-340
24 Lang D et al (1998) J Immunol 161 6871-77
25 Re et al (1996) J Exp Med 183, 1841-1850
26 Jiang Z et al (2002) Molecular and Cellular Biology 22 (20) 7158-7167
27 Osborn O et al (2008) Cytokine 44(1):141-8, 2008
28 Sauter et al (2008) Endocrinology 149: 2208-2218
29 Larsen et al (2007) N Engl J Med 356:1517-1526
30 Wanderer (2008) Clinical Immunology 128:127-132
31 Ikonomidis et al (2008) Circulation 117:2662-2669
32 Dinarello C A (1996) Blood 87 (6) 2095-147
33 Mizel et al 1987 J Immunol 138, 2906-2912
34 Qwarnstrorm et al 1988 J Biol Chem 263, 8261-8269
35 Dripps et al 1991 J Biol Chem 266, 10331-10336
36 Kabat, E. A. et al, Sequences of Proteins of Immunological Interest. 4$^{th}$ Edition. US Department of Health and Human Services. 1987
37 Altsclul et al. (1990) J. Mol. Biol. 215: 405-410
38 Pearson and Lipman (1988) PNAS USA 85: 2444-2448
39 Smith and Waterman (1981) J. Mol Biol. 147: 195-197
40 Voet & Voet, *Biochemistry,* 2nd Edition, (Wiley) 1995.
41 Gram et al., 1992, *Proc. Natl. Acad. Sc., USA.* 89:3576-3580
42 Barbas et al., 1994, *Proc. Natl. Acad. Sci., USA.* 91:3809-3813
43 Schier et al., 1996, *J. Mol. Biol.* 263:551-567
44 Holliger & Hudson (2005) Nature Biotechnology 23(9): 1126-1136
45 Ward, E. S. et al., Nature 341, 544-546 (1989)
46 McCafferty et al (1990) Nature, 348, 552-554
47 Holt et al (2003) Trends in Biotechnology 21, 484-490
48 Bird et al, Science, 242, 423-426, 1988
49 Huston et al, PNAS USA, 85, 5879-5883, 1988
50 Holliger, P. et al, Proc. Natl. Acad. Sci. USA 90 6444-6448, 1993
51 Reiter, Y. et al, Nature Biotech, 14, 1239-1245, 1996
52 Hu, S. et al, Cancer Res., 56, 3055-3061, 1996
53 Holliger and Bohlen 1999 Cancer and metastasis rev. 18: 411-419
54 Holliger, P. and Winter G. Current Opinion Biotechnol 4, 446-449 1993
55 Glennie M J et al., 1987 J. Immunol. 139, 2367-2375
56 Repp R. et al., 1995 J. Hermat. 377-382
57 Staerz U. D. and Bevan M. J. 1986 PNAS 83
58 Suresh M. R. et al., 1986 Method Enzymol. 121: 210-228
59 Merchand et al., 1998 Nature Biotech. 16:677-681
60 Ridgeway, J. B. B. et al, Protein Eng., 9, 616-621, 1996
61 Haan & Maggos (2004) BioCentury, 12(5): A1-A6
62 Koide et al. (1998) Journal of Molecular Biology, 284: 1141-1151.
63 Nygren et al. (1997) Current Opinion in Structural Biology, 7: 463-469
64 Wess, L. In: BioCentury, The Bernstein Report on Bio-Business, 12(42), A1-A7, 2004
65 Robinson, J. R. ed., Sustained and Controlled Release Drug Delivery Systems, Marcel Dekker, Inc., New York, 1978
66 Ledermann J. A. et al. (1991) Int. J. Cancer 47: 659-664
67 Bagshawe K. D. et al. (1991) Antibody, Immunoconjugates and Radiopharmaceuticals 4: 915-922
68 Hunter W. M. and Greenwood F. C. (1962) Nature 194:495
69 Plückthun, A. Bio/Technology 9: 545-551 (1991)
70 Chadd H E and Chamow S M (2001) Current Opinion in Biotechnology 12: 188-194
71 Andersen D C and Krummen L (2002) Current Opinion in Biotechnology 13: 117

72 Larrick J W and Thomas D W (2001) Current Opinion in Biotechnology 12:411-418
73 Sambrook and Russell, *Molecular Cloning: a Laboratory Manual:* 3rd edition, 2001, Cold Spring Harbor Laboratory Press
74 Ausubel et al. eds., *Short Protocols in Molecular Biology: A Compendium of Methods from Current Protocols in Molecular Biology*, John Wiley & Sons, 4th edition 1999
75 Harlow and Lane, Antibodies: A Laboratory Manual, Cold Spring Harbor Laboratory, Cold Spring Harbor N.Y., pp. 726, 1988
76 Köhler and Milstein, Nature, 256:495-497, 1975
77 Kontermann, R & Dubel, S, *Antibody Engineering*, Springer-Verlag New York, LLC; 2001, ISBN: 3540413545
78 Mendez, M. et al. (1997) Nature Genet, 15(2): 146-156
79 Knappik et al. J. Mol. Biol. (2000) 296, 57-86
80 Krebs et al. Journal of Immunological Methods 254 2001 67—-84
81 Wold, et al. Multivariate data analysis in chemistry. Chemometrics—Mathematics and Statistics in Chemistry (Ed.: B. Kowalski), D. Reidel Publishing Company, Dordrecht, Holland, 1984 (ISBN 90-277-1846-6)
82 Norman et al. Applied Regression Analysis. Wiley-Interscience; 3rd edition (April 1998) ISBN: 0471170828
83 Kandel, Abraham & Backer, Eric. Computer-Assisted Reasoning in Cluster Analysis. Prentice Hall PTR, (May 11, 1995), ISBN: 0133418847
84 Krzanowski, Wojtek. Principles of Multivariate Analysis: A User's Perspective (Oxford Statistical Science Series, No 22 (Paper)). Oxford University Press; (December 2000), ISBN: 0198507089
85 Witten, Ian H. & Frank, Eibe. Data Mining: Practical Machine Learning Tools and Techniques with Java Implementations. Morgan Kaufmann; (Oct. 11, 1999), ISBN: 1558605525
86 Denison David G. T. (Editor), Christopher C. Holmes, Bani K. Mallick, Adrian F. M. Smith. Bayesian Methods for Nonlinear Classification and Regression (Wiley Series in Probability and Statistics). John Wiley & Sons; (July 2002), ISBN: 0471490369
87 Ghose, Amrp K. & Viswanadhan, Vellarkad N. Combinatorial Library Design and Evaluation Principles, Software, Tools, and Applications in Drug Discovery. ISBN: 0-8247-0487-8
88 Chothia C. et al. Journal Molecular Biology (1992) 227, 799-817
89 Al-Lazikani, et al. Journal Molecular Biology (1997) 273 (4), 927-948
90 Chothia, et al. Science, 223, 755-758 (1986)
91 Whitelegg, N. R. u. and Rees, A. R (2000). Prot. Eng., 12, 815-824
92 Guex, N. and Peitsch, M. C. Electrophoresis (1997) 18, 2714-2723
93 Marks et al *Bio/Technology*, 1992, 10:779-783
94 Kay, B. K., Winter, J., and McCafferty, J. (1996) Phage Display of Peptides and Proteins: A Laboratory Manual, San Diego: Academic Press
95 Kabat, E. A. et al. (1991) Sequences of Proteins of immunological Interest, 5th Edition. US Department of Health and Human Services, Public Service, NIH, Washington
96 Segal et al., PNAS, 71:4298-4302, 1974
97 Amit et al., Science, 233:747-753, 1986
98 Chothia et al., J. Mol. Biol., 196:901-917, 1987
99 Chothia et al., Nature, 342:877-883, 1989
100 Caton et al., J. Immunol., 144:1965-1968, 1990
101 Sharon et al., PNAS, 87:4814-4817, 1990
102 Sharon et al., J. Immunol., 144:4863-4869, 1990
103 Kabat et al., J. Immunol., 147:1709-1719, 1991
104 Vaughan, T. J., et al. (1996). *Nature Biotechnology* 14, 309-314.
105 Hutchings, C. Generation of Naïve Human Antibody Libraries, in Antibody Engineering, R. Kontermann and S. Dubel, Editors. 2001, Springer Laboratory Manuals, Berlin. p. 93
106 Vaughan, T J. et al. Nature Biotechnology 14(3):309-14, 1996
107 Hutchings, C. Generation of Naïve Human Antibody Libraries, in Antibody Engineering, R. Kontermann and S. Dubel, Editors. 2001, Springer Laboratory Manuals, Berlin. p. 93
108 Thompson, J. et al. J Mol. Biol. 256(1):77-88, 1996
109 Osbourn, J K. et al. Immunotechnology, 2(3):181-96, 1996
110 Bannister, D. et al. Biotechnology and Bioengineering. 94(5):931-7, 2006.
111 Persic, L. et al. Gene. 187(1):9-18, 1997
112 Mach et al. Anal. Biochem. 200(1): 20-26, 1992
113 Tomilinson 1 (1997) V base, The Database of human antibody genes. (http://vbase.mrc-cpe.cam.ac.uk)
114 Foote J and Winter G (1992) J Mol Biol 224 (2) 487-99
115 Clackson, T. and Lowman, H. B. Phage Display—A Practical Approach, 2004. Oxford University Press
116 Groves, M. A. T and Osbourn, J. K. (2005) Expert opin. Biol. Ther. 5(1):125-135
117 Groves, M. et al. (2006). Journal of Imm. Methods 313 (129-139)
118 Darling, R. J. and Brault P-A, 2004, Kinetic Exclusion Assay Technology: Characterization of Molecular Interactions. Assay and Drug Development Technologies, Volume 2, no. 6, 647-657
119 Rathanaswami, P., Roalstad, S., Roskos, L, Qiaojuan, J. S., Lackie, S and Babcook, J., 2005, Demonstration of an in vivo generated sub-picomolar affinity fully human monoclonal antibody to interleukin-8, Biochemical and Biophysical Research Communications, 334, 1004-1013
120 Vigers et al., Nature 386:190-194, 1997
121 Schreuder et al., Nature 386:194-200, 1997
122 Mathis et al., Clin Chem 41: 1391-1397, 1995
123 Vigers et al., Nature 386:190-194, 1997

The invention claimed is:

1. An isolated nucleic acid molecule encoding an antibody specific for IL-1R1 comprising a set of CDRs: HCDR1, HCDR2, HCDR3, LCDR1, LCDR2 and LCDR3 wherein:
HCDR1 has the amino acid sequence of SEQ. ID. NO: 63;
HCDR2 has the amino acid sequence of SEQ. ID. NO: 64;
HCDR3 has the amino acid sequence of SEQ. ID. NO: 65;
LCDR1 has the amino acid sequence of SEQ. ID. NO: 68;
LCDR2 has the amino acid sequence of SEQ. ID. NO: 69; and
LCDR3 has the amino acid sequence of SEQ. ID. NO: 70.

2. A host cell transformed with a nucleic acid molecule according to claim 1.

3. The isolated nucleic acid molecule of claim 1, wherein the nucleic acid molecule is operably linked to a regulatory sequence.

4. A vector comprising the nucleic acid molecule of claim 3.

5. The host cell of claim 2, wherein the host cell is a mammalian host cell.

6. The mammalian host cell of claim 5, wherein the host cell is a Chinese hamster ovary (CHO) cell, a HeLa cell, a baby hamster kidney cell, a NS0 mouse melanoma cell, a YB2/0 rat myeloma cell, a human embryonic kidney cell, or a human embryonic retina cell.

* * * * *